United States Patent
Wentworth et al.

(10) Patent No.: US 12,364,550 B2
(45) Date of Patent: Jul. 22, 2025

(54) VIRTUAL REALITY WRIST ASSEMBLY

(71) Applicant: Vicarious Surgical Inc., Waltham, MA (US)

(72) Inventors: Marshall Wentworth, Waltham, MA (US); Eric Kline, Malden, MA (US); Michael Eilenberg, Cambridge, MA (US); Sammy Khalifa, Medford, MA (US)

(73) Assignee: Vicarious Surgical Inc., Waltham, MA (US)

(*) Notice: Subject to any disclaimer, the term of this patent is extended or adjusted under 35 U.S.C. 154(b) by 429 days.

(21) Appl. No.: 17/875,193

(22) Filed: Jul. 27, 2022

(65) Prior Publication Data
US 2022/0370162 A1  Nov. 24, 2022

Related U.S. Application Data

(63) Continuation of application No. 16/189,526, filed on Nov. 13, 2018, now Pat. No. 11,576,732.
(Continued)

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/00234* (2013.01); *A61B 34/71* (2016.02);
(Continued)

(58) Field of Classification Search
CPC ................... A61B 34/30; A61B 34/71; A61B 17/00234; A61B 2034/2059; A61B 2034/305; A61B 2034/306; A61B 2090/035
See application file for complete search history.

(56) References Cited

U.S. PATENT DOCUMENTS

| 3,739,923 A | 6/1973 | Totsuka |
| 3,784,031 A | 1/1974 | Niitu et al. |
| (Continued) | | |

FOREIGN PATENT DOCUMENTS

| CN | 102143719 A | 8/2011 |
| CN | 104434318 A | 3/2015 |
| (Continued) | | |

OTHER PUBLICATIONS

International Search Report and Written Opinion for Application No. PCT/US2018/060656, dated Jan. 22, 2019, 12 pages.
(Continued)

*Primary Examiner* — Michael F Peffley
*Assistant Examiner* — Bo Ouyang
(74) *Attorney, Agent, or Firm* — McCarter & English, LLP

(57) ABSTRACT

A surgical apparatus system for minimally invasive surgery (MIS) which includes a wrist assembly. The wrist assembly includes a first jaw, a first actuation hub, and a cable redirecting hub operably coupled to the first actuation hub, a second jaw, a second actuation hub, a housing for the first and second jaws, a first cable, a second cable, a third cable, rotational position sensors, and a control system. The first and second jaws of the wrist assembly are movably opposed, and the cables are configured such that applying tensions upon them cables produces rotation about a jaw axis. The wrist assembly may further include a hinge-rotary assembly to configured to provide rotation about a pitch axis and/or a roll axis. The wrist assembly may further include a fourth cable configured such that applying tensions upon the fourth cable and the opposing cable produces rotation about a pitch axis.

31 Claims, 36 Drawing Sheets

Related U.S. Application Data

(60) Provisional application No. 62/585,277, filed on Nov. 13, 2017.

(51) Int. Cl.
*A61B 34/00* (2016.01)
*A61B 34/20* (2016.01)
*A61B 90/00* (2016.01)

(52) U.S. Cl.
CPC .......... *A61B 2034/2059* (2016.02); *A61B 2034/305* (2016.02); *A61B 2034/306* (2016.02); *A61B 2090/035* (2016.02)

(56) References Cited

U.S. PATENT DOCUMENTS

| | | | |
|---|---|---|---|
| 4,341,144 A | 7/1982 | Milne | |
| 4,579,380 A | 4/1986 | Zaremsky et al. | |
| 5,458,387 A | 10/1995 | Conway et al. | |
| 5,860,995 A | 1/1999 | Berkelaar | |
| 5,895,084 A | 4/1999 | Mauro | |
| 5,968,074 A | 10/1999 | Prestel | |
| 6,394,998 B1 | 5/2002 | Wallace et al. | |
| 6,554,844 B2 | 4/2003 | Lee et al. | |
| 6,676,684 B1 | 1/2004 | Morley et al. | |
| 6,746,443 B1 | 6/2004 | Morley et al. | |
| 6,969,385 B2 | 11/2005 | Moreyra | |
| 7,131,977 B2 | 11/2006 | Fowler | |
| 7,320,700 B2 | 1/2008 | Cooper et al. | |
| 7,372,229 B2 | 5/2008 | Farritor et al. | |
| 7,410,483 B2 | 8/2008 | Danitz et al. | |
| 7,608,083 B2 | 10/2009 | Lee et al. | |
| 7,615,066 B2 | 11/2009 | Danitz et al. | |
| 7,699,835 B2 | 4/2010 | Lee et al. | |
| 7,766,894 B2 | 8/2010 | Weitzner et al. | |
| 7,935,130 B2 | 5/2011 | Williams | |
| 8,237,388 B2 | 8/2012 | Jinno et al. | |
| 8,246,027 B2 | 8/2012 | Li et al. | |
| 8,414,568 B2 | 4/2013 | Harlan | |
| 8,500,721 B2 | 8/2013 | Jinno | |
| 8,534,729 B2 | 9/2013 | Wilkinson et al. | |
| 8,679,096 B2 | 3/2014 | Farritor et al. | |
| 8,810,638 B2 | 8/2014 | Allen et al. | |
| 8,821,480 B2 | 9/2014 | Burbank | |
| 8,845,681 B2 | 9/2014 | Grace | |
| 8,992,565 B2 | 3/2015 | Brisson et al. | |
| 9,402,619 B2 | 8/2016 | Grace | |
| 9,526,566 B1 * | 12/2016 | Johnson | A61B 18/1445 |
| 9,700,381 B2 | 7/2017 | Amat Girbau | |
| 2012/0209314 A1 | 8/2012 | Weir et al. | |
| 2015/0088158 A1 | 3/2015 | Shellenberger et al. | |
| 2016/0058516 A1 | 3/2016 | Stefanchik et al. | |
| 2016/0120601 A1 * | 5/2016 | Boudreaux | A61B 18/1445 606/33 |
| 2016/0303743 A1 | 10/2016 | Rockrohr | |
| 2017/0181802 A1 | 6/2017 | Sachs et al. | |
| 2018/0055583 A1 * | 3/2018 | Schuh | A61B 34/37 |
| 2018/0242991 A1 * | 8/2018 | Beira | A61B 17/3201 |
| 2019/0142531 A1 | 5/2019 | Wentworth et al. | |

FOREIGN PATENT DOCUMENTS

| | | |
|---|---|---|
| CN | 105163679 A | 12/2015 |
| CN | 105813582 A | 7/2016 |
| CN | 106456145 A | 2/2017 |
| JP | 2017514608 A | 6/2017 |
| JP | 7233427 B2 | 3/2023 |
| WO | 2013/180773 A1 | 12/2013 |
| WO | 2015/171614 | 11/2015 |
| WO | 2016/186999 A1 | 11/2016 |

OTHER PUBLICATIONS

International Preliminary Report on Patentability for Application No. PCT/US2018/060656, dated May 28, 2020, 6 pages.

Japanese Office Action for Application No. 2020-526238 dated Sep. 28, 2022, 11 pages. .

U.S. Appl. No. 16/189,526, filed Nov. 13, 2018.

* cited by examiner

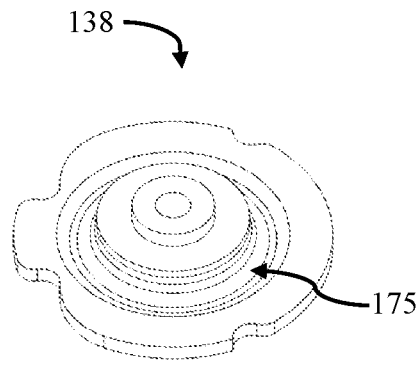
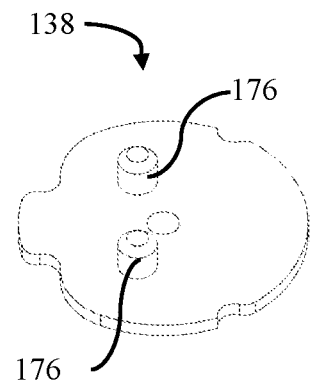
FIG. 15A  FIG. 15B
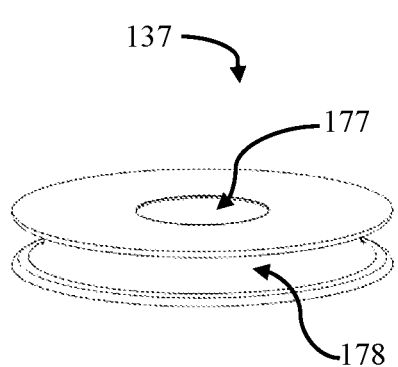
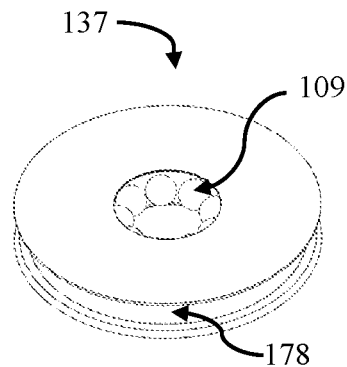
FIG. 16A  FIG. 16B

VIRTUAL REALITY WRIST ASSEMBLY

CROSS-REFERENCES TO RELATED APPLICATIONS

This application is a continuation of U.S. patent application Ser. No. 16/189,526, entitled "Virtual Reality Wrist Assembly," filed Nov. 13, 2018, which claims priority to U.S. Provisional Patent Application No. 62/585,277, entitled "Virtual Reality Wrist Assembly," filed on Nov. 13, 2017. The entire contents of each of these applications are herewith incorporated herein by reference in their entirety.

BACKGROUND

Field of Invention

This application generally relates to minimally invasive surgery, minimally invasive surgical tools and end-effectors and virtual reality minimally invasive surgical systems.

Description of Related Art

The field of minimally invasive surgery has undergone tremendous development and growth since its inception in the 1900's, with said developments and growth yielding improved results for patients. One of the major developments in the minimally invasive surgery field has been the implementation of surgical robotic devices. The implementation and utilization of surgical robotic devices in the minimally invasive surgery field has led to an increase in the number and types of surgeries that can be performed using said devices. Additionally, surgical robotic devices have recently been implemented and utilized in virtual reality surgeries.

In virtual reality surgeries, the surgeon has the perception of being disposed inside a patient's body at a surgical site. In conjunction with three-dimensional visualization provided by virtual reality goggles, the surgeon views the operation and interacts with robotic arms inserted in a patient's body, as if his or her own arms and hands have taken the form of the robotic arms. With virtual reality surgeries, the surgeon is engrossed in a natural and immersive virtual reality user interface.

Often during minimally invasive surgeries and virtual reality surgeries, robotically controlled instruments are utilized to perform a variety of tasks and functions during a procedure. One configuration of said instruments contains an end-effector assembly which includes a tool such as forceps, graspers, cautery tool, cutting tool and/or the like, with said tool affixed to a wrist assembly located at the distal end of an elongate shaft or tube. Typically, during a surgical procedure, the end-effector assembly, wrist assembly and a portion of the elongate shaft is inserted into the patient's body through a natural office or a small incision made in the patient's body, such that the end-effector assembly is situated in a desired surgical workspace. The wrist assembly can be used to position and actuate the tool during a procedure so as to allow a desired surgical task to be performed, within the surgical work space.

Typically, cables, wires and/or the like, traverse from the elongated shaft and can connect the wrist assembly to a drive assembly, which is used to provide actuation forces on said cables to actuate and/or manipulate the end-effector and wrist assembly of the instrument. The drive assembly can be mounted on a robotic surgical arm or coupled to another surgical robotic system controlled by a surgeon, with said arm or system containing a user interface system so as to allow the surgeon to control and manipulate the instrument. Generally, the wrist assembly of the instrument is configured to provide certain degrees of freedoms for motion of the end-effector, so as to allow different surgical tasks and procedures to be performed. Wrist assemblies generally, can implement various degrees of freedom to the end-effector including yaw, pitch, roll and/or grasping/grip of the end-effector.

Typically, wrist assemblies or mechanisms of instruments comprise various components and parts in order to implement various degrees of freedoms to end-effectors. Generally, wrist assemblies or mechanisms contain capstans, pulleys or the like, with cables connected to said capstans or pulleys, to rotate a portion of the wrist assembly that is coupled to the capstan or pulley. Usually, in its simplest form one pulley or capstan is utilized per each degree of freedom of the wrist assembly, and two cables or wires are used to rotate the capstan or pulley in each direction for the degree of freedom, such that pulling on one cable and releasing one cable results in rotation in one direction and pulling on the opposite cable and releasing the other cable results in rotation in the opposite direction. With these configurations, a total of six cables is needed in order for a wrist assembly to have three degrees of freedom. Alternatively, other wrist assemblies utilize a plurality of pulleys and cables per each degree of freedom, resulting in complex and cumbersome assemblies with limited ranges of motion.

The amount of cables required for three degrees of freedom can impact the efficiency of a wrist assembly, as well as restrict the movement of said wrist assembly. The use of multiple cables per one degree of freedom creates inherent complications in wrist assemblies of surgical robotic systems. Typically, surgical robotic systems contain robotic arms that are inserted into a patient's body, with actuation components such as cables or wires routed outside of the patient's body to a drive assembly.

Generally, robotic arms contain multiple degrees of freedom, however the number of degrees of freedom are restricted due to the size of the arms, as well as are confined in movement due to the boundaries of the work space inside a patient. The size constraints of robotic arms of surgical robotic systems impact the number of cables that can be routed from the drive assembly through the arms and to a wrist assembly, thus limiting the number of degrees of freedom attainable by the system.

The restrictions and limitations encountered by surgical robotic systems with robotic arms has denoted the importance of having a wrist assembly with multiple degrees of freedoms to allow for concise movements in densely condensed work spaces. This is especially true for virtual reality surgeries, utilizing in vivo surgical robotics designed to replicate the degrees of freedom of a human arm.

As a result, there is a desire for a wrist assembly having multiple degrees of freedom that can be actuated with a minimal amount of cables to effectuate concise movements in tight work spaces, while providing enough force to perform desired tasks and functions and capable of making intuitive movements so to allow a surgeon to actuate and control the wrist assembly based on the movement of the surgeon's arms and hands.

With human-like robotic systems, having a successful system results from maintaining a natural and intuitive human-machine interface (HMI). As such, it is advantageous in a virtual reality surgery for a surgeon to be able to have a wrist assembly capable of maintaining the functionality of a human-like robot, while still be able to perform desired surgical tasks and functions in confined work spaces.

BRIEF SUMMARY OF INVENTION

The present technology is directed to a surgical apparatus system and methods for minimally invasive surgery (MIS).

Technology includes a wrist assembly comprising a jaw assembly. The jaw assembly comprises a first jaw having a first working segment, a first actuation hub, and a cable redirecting hub operably coupled to the first actuation hub, wherein the first actuation hub comprises a cable passageway and defines an outer perimeter, and wherein the cable redirecting hub comprises a redirecting hub cable raceway adjacent to the outer perimeter of the first actuation hub. The jaw assembly further comprises a second jaw having a second working segment and a second actuation hub, the second actuation hub comprising a first cable raceway disposed along the outer perimeter of the second actuation hub. The jaw assembly further comprises a housing for the first and second jaws, the housing comprising a first body and a second body, wherein the housing is configured to allow the first jaw and the second jaw to rotate about a jaw axis and wherein the first jaw and the second jaw are movably opposed. The jaw assembly further comprises a first cable disposed in at least a portion of the first cable raceway and coupled to the second jaw, a second cable disposed in the cable passageway and coupled to the second jaw, a third cable disposed in at least a portion of the redirecting hub cable raceway and coupled to the first jaw, at least one first rotational position sensor disposed proximate to the jaw axis and configured to detect rotation of one or more of the first or second jaws about the jaw axis, and a control system configured to rotate one or more of the first or second jaws about the jaw axis.

The technology is configured such that applying a first tension to the first cable greater than a second tension applied to the second cable generates a first torque along the jaw axis that causes the second jaw to rotate about the jaw axis towards the first jaw. The technology is further configured such that applying the second tension to the second cable greater than the first tension applied to the first cable, generates a second torque along the jaw axis that causes the second jaw to rotate about the jaw axis away from the first jaw. The technology is further configured such that applying a third tension to the third cable greater than the second tension applied to the second cable, generates a third torque along the jaw axis and causes the first jaw to rotate about the jaw axis towards the second jaw. The technology is further configured such that applying the second tension to the second cable greater than the third tension applied to the third cable generates a fourth torque along the jaw axis that causes the first jaw to rotate about the jaw axis away from the second jaw.

In one embodiment of the technology, the wrist assembly may further comprise a hinge-rotary assembly configured to provide rotation of the jaw assembly about a pitch axis and configured to provide rotation of the hinge-rotary assembly about a roll axis. The hinge-rotary assembly may comprise a female rotary body defining a cavity, a hinge-rotary body, a hinge cover, and at least one idler pulley disposed between the hinge rotary body and hinge cover. The hinge-rotary body may comprise a proximal end having a cable conduit, wherein the cable conduit houses one or more of the first cable, the second cable, or the third cable, at least a portion of the hinge-rotary body disposed within the cavity of the female rotary body. The idler pulley may have an idler raceway disposed along an outer perimeter of the idler pulley, and the idler pulley may be disposed about the pitch axis. The second cable may be disposed in at least a portion of the idler raceway.

One aspect of the embodiment of the technology is that the hinge-rotary assembly of the wrist assembly may further comprise a rotary pulley body operably coupled to the proximal end of the hinge-rotary body, wherein the hinge-rotary body rotates with the rotary pulley body relative to the female rotary body to provide rotational movement about the roll axis.

Another aspect of the embodiment of the technology is that the wrist assembly may further comprise a plurality of bearings, wherein the plurality of bearings is located between one or more of: the hinge-rotary body and the first body of the jaw assembly; the hinge-rotary body and a male bearing race; the at least one idler pulley and the first body of the jaw assembly; the hinge cover and the second body of jaw assembly; or the hinge cover and a male bearing race.

Another aspect of the embodiment of the technology is that the hinge-rotary assembly may further comprise a decoupling surface configured to allow one or more of the first cable, the second cable, or the third cable to ride along at least a portion of the decoupling surface to reduce a length change in the one or more of the first cable, the second cable, or the third cable while pivoting about the center of the pitch axis relative to a length change in the one or more of the first cable, the second cable, or the third cable in the absence of the decoupling surface. The decoupling surface may further be located on at least one of the hinge cover or the hinge-rotary body. The wrist assembly may further comprise at least one second rotational position sensor disposed proximate to the pitch axis and configured to detect rotation of the jaw assembly about the pitch axis. The wrist assembly may further comprise a plurality of second rotational position sensors located at the pitch axis. The wrist assembly may further comprise at least one electronic communication component configured to transmit information captured by the at least one first rotational position sensor or at least one second rotational position sensor. The at least one electrical communication component comprises a flexible printed circuit board (FPCB). The at least one electrical communication component comprises a printed circuit board (PCB). The first housing body of the wrist assembly may further comprise a hinge stop configured to prevent the jaw assembly from rotating past a threshold of rotation about the pitch axis.

In another aspect of the embodiment of the technology, the wrist assembly may further comprise a fourth cable coupled to one of the first body and the second body of the jaw assembly. The wrist assembly may be configured such that applying a fourth tension to the fourth cable greater than an opposing tension applied to an opposing cable generates a fifth torque along the pitch axis that causes the jaw assembly to rotate about the pitch axis in a first pitch direction. The wrist assembly may be further configured such that applying the opposing tension to the opposing cable greater than the fourth tension applied to the fourth cable generates an opposing torque along the pitch axis that causes the jaw assembly to rotate about the pitch axis in a second pitch direction, the second pitch direction being rotation about the pitch axis in the opposite direction of the first pitch direction. The opposing cable and the opposing tension may be one or more of: the first cable and the first cable tension; the second cable and the second cable tension; or the third cable and the third cable tension. The opposing cable may be only one of the first cable, the second cable, or the third cable. The opposing cable may be the first cable, and applying the opposing tension to the opposing cable greater than the fourth tension may generate the opposing torque along the pitch axis and may cause the jaw assembly to rotate about the pitch axis in the second pitch direction. The opposing cable may be the second cable, and applying the opposing tension to the opposing cable greater than the fourth tension may generate the opposing torque along the pitch axis and may cause the jaw assembly to rotate about the pitch axis in the second pitch direction. The opposing cable may be the third cable, and applying the opposing tension to the opposing cable greater than the fourth tension may generate the opposing torque along the pitch axis and may cause the jaw assembly to rotate about the pitch axis in the second pitch direction.

In another aspect of the embodiment of the technology, the control system may be further configured to accept data from one or more of the at least one first rotational position sensor or the at least one second rotational positional sensor and determine one or more of the first tension, second tension, third tension, fourth tension, or opposing tension to cause rotation of the jaw assembly about one or more of the pitch axis or the jaw axis. The control system may further comprise at least one actuator configured to apply a tension to one of the first cable, second cable, third cable or fourth cable, and the actuator may be one of a stepper motor, servo-motor, hydraulic actuator, pneumatic actuator, piezoelectric motor, or ultrasonic transducer.

In another embodiment of the technology, the cable redirecting hub and the first actuation hub may be of monolithic construction.

In another embodiment of the technology, the cable redirecting hub may comprise a redirecting pin, and the second cable may pass around at least a portion of the redirecting pin within the cable passageway.

In another embodiment of the technology, the first actuation hub may further comprise a first cable routing protrusion, and the first cable routing protrusion may be configured to provide a surface for the second cable to ride along during the rotation of the first jaw about the jaw axis in a first direction.

In an aspect of the embodiment of the technology, the first cable routing protrusion may be configured to reduce torque along the jaw axis during rotation of the first jaw about the jaw axis in the first direction relative to torque along the jaw axis during rotation of the first jaw about the jaw axis in the first direction in the absence of the first cable routing protrusion.

In another aspect of the embodiment of the technology, the first cable routing protrusion may be configured to reduce a length change in the second cable during rotation of the first jaw about the jaw axis in the first direction relative to the length change in the second cable during rotation of the first jaw about the jaw axis in the first direction in the absence of the first cable routing protrusion.

In another aspect of the embodiment of the technology, the first actuation hub may further comprise a second cable routing protrusion, and the second cable routing protrusion may be configured to provide a surface for the second cable to ride along during the rotation of the first jaw about the jaw axis in a second direction, the second direction being an opposite direction of rotation relative to the first direction. The second cable routing protrusion may be further configured to reduce torque along the jaw axis during rotation of the first jaw about the jaw axis in the second direction relative to torque along the jaw axis during rotation of the first jaw about the jaw axis in the second direction in the absence of the second cable routing protrusion. The second cable routing protrusion may also be further configured to reduce a length change in the second cable during rotation of the first jaw about the jaw axis in the second direction relative to the length change in the second cable during rotation of the first jaw about the jaw axis in the second direction in the absence of the second cable routing protrusion.

In another embodiment of the technology, the first actuation hub may further comprise a first fulcrum and a first cable pulley disposed about the first fulcrum.

In an aspect of the embodiment of the technology, the first actuation hub may further comprise a second fulcrum and a second cable pulley disposed about the second fulcrum. The second cable may pass around the first cable pulley and the second cable pulley. The second cable may have a wrap angle around the first cable pulley of about 240 to 300 degrees, and the second cable may have a wrap angle around the second cable pulley of less than about 110 degrees.

In another embodiment of the technology, the wrist assembly may further comprise a plurality of first rotational position sensors disposed proximate to the jaw axis.

In another embodiment of the technology, the first working segment and second working segment may be configured to be electrically isolated from the rest of the jaw assembly.

In an aspect of the embodiment of the technology, the first working segment and second working segment may be configured as a cautery tool.

In another embodiment of the technology, the control system may further comprise at least one actuator configured to apply a tension to one of the first cable, second cable, or third cable. The actuator may be one of a stepper motor, servo-motor, hydraulic actuator, pneumatic actuator, piezoelectric motor, or ultrasonic transducer.

In another embodiment of the technology, the first jaw and second jaw may be independently movable.

In another embodiment of the technology, the first body of the housing may further comprise a first jaw stop, the second body of the housing may further comprise a second jaw stop. The first jaw stop and the second jaw stop may be configured to prevent one or more of the first jaw or second jaw from rotating past a threshold of rotation about the jaw axis.

BRIEF DESCRIPTION OF FIGURES

Note that numbered items remain consistent across all figures. Items numbered with the same number are either the same item, or identical copies of the item. Items numbered with different numbers are either parts of different design, or are occasionally identical parts serving different purposes.

FIG. 15A is top isometric view of a male bearing race according to one embodiment.

FIG. 15B is a bottom isometric view of a male bearing race according to one embodiment.

FIG. 16A is a perspective view of an idler pulley according to one embodiment.

FIG. 16B is an isometric view of an idler pulley according to one embodiment.

DETAILED DESCRIPTION

Figure 1A:
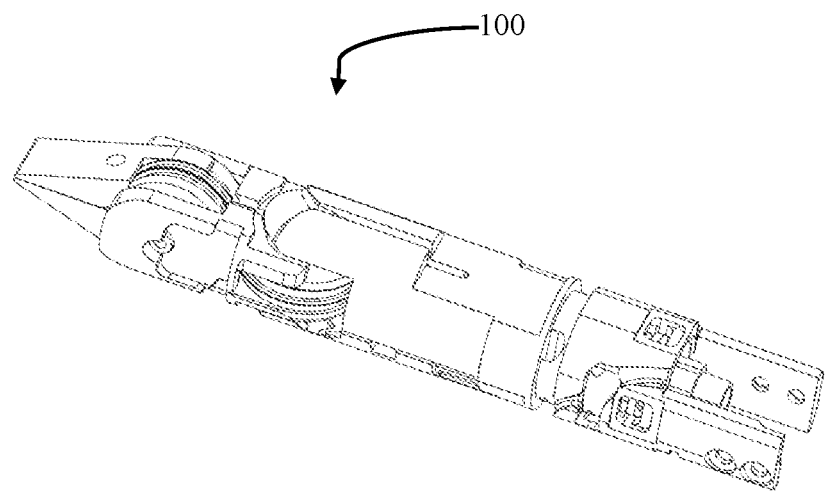
FIG. 1A is an isometric view of a wrist assembly according to one embodiment.
Figure 1B:
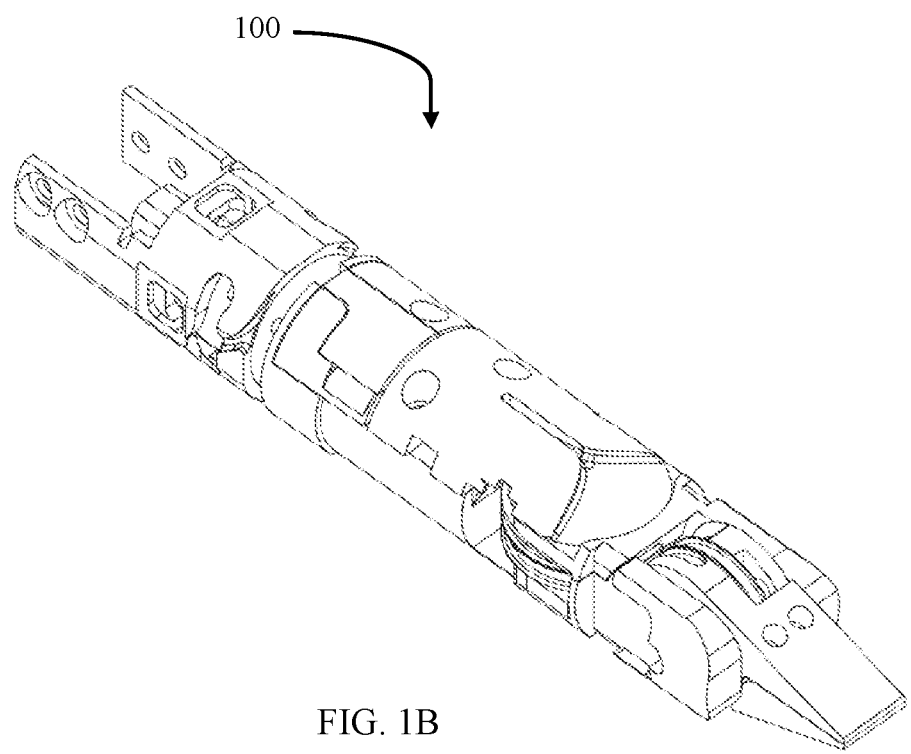
FIG. 1B is an additional isometric view of a wrist assembly according to one embodiment.
Figure 1C:
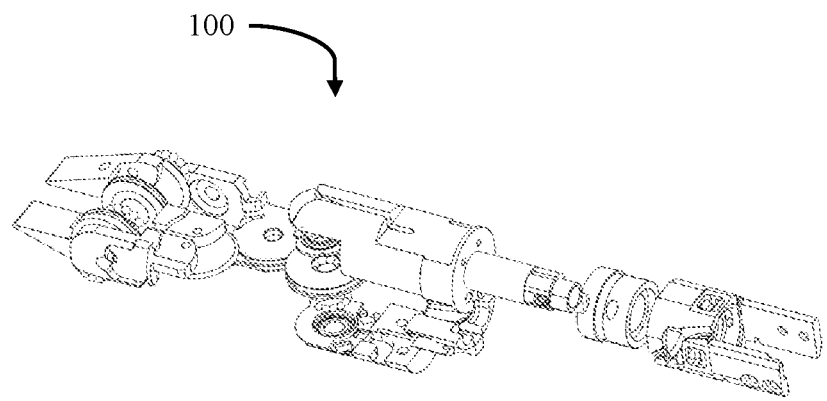
FIG. 1C is an exploded isometric view of a wrist assembly according to one embodiment.
Figure 1D:
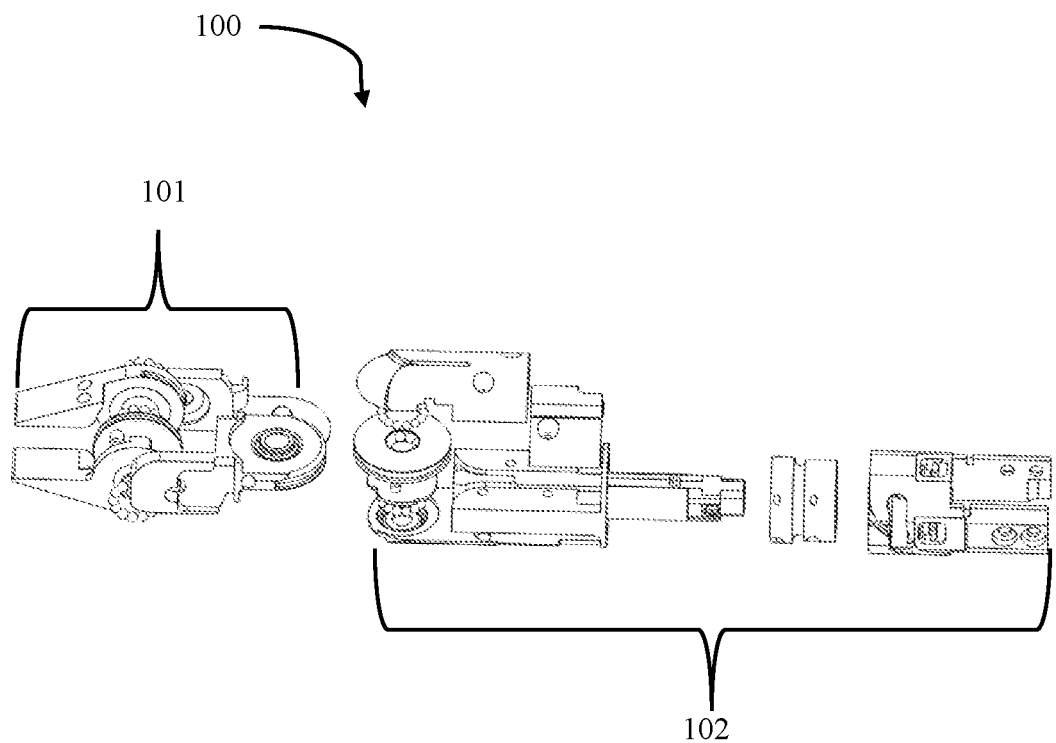
FIG. 1D is an additional exploded isometric view of a wrist assembly according to one embodiment.

While the present system is designed for use by a surgeon within the abdominal cavity, many alternative uses of the device are possible. For example, a user might be a physician's assistant, nurse, surgical aid, or any other surgical personnel. Additionally, the device could be disposed within any part of a patient's body, and future embodiments could be designed to be much smaller so as to allow for use within smaller areas of a patient's body. Both smaller and larger devices can be fabricated for uses in areas such as the paranasal sinuses, colon, stomach, or any other areas within the human body including but not limited to, the abdomen, cranium and cervicis. Micro-fabrication using MEMS or other means could allow for a device to be positionable within immensely small areas such as human blood vessels.

In some embodiments, the device may be used for non-surgical or non-medical tasks such as bomb diffusion, military reconnaissance, inspectional services, or any other task which requires concise movements in confined work spaces. In addition, some embodiments may be used for educational purposes, such as for training personnel. Some embodiments of the device could be fabricated to be human-sized or even larger-than-life, allowing humans to perform concise movement in tight work spaces that unable to be reached or viewed by a human. Obviously, in such embodiments, the user many not necessarily be a surgeon.

Overview

In particular embodiments, the surgical apparatus system disclosed herein is designed to be incorporated and utilized with the Virtual Reality Surgical Device disclosed in International Patent Application No. PCT/US2015/029247 (published as International Patent Publication No. WO2015171614A1), incorporated by reference herein in its entirety. Notwithstanding the above-sentence, in some embodiments the surgical apparatus disclosed herein can be implemented and utilized by other existing and future robotic surgery systems and/or devices.

The purpose of this apparatus is to provide a surgeon with a wrist assembly for an in vivo surgical robotic arm that emulates human wrist roll so as to maintain a natural and intuitive HMI while also allowing the surgeon to remain immersed in virtual reality during utilization of the Virtual Reality Surgical Device. The apparatus disclosed herein, provides the surgeon with a wrist assembly with four (4) degrees of freedom (DOF), which provides the surgeon with an apparatus that can emulate the wrist roll of the human arm via a yaw, pitch and roll actuator, thus allowing the surgeon to remain immersed in virtual reality while maintaining a natural and intuitive HMI.

The apparatus disclosed provides numerous advantages for surgeons, as it allows a surgeon to interact with the in vivo robotic device as if the device were the surgeon's arms and hands. This allows a surgeon to perform very difficult and delicate procedures in close quarters, while allowing said surgeon to maintain the natural motions to which he or she is accustomed when performing a procedure. The apparatus disclosed allows a surgeon to perform an operation in the manner and form in which he or she is accustomed, while being able to access areas of the body that would not otherwise be accessible using other robotic devices. Furthermore, the apparatus as disclosed, increases the surgeon efficiency during a procedure due to the surgeon ability to maintain a natural and intuitive HMI, while being immersed in virtual reality. This helps to reduce the operation time, and thus allowing a patient to commence their recovery sooner. Likewise, the increase in efficiency, helps a surgeon concentrate on performing a procedure, thus increasing a surgeon's work flow and improving his or her productivity.

Unless otherwise stated, the term "distal" as used herein means relativity further from a reference point, while "proximal" means relatively closer to a reference point. In general, the reference point will be the operator of the object being described.

Figure 1E:
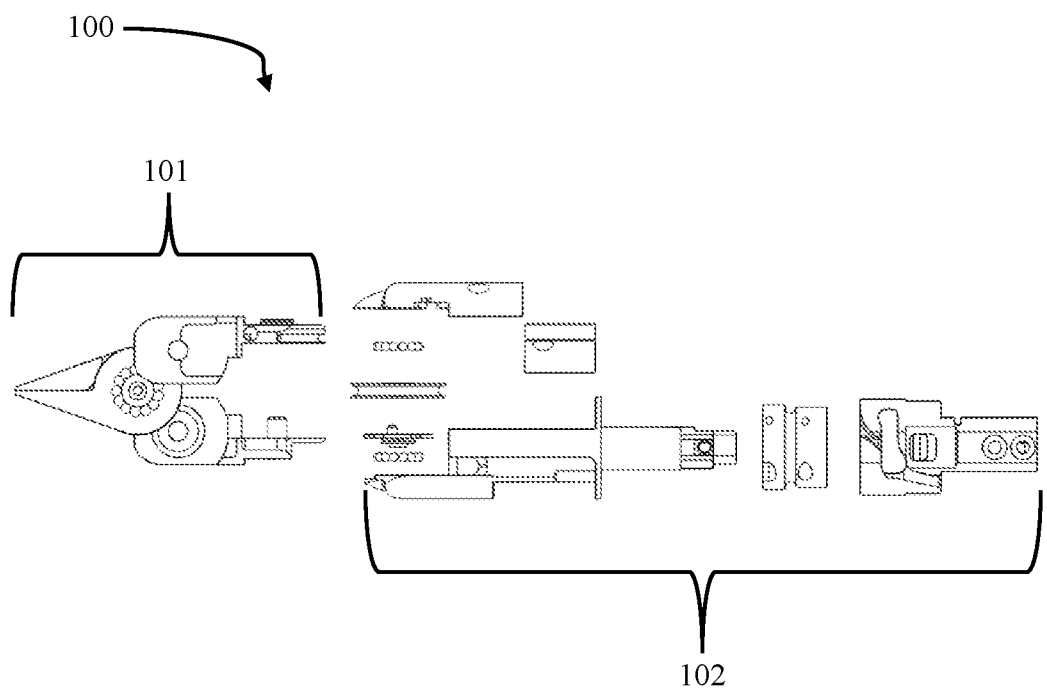
FIG. 1E is an exploded side profile view of a wrist assembly according to one embodiment.
Figure 1F:
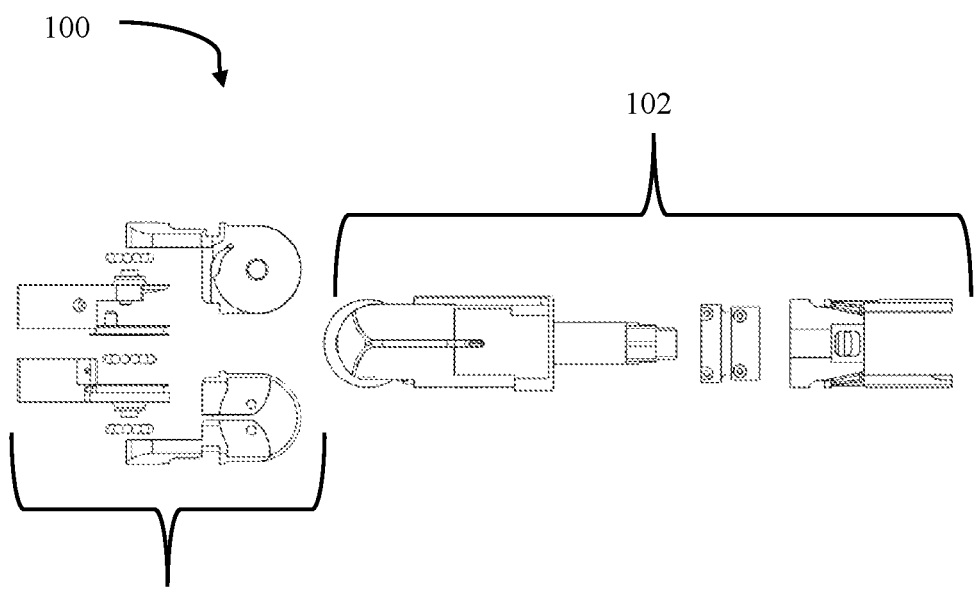
FIG. 1F is an exploded top profile view of a wrist assembly according to one embodiment.

FIG. 1A-1F show multiple views of one embodiment of a wrist assembly 100. In particular, FIG. 1E and FIG. 1F show exploded views of one embodiment of the wrist assembly 100. As depicted in the illustrative embodiment shown in FIG. 1E and FIG. 1F, the wrist assembly 100 consists of two subassemblies, a jaw assembly 101 and a hinge-rotary actuator assembly 102. Both of aforementioned subassemblies are essential to the overall wrist assembly 100, as both subassemblies in conjunction with one another are configured to provide a user with four degrees of freedom, as further detailed below.

FIG. 2A-2D show multiple views of one embodiment of the jaw assembly 101. The jaw assembly 101 is an essential part to the overall wrist assembly 100, as it performs crucial functions. The jaw assembly 101 functions as an end-effector for the Virtual Reality Surgical Device and is configured to interact with the surgical environment and perform surgical procedures within the operation work space. In addition, the jaw assembly 101 is configured to provide a surgeon with two DOFs, as well as configured to mate and couple to the hinge-rotary actuator assembly 102 to provide a surgeon with two additional DOFs.

Figure 2A:
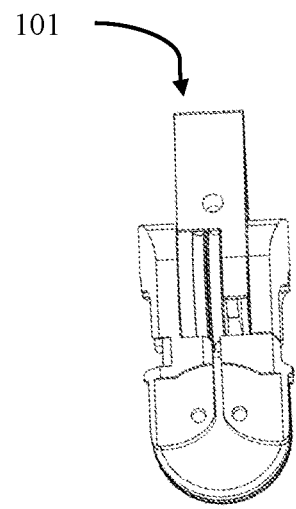
FIG. 2A is an isometric view of a jaw assembly according to one embodiment.
Figure 2B:
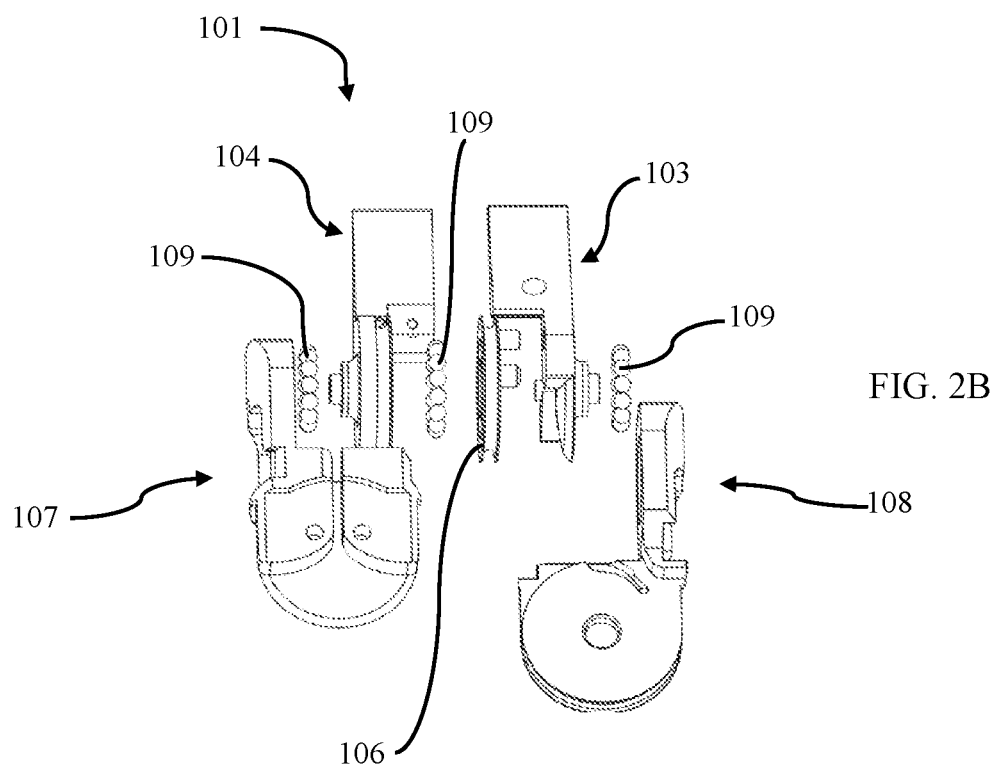
FIG. 2B is an exploded isometric view of a jaw assembly according to one embodiment.
Figure 2C:
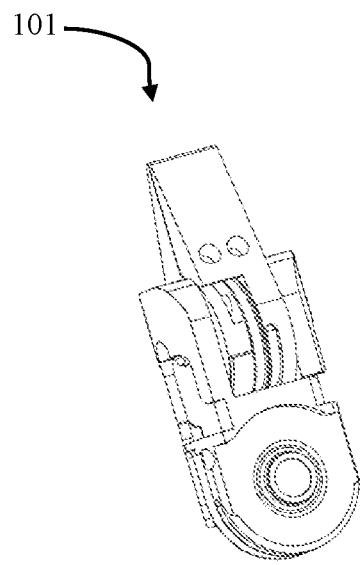
FIG. 2C is an additional isometric view of a jaw assembly according to one embodiment.
Figure 2D:
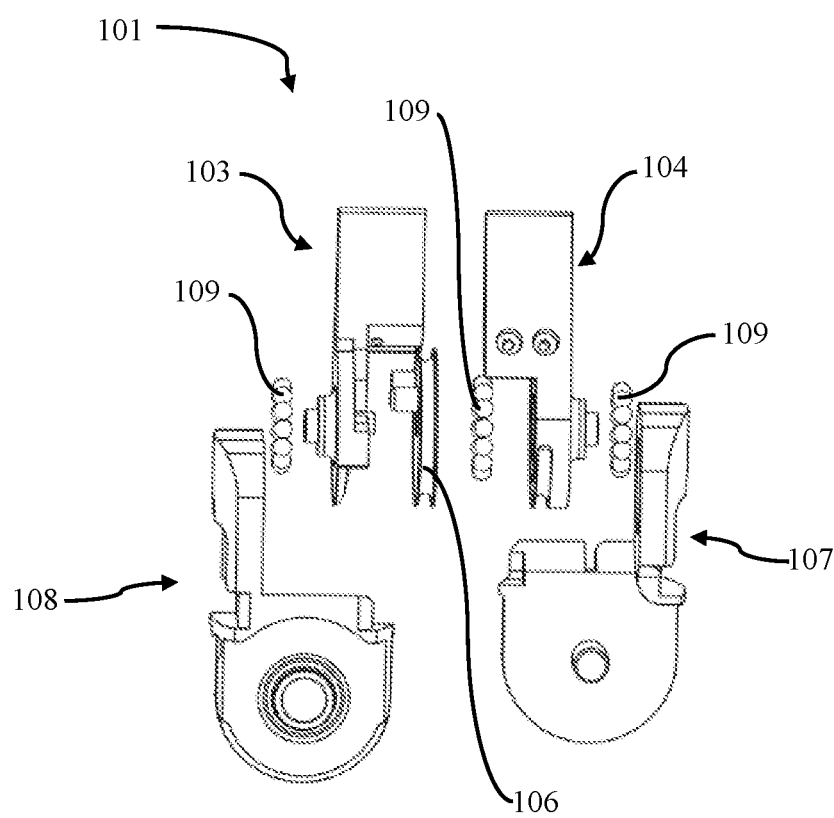
FIG. 2D is an additional exploded isometric view of a jaw assembly according to one embodiment.
Figure 3A:
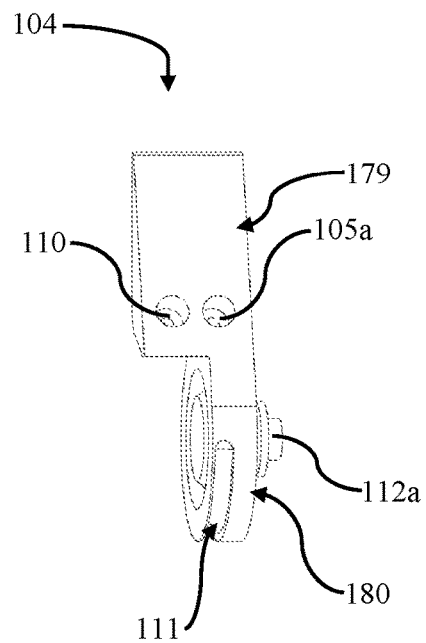
FIG. 3A is an isometric view of a second jaw according to one embodiment.
Figure 3B:
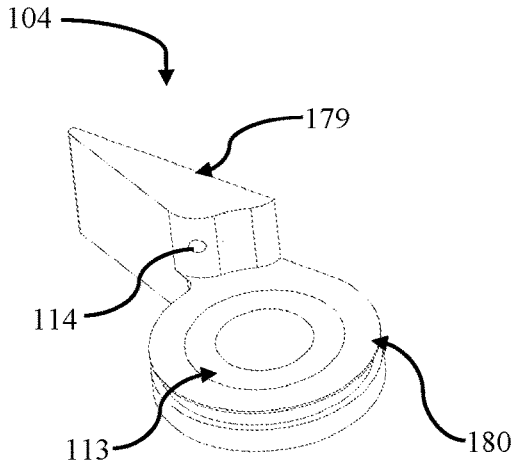
FIG. 3B is a side isometric view of a second jaw according to one embodiment.
Figure 3C:
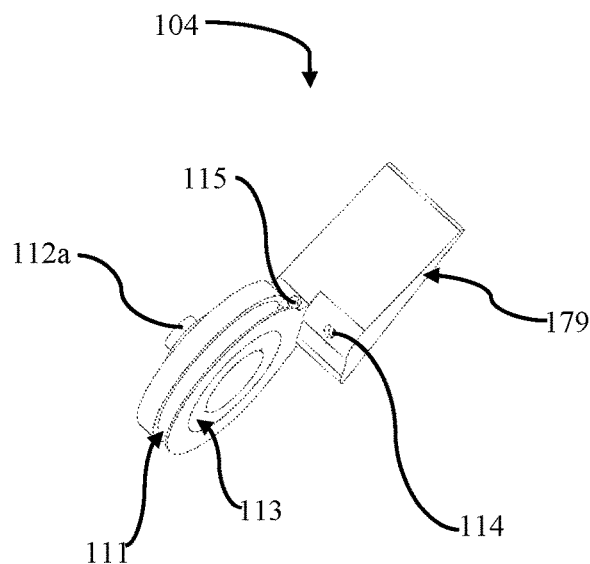
FIG. 3C is an additional isometric view of a second jaw according to one embodiment.
Figure 3D:
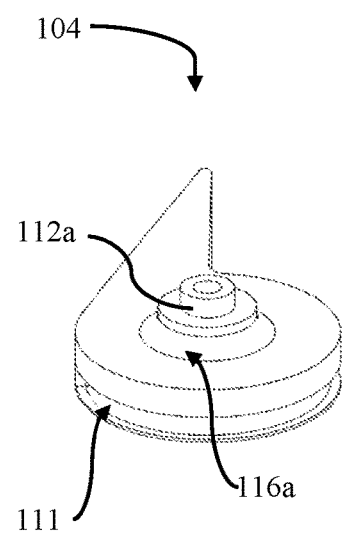
FIG. 3D is an additional side isometric view of a second jaw according to one embodiment.

FIG. 2B shows an exploded top isometric view of an illustrative embodiment of a jaw assembly 101, with FIG. 2D depicting an exploded bottom isometric view of an illustrative embodiment of a jaw assembly 101. As seen in FIG. 2B and FIG. 2D, in one embodiment, the jaw assembly 101 contains a first jaw 103 and a second jaw 104, a cable redirecting hub 106, a plurality of ball bearing sets 109, and two bodies, a hinge flex body 107 and a hinge non-flex body 108.

As mentioned above, the jaw assembly 101 is configured to provide two DOFs to the wrist assembly 100. The jaw assembly 101 provides two DOFs by having the first jaw 103 and the second jaw 104 move independently of one another, as described in further detail below. FIGS. 3A-3D show multiple views of an illustrative embodiment of a second jaw 104. As shown in FIGS. 3A-3D, in one embodiment the second jaw 104 is fabricated to have a distal end containing a working segment 179 and a proximal end containing an actuation hub 180. In some embodiments, the working segment 179 and the actuation hub 180 are manufactured as one solid piece, while in other embodiment the working segment 179 and the actuation hub 180 are affixed to each other via a welded connection, adhesive connection, and/or any other connection methods or techniques known in the art.

The working segment 179 of the second jaw 104 allows a surgeon to grasp, and manipulate tissues, as well as grasp surgical tools. In different embodiments, working segment 179 can take on a myriad of configurations, allowing a surgeon to perform a variety of procedures and tasks. In some embodiments, working segment 179 of the second jaw 104 contains rigid teeth on one side of said segment so to provide a surgeon with a gripping surface to hold and manipulate tissue and organs. In other embodiments, the working segment 179 is configured to contain a textured surface, smooth surface, a knurled surface, and/or have a protective coating on one side of said segment. Furthermore, in some embodiments, working segment 179 of the second jaw 104 and working segment 183 of the first jaw 103 introduced below, contain the same configuration while in other embodiments, working segment 179 of the second jaw 104 and working segment 183 of the first jaw 103 contain different configurations.

In addition, in some embodiments working segment 179 is configured to be electrically conductive. In these embodiments, the first jaw 103 and the second jaw 104 are configured as a cautery tool, allowing a surgeon to perform cautery functions. In these embodiments, electrical cautery wires are routed through the wrist assembly 100 to the first and second jaw, with the first and second jaws containing electrical insulation, so as to electrically isolate the first and second jaws or the working segments 183 and 179 from the rest of the wrist assembly 100. In these embodiments, the working segments 183 and 179 of the first and second jaw are configured to perform electrocautery functions, utilizing both the monopolar cautery method, as well as the bipolar cautery method. In different embodiments, the working segments 183 and 179 of the first and second jaws 103 and 104, are configured as a variety of surgical tools, including but not limited to forceps, vessel sealers, needle drivers, surgical scissors, retractors, and/or any other surgical tools known in the art.

As detailed above, in some embodiments the second jaw 104 contains the actuation hub 180. In one embodiment, the actuation hub 180 of the second jaw 104 contains a cable routing raceway 111. The cable routing raceway 111 is configured to allow a cable 181 (not shown in FIGS. 3A-3D), to sit within said raceway, as well as to route the cable 181 to a cable aperture 115 located on the working segment 179 of the second jaw 104. The cable routing raceway 111 is configured to constrain the cable 181, so as to prevent said cable 181 from slipping off the raceway during actuation. The cable routing raceway 111 extends around the perimeter of the actuation hub 180, thus providing a surface for cable 181 to sit and ride along during actuation.

In addition, in some embodiments, on one side of the actuation hub 180 is a bearing race 113, which is configured to allow one of the pluralities of ball bearing sets 109 (FIG. 2B) to sit in. Likewise, in some embodiments, located on the other side of the actuation hub 180 is another bearing race 116a, which is configured to allow one of the pluralities of ball bearing sets 109 to ride on. It should be noted that in other embodiments, the plurality of ball bearing sets 109 eliminated, as certain embodiments of the technology do not require ball bearings. Certain embodiments comprise sleeve bearings, bushings, axle and/or other rolling element bearings known in the art. In addition, in some embodiments, located on the one side of the actuation hub 180 is a magnet housing 112a, with said housing containing an aperture in which a magnet sits. As further detailed below, the magnet is utilized to obtain position data and, in some embodiments, orientation data of the second jaw 104.

In some embodiments, the working segment 179 of the second jaw 104 contains a cable routing aperture 114. The cable routing aperture 114 is configured to allow a cable 182 (not shown in FIGS. 3A-3D), to enter said aperture and route said cable to a cable termination site 110, where cable 182 terminates. As mentioned above, located on the working segment 179 of the second jaw is the cable aperture 115. The cable aperture 115 is configured to route cable 181 to a cable termination site 105a, where said cable terminates.

In one embodiment, cable 182 and cable 181 terminate by means of clamping the respective cable in their respective termination site via a setscrew. Alternatively, cable 182 and cable 181 may terminate using any appropriate means or techniques known in the art. For example, a polymer fiber cable may terminate with a knot tied in the cable, while a metal fiber cable may be terminated by means of crimp and/or swaged connections.

FIGS. 4A-4D, show multiple views of an illustrative embodiment of the first jaw 103. As shown in FIGS. 4A-4D, in one embodiment, the first jaw 103 is fabricated to have a distal end containing a working segment 183 and a proximal end containing an actuation hub 184. Similar, to the second jaw 104, in some embodiments, the working segment 183 and the actuation hub 184 of the first jaw, are manufactured as one solid piece, while in other embodiments the working segment 183 and the actuation hub 184 are affixed to each other via a welded connection, an adhesive connection, and/or any other connection methods or techniques known in the art.

Figure 4A:
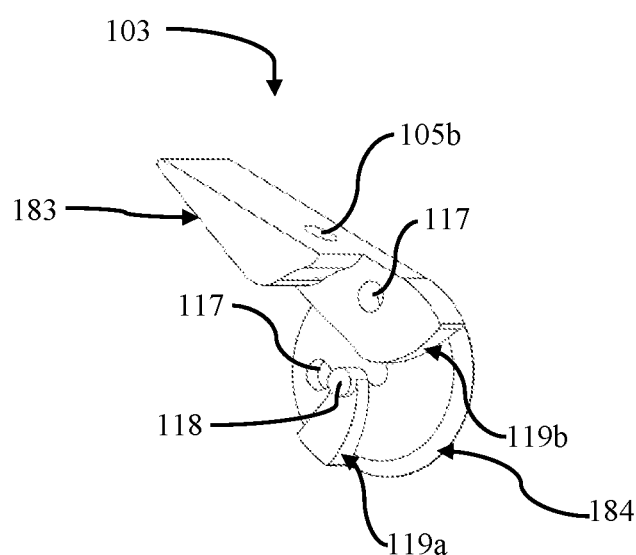
FIG. 4A is a side isometric view of a first jaw according to one embodiment.
Figure 4B:
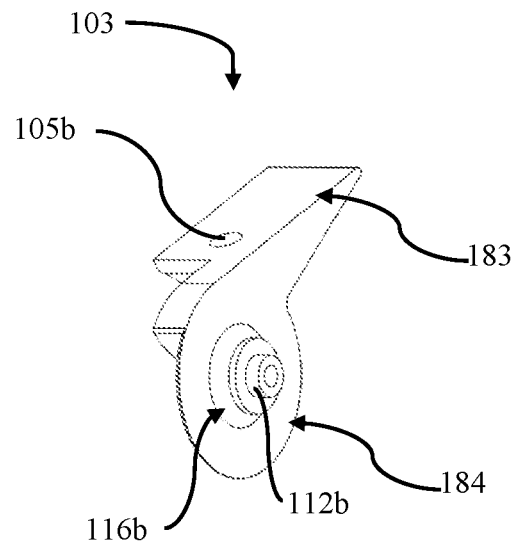
FIG. 4B is an additional isometric view of a first jaw according to one embodiment.
Figure 4C:
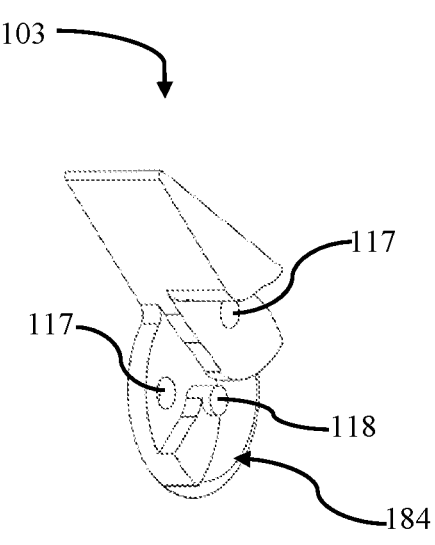
FIG. 4C is an additional isometric view of a first jaw according to one embodiment.
Figure 4D:
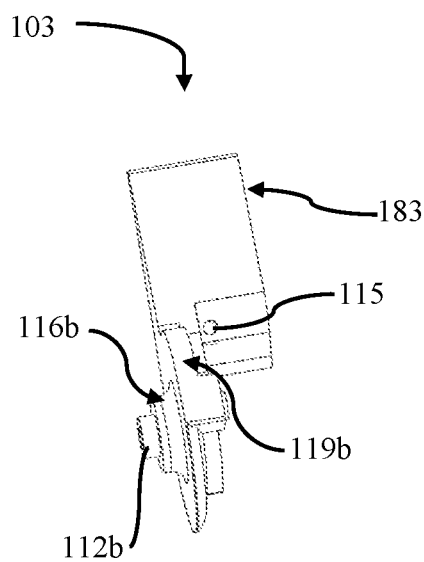
FIG. 4D is an additional isometric view of a first jaw according to one embodiment.

In addition, in some embodiments, the working segment 183 of the first jaw 103 contains a cable routing aperture 115 (FIG. 4D). The cable routing aperture 115 of the first jaw 103 is configured to route a cable 185 into a cable termination site 105b located on the working segment 183 of the first jaw 103, where said cable 185 terminates. In different embodiments, various methods and/or techniques known in the art are utilized to terminate cable 185 within cable termination site 105b. In one embodiment, cable 185 terminates by means of clamping said cable 185 within termination site 105b via a setscrew. In different embodiments, various methods and/or techniques known in the art are utilized to terminate cable 185 within cable termination site 105b. For example, a polymer fiber cable may terminate with a knot tied in the cable, while a metal fiber cable may be terminated by means of crimp and/or swaged connections.

In some embodiments, the actuation hub 184 of the first jaw 103 is fabricated to be circular in shape and contains two sides. Similar to the actuation hub 180 of the second jaw 104, in one embodiment, one side of the actuation hub 184 of the first jaw 103 contains a bearing race 116b, which is configured to allow one of the pluralities of ball bearing sets 109 to ride on. As mentioned above, in some embodiments the ball bearing set 109 are eliminated as certain embodiments of the technology do not require ball bearings. Certain embodiments comprise sleeve bearings, bushings, axle and/or other rolling element bearings known in the art. In some embodiments, located on same side of the actuation hub 184 as the bearing race 116b, is a magnet housing 112b, with said housing containing an aperture in which a magnet sits. As further detailed below, the magnet is utilized to obtain position data and, in some embodiments, orientation data of the first jaw 103.

Figure 5A:
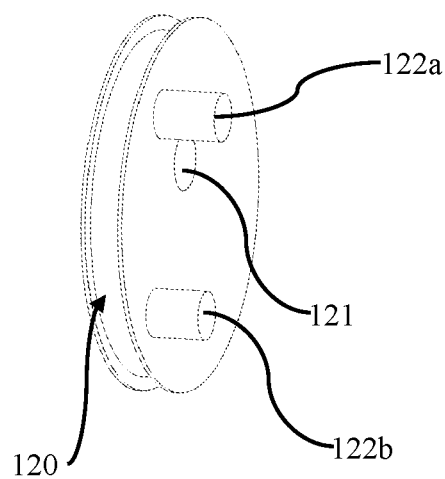
FIG. 5A is a side isometric view of a cable redirecting hub according to one embodiment.
Figure 5B:
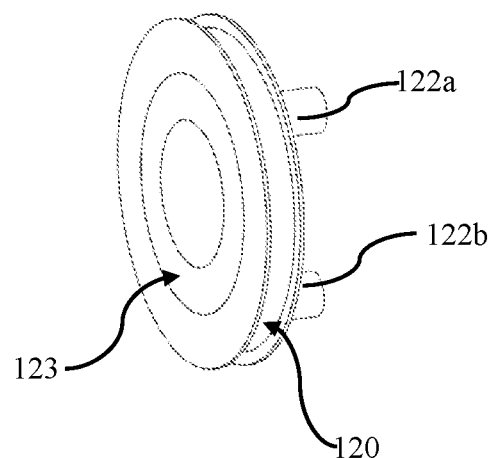
FIG. 5B is an additional side isometric view of a cable redirecting hub according to one embodiment.
Figure 5C:
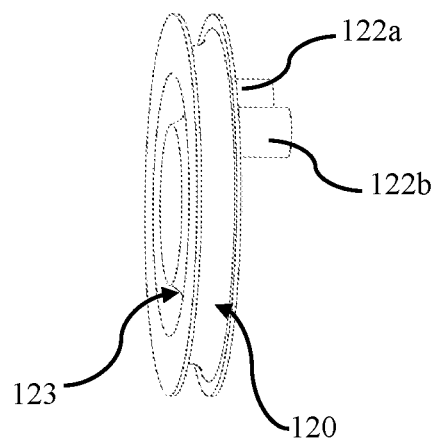
FIG. 5C is a front isometric view of a cable redirecting hub according to one embodiment.

In one embodiment, one side of the actuation hub 184 is configured to mate and couple with the redirecting cable hub 106 (FIGS. 5A-5C). In this embodiment, the actuation hub 184 contains a plurality of redirecting cable hub connection apertures 117, configured to allow connection pins 122a and 122b (FIGS. 5A-5C), located on the redirecting cable hub 106 to enter, thus coupling the actuation hub 184 of the first jaw 103 with the redirecting cable hub 106.

Additionally, in some embodiments, actuation hub 184 contains a cable routing pin 118, which is configured to route cable 182 to its respective termination site 110. In some embodiments, the cable routing pin 118 is coupled to a cable routing protrusion 119a. The cable routing protrusion 119a provides a surface for cable 182 to ride along when the first jaw 103 is actuated in a first direction. Moreover, cable routing protrusion 119a is configured to allow cable 182 to wrap around said protrusion 119a, effectuating a reduced change in length of cable 182 when the first jaw 103 is actuated in a first direction about the jaw axis, as well as configured to reduce torque about the jaw axis during rotation. In addition, in some embodiments, actuation hub 184 contains another cable routing protrusion 119b, which provides a surface for cable 182 to ride along during actuation of the first jaw 103 in a second direction. Similar to cable routing protrusion 119a, cable routing protrusion 119b is configured to allow cable 182 to wrap around said protrusion 119b, and also configured to effectuate a reduced change in length of cable 182 when the first jaw 103 is actuated in a second direction about the jaw axis, as well as reduce torque about the jaw axis during rotation. The actuation of the first jaw 103 and the second jaw 104 is further detailed below.

As mentioned above, the actuation hub 184 of the first jaw 103 mates and couples with the redirecting cable hub 106 via connection pins 122a and 122b that extend from the redirecting cable hub 106 and enter into connection apertures 117 located on actuation hub 184. In addition to mating and coupling the actuation hub 184 of the first jaw 103 with the redirecting cable hub 106, in some embodiments, connection pin 122a also provides a routing surface for cable 182 to guide said cable 182 to its termination site 110.

Figure 22A:
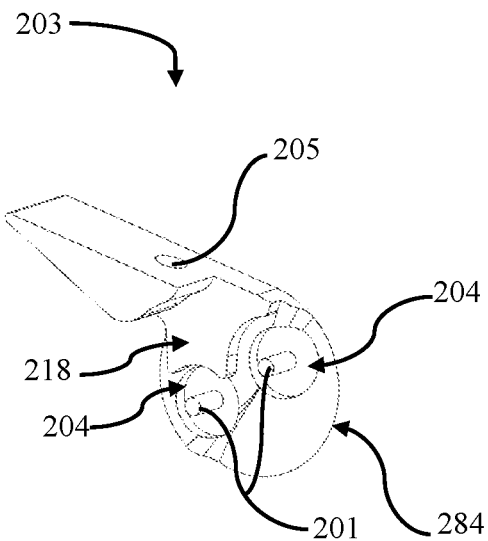
FIG. 22A shows a perspective view of an alternative embodiment of a first jaw.
Figure 22B:
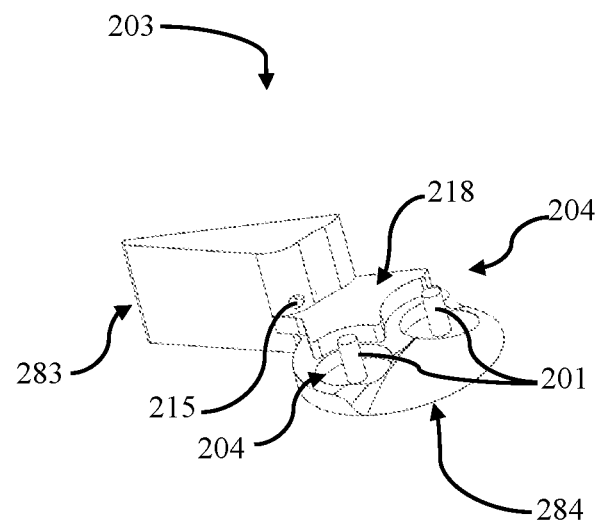
FIG. 22B shows a perspective view of an alternative embodiment of a first jaw.
Figure 23A:
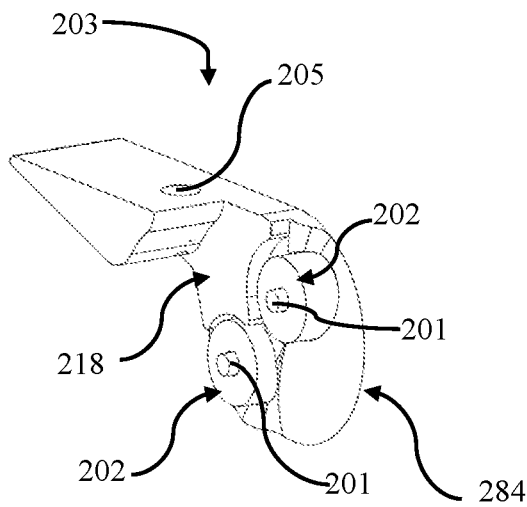
FIG. 23A shows a perspective view of a first jaw illustrating cable pulleys of said jaw according to one embodiment.
Figure 23B:
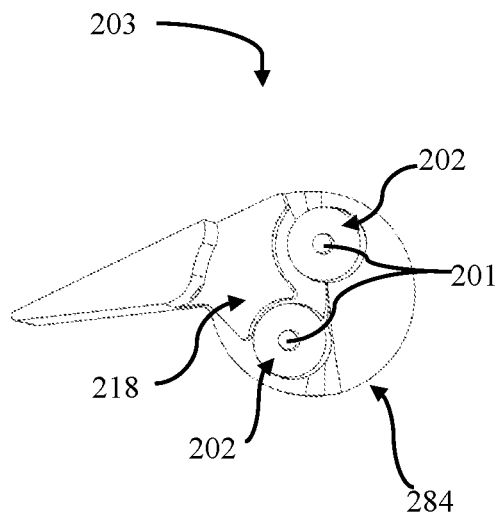
FIG. 23B shows an additional perspective view of a first jaw illustrating cable pulleys of said jaw according to one embodiment.
Figure 25A:
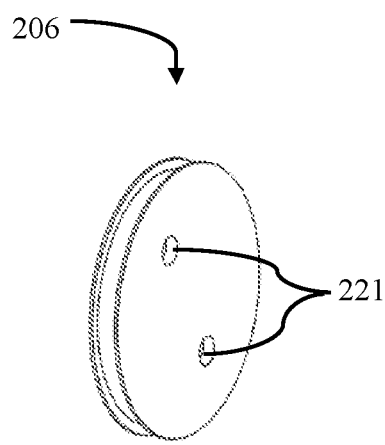
FIG. 25A shows a perspective view of a redirecting cable hub according to one embodiment.
Figure 25B:
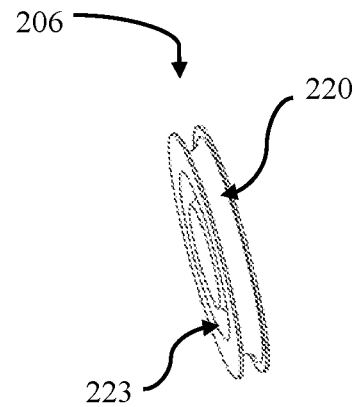
FIG. 25B shows an additional perspective view of a redirecting cable hub according to one embodiment.

In alternative embodiments, the actuation hub of the first jaw can take on a variety of configurations. FIGS. 22A-22B show an illustrative embodiment of an actuation hub with an alternative configuration. As seen in FIGS. 22A-22B, in one embodiment a first jaw 203 contains an actuation hub 284 and a working segment 283. In this embodiment, the actuation hub 283 contains a plurality of pulley pockets 204. The pulley pocket 204 is configured to allow a cable pulley 202 (FIGS. 23A-23B) to sit within. In some embodiments, protruding from the pulley pocket 204 is a fulcrum 201, which is configured to allow the cable pulley 202 to rotate about. As seen in FIGS. 23A-23B, the cable pulley 202 contains an aperture for which the fulcrum 201 passes through. In addition, the fulcrum(s) 201 are configured to mate and couple to connection apertures 221 located on a redirecting cable hub 206 (FIG. 25A). Redirecting cable hub 206 is configured to perform the same function as redirecting cable hub 106 detailed below. As seen in FIG. 25B, redirecting cable hub 206, contains a cable raceway 220 which extends around the perimeter of the redirecting cable hub 206. The redirecting cable raceway 220 provides a surface for cable 185 to ride along during actuation of the jaw assembly 101. In addition, the redirecting cable raceway 220 is configured to retain cable 185 within said raceway 220 during actuation of the jaw assembly 101, such that cable 185 does not pop and/or slip off said raceway. In addition, redirecting cable hub 206 also contains a bearing race 223 on one side, which is configured to allow a ball bearing set to sit in, and house said set. Bearing race 223 provides a surface for the redirecting cable hub 206 to rotate. In addition, bearing race 223 is configured to allow rotational motion about the axis of the redirecting cable hub, while preventing axially movement in all other axes, similar to the bearing race 123 of redirecting cable hub 106 detailed below.

Figure 24:
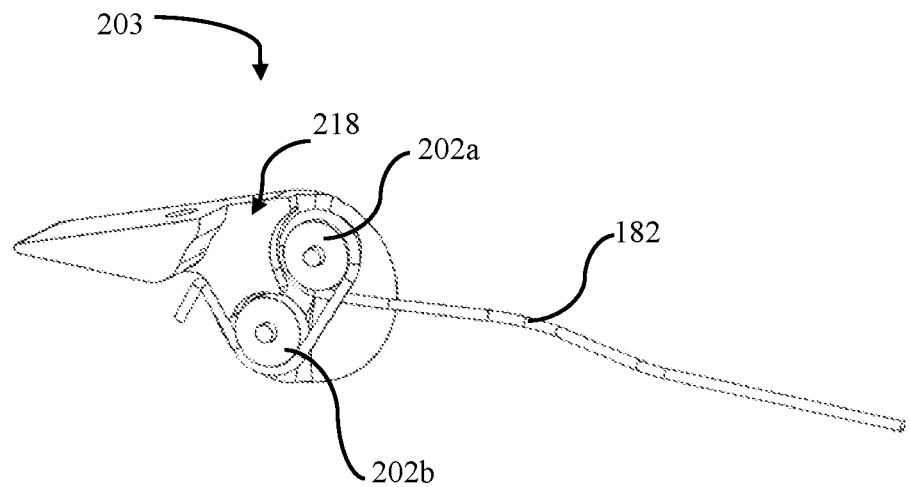
FIG. 24 shows a perspective view of cable routed to a cable pulley of a first jaw according to one embodiment.

The actuation hub 284 of the first jaw 203 also comprises a cable routing protrusion 218, which is configured to ensure that a cable being routed about the cable pulley 202 maintains contact with said pulley during actuation of the jaw assembly. The cable pulleys 202 are configured to reduce the friction imparted on the cable routed about it, so as to limit the amount of wear on the cable during actuation, as well as increase the force the first jaw 203 can apply. In addition, the cable pulley 202 reduces stick-slip which causes jerky motion thus improving the motion the first jaw 203 during actuation. As seen in FIG. 24, cable 182 is routed around a first cable pulley 202a and then about a second cable pulley 202b, with the cable routing protrusion 218 securing cable 182 such that said cable maintains contact with the first cable pulley 202a. In this embodiment, cable 182 terminates on the second jaw 104 as detailed above, such that pulling on cable 182 causes the second jaw 104 to open relative to the first jaw 203. In addition, as with the first jaw 103 detailed above, first jaw 203 contains a cable routing aperture 215 and a cable termination site 205 on the working segment 283 of the first jaw 203. Likewise, in some embodiments actuation hub 284 has two sides, with one side configured to contain the cable pulleys 202 as detailed above, and one side configured to contain a bearing race for which a ball bearing set sits and rides within, similar to actuation hub 184 detailed above. Further, as shown in FIG. 24, cable 182 wraps around cable pulleys 202. The cable wrap angles will vary depending on the placement of the cable pulleys 202 on the actuation hub 284, as well as the position of the first jaw 203 along its rotational axis. In some embodiments, the wrap angle around cable pulley 202a will vary between about 240 to 300 degrees. In other embodiments, the wrap angle around cable pulley 202a will vary between about 180 to 360 degrees. In another embodiment, the wrap angle around cable pulley 202a will vary between about 220 to 320 degrees. In another embodiment, the wrap angle around cable pulley 202a will vary between about 200 to 340 degrees. In another embodiment, the wrap angle around cable pulley 202a will vary between about 260 to 300 degrees. Meanwhile, in some embodiments, the wrap angle around cable pulley 202b will vary between 0 to 110 degrees. In other embodiments, the wrap angle around cable pulley 202b will vary between 0 to 180 degrees. In another embodiment, the wrap angle around cable pulley 202b will vary between 0 to 130 degrees. In a further embodiment, the wrap angle around cable pulley 202b will vary between 0 to 150 degrees. In still a further embodiment, the wrap angle around cable pulley 202b will vary between 0 to 150 degrees.

FIGS. 5A-5C, show multiple views of an illustrative embodiment of the redirecting cable hub 106. The redirecting cable hub 106, is configured to route cables 182 and cable 185 to their respective termination sites 110 and 105b. In one embodiment, the redirecting cable hub 106 is configured as a circular hub, which contains two sides and a redirecting cable raceway 120. As depicted in FIGS. 5A-5C, in one embodiment, the redirecting cable raceway 120 extends around the perimeter of the redirecting cable hub 106. The redirecting cable raceway 120 provides a surface for cable 185 to ride along during actuation of the jaw assembly 101. In addition, the redirecting cable raceway 120 is configured to retain cable 185 within said raceway 120 during actuation of the jaw assembly 101, such that cable 185 does not pop and/or slip off said raceway.

As detailed above, in some embodiments, situated on one side of the redirecting cable hub 106 are connection pins 122a and 122b, which are utilized to mate and couple the actuation hub 184 of the first jaw 103 with the redirecting cable hub 106. In alternative embodiments, the actuation hub 184 of the first jaw 103 and the redirecting cable hub 106 are fabricated to be one piece. In some embodiments, connection pins 122a and 122b are configured to be cylindrical in shape having a smooth surface, so as to allow a cable to be routed about said pin, while in other embodiments the connection pins 122a and 122b can be configured as any shape having a smooth surface and edges, including but not limited to oval, triangle with rounded edges and/or other more complex shapes or channels capable of routing cables.

In some embodiments, only one connection pin is found on the redirecting cable hub 106, while in other embodiments, a plurality of connection pins may be located on the redirecting cable hub 106. As mentioned above, in some embodiments, connection pin 122a provides a routing surface for cable 182 to direct said cable to the cable routing aperture 114 located on the second jaw 104. In these embodiments, connection pin 122a is configured such that cable 182 maintains contact with the cable routing pin 118, so that said cable wraps around cable routing protrusion 119a when the jaw assembly 101 is actuated in a first direction and around cable routing protrusion 119b when the jaw assembly 101 is actuated in a second direction. Additionally, in some embodiments, located on one side of the redirecting cable hub 106 is a cable routing pin aperture 121. In these embodiments, the cable routing pin aperture 121 is configured to allow the cable routing pin 118 located on the actuation hub 184 of the first jaw 103 to enter said aperture, thus coupling and mating actuation hub 184 and the redirecting cable hub 106. In addition, the coupling and mating of the cable routing pin 118 with the cable routing pin aperture 121, fashions a connection such that cable 182 maintains contact with the cable routing pin 118 during actuation of the jaw assembly 101 and prevent wedging and/or jamming of said cable.

As seen in FIG. 5B and FIG. 5C, in some embodiments, located on one side of the redirecting cable hub 106, is a bearing race 123. In these embodiments, bearing race 123 is configured to allow one of the pluralities of ball bearing sets 109 (FIG. 2B) to sit in, and house said set. Bearing race 123 provides a surface for the redirecting cable hub 106 to rotate. In addition, bearing race 123 is configured to allow rotational motion about the redirecting cable hub axis, while preventing axially movement in all other axes. Certain embodiments of the technology do not require ball bearings. Certain embodiments comprise bushings, sleeve bearings, axle and/or other rolling element bearings known in the art.

As shown in FIG. 2B and FIG. 2D, the redirecting cable hub 106 is situated in between the actuation hub 184 of the first jaw 103 and the actuation hub 180 of the second jaw 104. As detailed above, one side of the redirecting cable hub 106 couples and mates with the actuation hub 184 of the first jaw 103, with the other side of the actuation hub 184 containing bearing race 123 (FIG. 5B). The bearing race 123 of the redirecting cable hub 106 is configured to have the same dimensions as the bearing race 113 located on the actuation hub 180 of the second jaw 104, so that when the actuation hub 180 of the second jaw 104 contacts the redirecting cable hub 106, said contact fashions a housing for one of the plurality of ball bearing sets 109 such that said ball bearing set sits and rides along both bearing race 113 and bearing race 123. In alternative embodiments, bearing race 123 and bearing race 113 are not symmetric, or the same size, while in other embodiments bearing race 123 and bearing race 113 are substituted for axle.

Figure 6A:
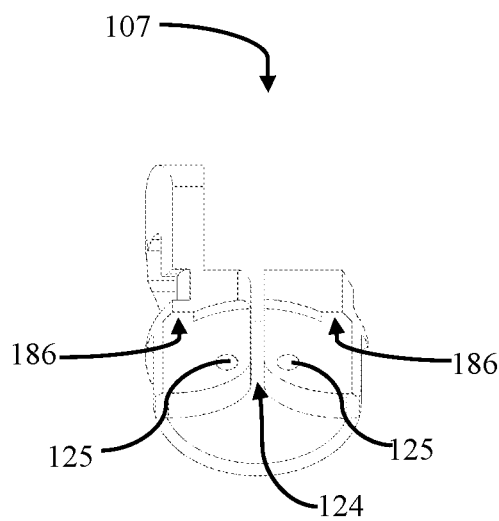
FIG. 6A is a rear perspective view of a hinge flex body according to one embodiment.
Figure 6B:
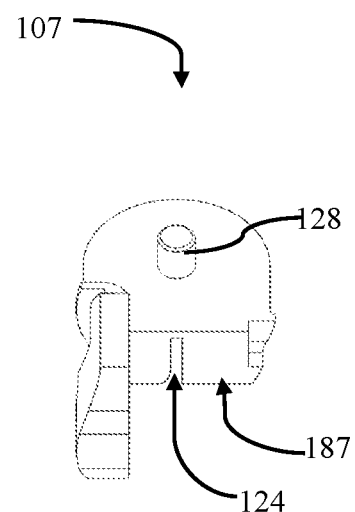
FIG. 6B is a front perspective view of a hinge flex body according to one embodiment.

As detailed above, in some embodiments located on one side of the actuation hub 184 of the first jaw 103, as well as on one side of the actuation hub 180 of the second jaw 104 are bearing races 116a and 116b respectively. Both bearing races 116a and 116b are configured to allow one of the pluralities of ball bearing sets 109 to ride on. In some embodiments, bearing races 116a and 116b are both configured to mate with a hinge bearing race 127, with bearing race 116a mating with the hinge bearing race 127 located on the hinge non-flex body 108 (FIG. 7B), and bearing race 116b mating with the hinge bearing race 127 located on the hinge flex body 107 (FIG. 6B). The mating between bearing race 116a and the hinge bearing race 127 of the hinge non-flex body 108 form a housing for one of the pluralities of ball bearing sets 109, with bearing race 116a functioning as an inner bearing race and the hinge bearing race 127 of the hinge non-flex body 108 functioning as an outer bearing race. Similarly, the mating between the bearing race 116*b* and the hinge bearing race 127 of the hinge flex body 107 form a housing for another one of the pluralities of ball bearing sets 109. The mating of the aforementioned bearing races, allows the jaw assembly 101 to rotate about the pitch axis 189 (FIG. 18), as detailed below.

In one embodiment, the hinge flex body 107 and the hinge non-flex body 108 function as a housing for the first jaw 103, the second jaw 104, the redirecting cable hub 106, as well as some of the plurality of ball bearing sets 109. FIGS. 6A-6D show multiple views of an illustrative embodiment of the hinge flex body 107. FIGS. 7A-7D show multiple views of an illustrative embodiment of the hinge non-flex body 108.

As shown in FIGS. 6A-6D in one embodiment, the hinge flex body 107 contains a proximal and distal end, with said ends comprising inner and outer surfaces. In one embodiment, situated on the inner surface of the distal end of the hinge flex body 107 is the hinge bearing race 127, which is configured to mate and couple with bearing race 116*b* of the first jaw 103 as detailed above. In addition to functioning as a housing for one of the pluralities of ball bearing sets 109 as detailed above, the mating between bearing race 116*b* of the first jaw 103 and the hinge bearing race 127 of the hinge flex body 107 also prevents the first jaw 103 from experiencing any transitional movement during actuation of said first jaw. Furthermore, the aforementioned mating also defines a jaw axis 189 (FIG. 17A and FIG. 17C) for which the first jaw 103 rotates about. In addition, in some embodiments, the distal end of the hinge flex body 107 contains a magnet housing aperture 190 which is configured to allow the magnet housing 112*b* of the first jaw 103 to enter and mate with.

In some embodiments, on the outer surface of the distal end of the hinge flex body 107 is a flex pocket 126. The flex pocket 126 is configured to allow an electrical communication component to sit within, so as to prevent any damage to said component during actuation of the jaw assembly 101. In various embodiments, different electrical communication components are utilized, including but not limited to rigid flexible printed circuit boards (RFPCB), flexible printed circuit board (FPCB), and/or any other type of electrical communication component known in the art. Electrical communication components which sit in the flex pocket 126 of the hinge flex body 107 are utilized to transmit position and/or orientation data of the first jaw 103, to a central computer which processes said data and transmits control commands and/or prompts to actuators which actuate and manipulate the first jaw 103. The position and/or orientation data of the first jaw 103 is obtained from magnet(s) located in magnet housing 112*b*, as well as sensors situated in the flex pocket 126 of the hinge flex body 107. In these embodiments, in addition to housing electrical communication components, the flex pocket 126 of the hinge flex body 107 contains sensors for sensing the change in magnetic field of the magnet(s) in magnet housing 112*b* as the first jaw 103 is rotated about the jaw axis 189. In some embodiments, two rotational position sensors are found in the flex pocket 126 of the hinge flex body 107 for sensing the change in magnetic field, while in other embodiments four rotational position sensors are found. The magnet sensing is further detailed below.

Figure 17A:
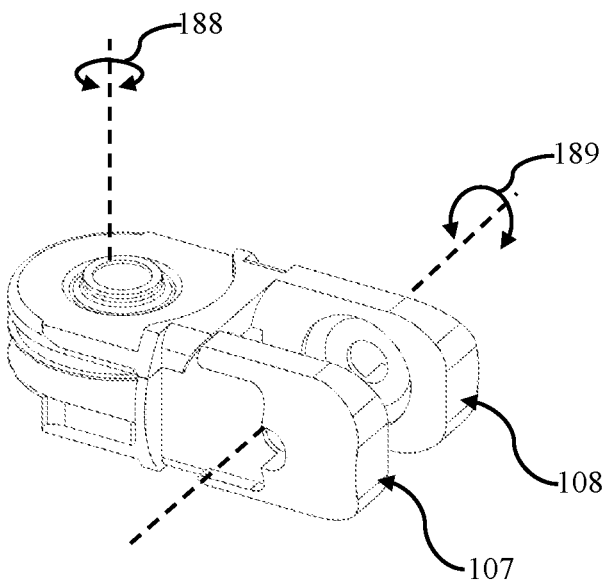
FIG. 17A is perspective view illustrating pivot axes formed by mating a hinge flex body and a hinge non-flex body according to one embodiment.
Figure 17B:
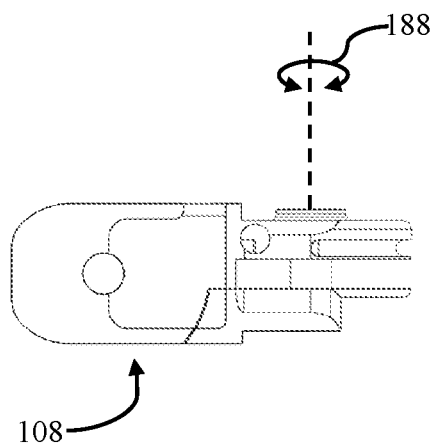
FIG. 17B is a side profile view of a hinge non-flex body illustrating a pivot axis of the wrist assembly of FIGS. 1A-1E according to one embodiment.

As mentioned above, in some embodiments the hinge flex body 107 contains a proximal end. The proximal end of the hinge flex body 107 is utilized to couple and mate the jaw assembly 101 with the hinge-rotary assembly 102, as well as defines a pitch axis 188 (FIG. 17A and FIG. 17B). As shown in FIG. 6A, in some embodiments the proximal end of the hinge flex body 107 is constructed to have two sides an interior and exterior side. In one embodiment, the exterior side contains a flex slot 124 which is configured to route an electrical communication component to the flex pocket 126 located on the outer surface of the distal end of the hinge flex body 107. The flex slot 124 is configured to allow an electrical communication component to sit within the slot, such that said component does not excessively bend and/or become damaged during actuation of the wrist assembly 100. In some embodiments, the flex slot 124 is located on the interior side of the proximal end of the hinge flex body, with the electrical communication components routed to the flex pocket 126, as detailed above. In these embodiments, the exterior side of the proximal end of the hinge flex body contains a bearing surface, thus eliminating the male bearing race 138 as detailed below. In addition, in these embodiments fulcrum 128 is relocated to the interior side of the proximal end of the hinge non-flex body 108.

Figure 6C:
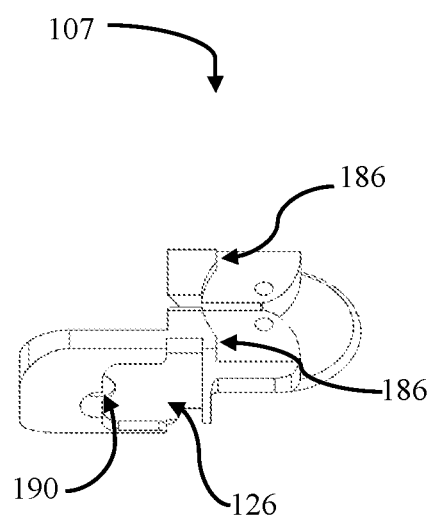
FIG. 6C is a side perspective view of a hinge flex body according to one embodiment.

In addition, in some embodiments, the exterior side of the proximal end of the hinge flex body 107 contains a hinge hard stop 186. In these embodiments, the hinge hard stops 186 is configured to constrain the jaw assembly 101 from rotating about the pitch axis 188 (FIG. 17A) past an allowable limit of articulation. In some embodiments, the allowable limit of articulation is 120 degrees, having 60 degrees of motion in either direction, while in other embodiments the allowable limit of articulation is increased and/or decreased. As seen in FIG. 6A and FIG. 6C, the hinge hard stops 186 are configured as extruded surfaces that make contact with the distal end of the hinge-rotary assembly 102 to prevent the jaw assembly 101 from being actuated past an allowable degree of rotation. The proximal end of the hinge flex body 107 is configured to be circular in shape, so as to allow the hinge-rotary assembly 102 to rotate about the pitch axis 188 during actuation.

Figure 6D:
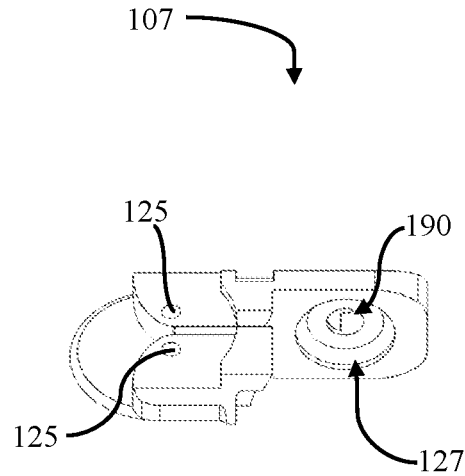
FIG. 6D is an additional side perspective view of a hinge flex body according to one embodiment.

As shown in FIGS. 6A and 6D, in some embodiments the exterior side of the proximal end of the hinge flex body 107 contains connection apertures 125. The connection apertures 125 are configured to allow a male bearing race 138 (FIGS. 15A-15D) from the hinge-rotary assembly 102 to mate and couple to. In some embodiments, the connection apertures 125 are situated on a protruded surface above the flex slot 124, such that electrical communication components can be routed through said slot without any interference from the male bearing race 138. In some embodiments, the connection apertures 125 are eliminated, with the male bearing race 138 fabricated to be a part of the proximal end of the hinge flex body 107.

In some embodiments, on the interior side of the proximal end of the hinge flex body 107 is a fulcrum 128, which protrudes from the hinge flex body 107. As depicted in the illustrative embodiment shown in FIG. 6B, the fulcrum 128 is configured to be cylindrical in shape, having an outer diameter that allows the fulcrum 128 to pass through an aperture on an idler pulley 137 (FIG. 16A). In some embodiments, the fulcrum 128 is substituted for a bearing or any axle known in the art. In addition, in some embodiments the proximal end of the hinge flex body 107 contains a jaw hard stop 187. In these embodiments, the jaw hard stop 187 is configured to constrain the first jaw 103 and the second jaw 104 from rotating about the jaw axis 189 (FIG. 17A and FIG. 17C) past an allowable limit of articulation. As seen in FIG. 6B, the jaw hard stop 187 is configured as an extruded surface that makes contact with the proximal end of the first and second jaw to prevent said jaws from being actuated past an allowable degree of rotation. In some embodiments, the allowable degree of rotation is 93 degrees in either direction, while in other embodiments the allowable degree of rotation is less than or more than 93 degrees of rotation in either direction.

Figure 17C:
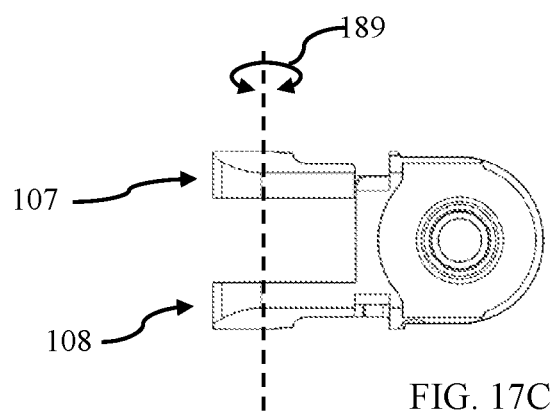
FIG. 17C is a top profile view of the coupling between a hinge flex body and a hinge non-flex body illustrating a pivot axis of the wrist assembly of FIGS. 1A-1E according to one embodiment.

As mentioned above, in some embodiments the hinge flex body 107 and the hinge non-flex body 108 function as a housing for the first jaw 103 and the second jaw 104, along with other components of the jaw assembly 101. FIGS. 7A-7D show multiple views of an illustrative embodiment of a hinge non-flex body 108. As shown in FIGS. 7A-7D, in one embodiment, the hinge non-flex body 108 is fabricated to contain a proximal and distal end. The proximal and distal ends of the hinge non-flex body 108 are configured to have approximately the same architecture as the distal and proximal ends of the hinge flex body 107, such that the connection between the hinge flex body 107 and hinge non-flex body 108 is seamless, with the outer profiles of both bodies being flush with one another (FIGS. 17A-17C).

Figure 7A:
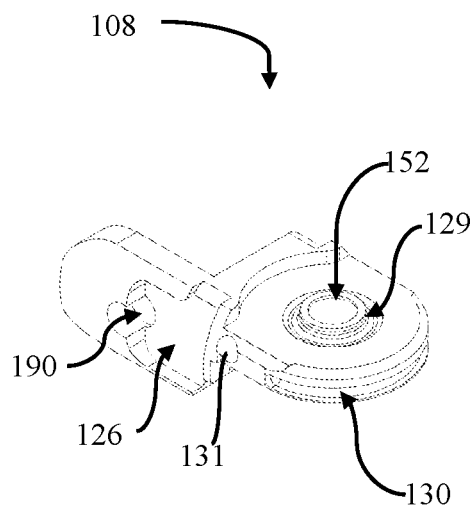
FIG. 7A is an isometric view of a hinge non-flex body according to one embodiment.

As depicted in FIG. 7A, in one embodiment the distal end of the hinge non-flex body 108 is configured to have an inner and outer surface. In one embodiment, located on the inner surface of the distal end of the hinge non-flex body 108 is the hinge bearing race 127, which is configured to mate and couple with bearing race 116a of the second jaw 104 as detailed above. In addition to functioning as a housing for one of the pluralities of ball bearing sets 109, the mating between bearing race 116a of the second jaw 104 and the hinge bearing race 127 of the hinge non-flex body 108 also prevents the second jaw 104 from experiencing any transitional movement during actuation of said second jaw. Furthermore, the aforementioned mating also defines a jaw axis 189 (FIG. 17A and FIG. 17C) for which the second jaw 104 rotates about. In addition, in some embodiments, the distal end of the hinge non-flex body 108 contains a magnet housing aperture 190 which is configured to allow the magnet housing 112a of the second jaw 104 to enter and mate with.

In some embodiments, on the outer surface of the distal end of the hinge non-flex body 108 is a flex pocket 126. The flex pocket 126 is configured to allow an electrical communication component to sit within, so as to prevent any damage to said component during actuation of the jaw assembly 101. In various embodiment, different electrical communication components are utilized, including but not limited to rigid flexible printed circuit boards (RFPCB), flexible printed circuit board (FPCB), and/or any other type of electrical communication component known in the art. Electrical communication components situated in the flex pocket 126 of the hinge non-flex body 108 are utilized to transmit position and/or orientation data of the second jaw 104 to a central computer which processes said data and transmits control commands and/or prompts to actuators which actuate and manipulate the second jaw 104. The position and/or orientation data of the second jaw 104 is obtained from magnet(s) located in magnet housing 112a, as well as sensors contained in the flex pocket 126 of the hinge non-flex body 108 and the jaw assembly 101. In these embodiments, in addition to housing electrical communication components, the flex pocket 126 of the hinge non-flex body 108 contains sensors for sensing the change in magnetic field of the magnet(s) in magnet housing 112b, as the second jaw 104 is rotated about the jaw axis 189. In some embodiments, two rotational position sensors are found in the flex pocket 126 of the hinge non-flex body 108 for sensing the change in magnetic field, while in other embodiments four rotational position sensors are found. The magnet sensing is further detailed below.

Figure 10A:
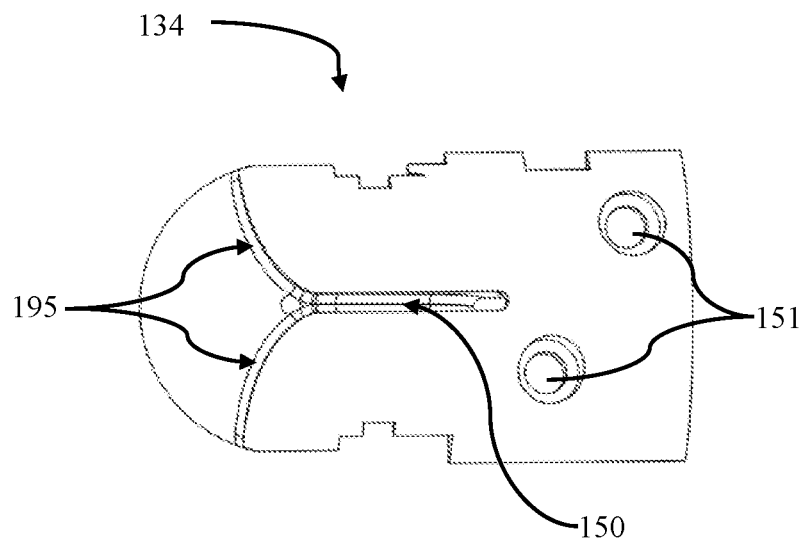
FIG. 10A is a side profile view of a female hinge body according to one embodiment.

As mentioned above, in some embodiments the hinge non-flex body 108 contains a proximal end. The proximal end of the hinge non-flex body 108 is utilized in conjunction with the proximal end of the hinge flex body 107 to couple and mate the jaw assembly 101 (FIG. 1D) with the hinge-rotary assembly 102 (FIG. 1D), with said mating and coupling defining the pitch axis 188 (FIG. 17A and FIG. 17B). As shown in FIGS. 7A-7D, in some embodiments the proximal end of the hinge non-flex body 108 is constructed to have two sides, with one side containing a hinge bearing race 129. The hinge bearing race 129 is configured to allow one of the plurality of ball bearing sets 109 to sit in, and ride along said race during actuation of the jaw assembly 101. The ball bearing set 109 which sits in the hinge bearing race 129 of the hinge non-flex body 108 also sits within a bearing race 147 (FIG. 10B) of a female hinge body 134 (FIG. 10A). Additionally, in some embodiments, the proximal end of the hinge non-flex body 108 contains a magnet pocket 152. In these embodiments, the magnet pocket 152 is configured allow a magnet and/or a plurality of magnets to sit in. As further detailed below, the magnet is utilized along with sensors located on the hinge-rotary assembly 102 to obtain position data and in some embodiments, orientation data of the jaw assembly 101 as said jaw assembly is rotated about the pitch axis 188.

In addition, in some embodiments, the outer surface of the proximal end of the hinge non-flex body 108 is fabricated to contain a cable raceway 130. The cable raceway 130 is configured to route cable 191 through a cable termination channel 132 situated on one side of the proximal end of the hinge non-flex body 108. The cable termination channel 132 is configured to route cable 191 to a cable termination site 131 located on the proximal end of the hinge non-flex body 108. In different embodiments, various methods and/or techniques as detailed above, are utilized to terminate cable 191 in the cable termination site 131.

Figure 7B:
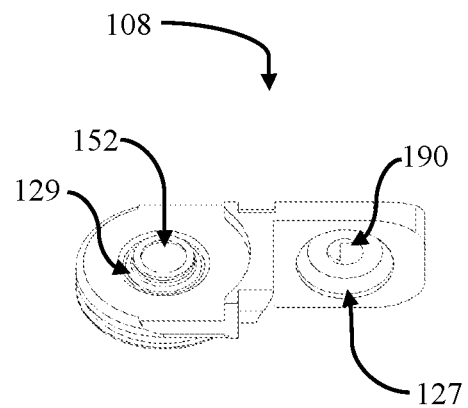
FIG. 7B is side perspective view of a hinge non-flex body according to one embodiment.
Figure 7C:
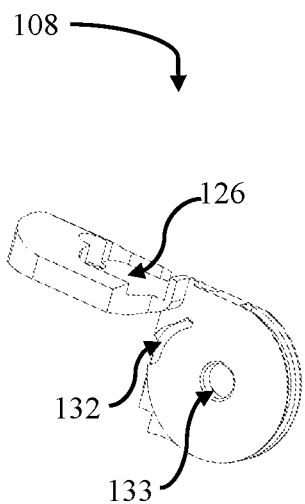
FIG. 7C is a side isometric view of a hinge non-flex body according to one embodiment.
Figure 7D:
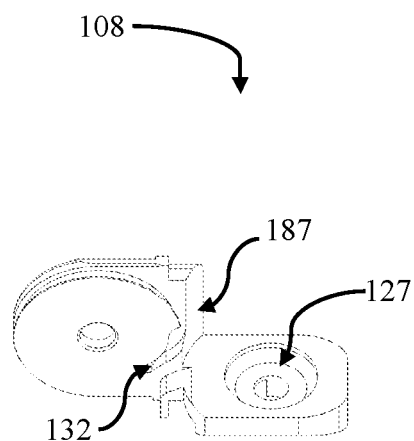
FIG. 7D is a side perspective view of a hinge non-flex body according to one embodiment.

Additionally, in some embodiments, one side of the proximal end of the hinge non-flex body 108 contains a fulcrum aperture 133 (FIG. 7C). In these embodiments, the fulcrum aperture 133 is configured to allow the fulcrum 128 of the hinge flex body 107 to enter and sit within said aperture. Furthermore, in some embodiments, the proximal end of the hinge non-flex body 108 contains a jaw hard stop 187. In these embodiments, the jaw hard stop 187 is configured to is constrain the first jaw 103 and/or the second jaw 104 from rotating about the jaw axis 189 (FIG. 17A and FIG. 17C) past an allowable limit of articulation. As seen in FIG. 7D, the jaw hard stop 187 is configured as an extruded surface that makes contact with the proximal end of the first and/or second jaw to prevent said jaws from being actuated past an allowable degree of rotation. In some embodiments, the allowable degree of rotation is 93 degrees in either direction, while in other embodiments the allowable degree of rotation is less than or more than 93 degrees of rotation in either direction.

Figure 8A:
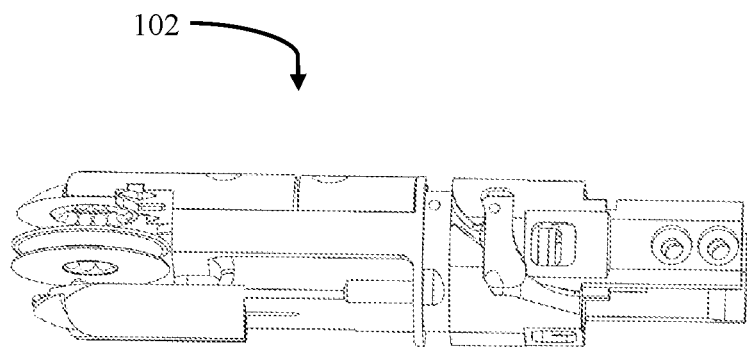
FIG. 8A is a top isometric view of a hinge rotary assembly according to one embodiment.
Figure 8B:
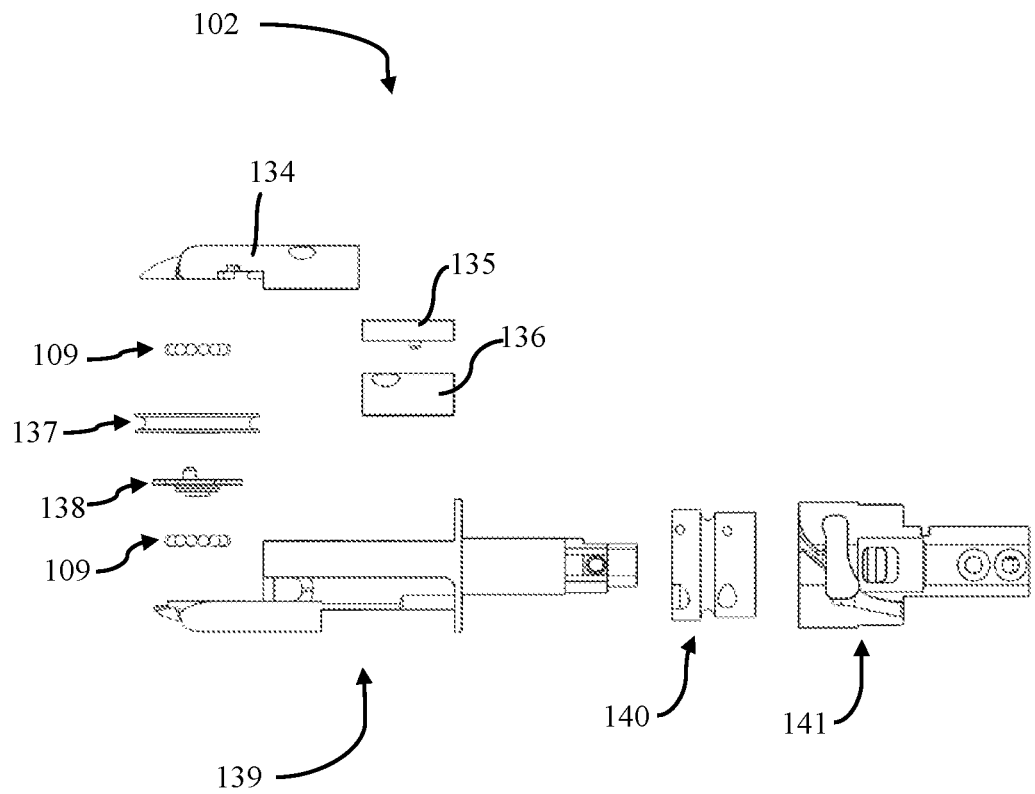
FIG. 8B is an exploded top profile view of a hinge rotary assembly according to one embodiment.
Figure 18:
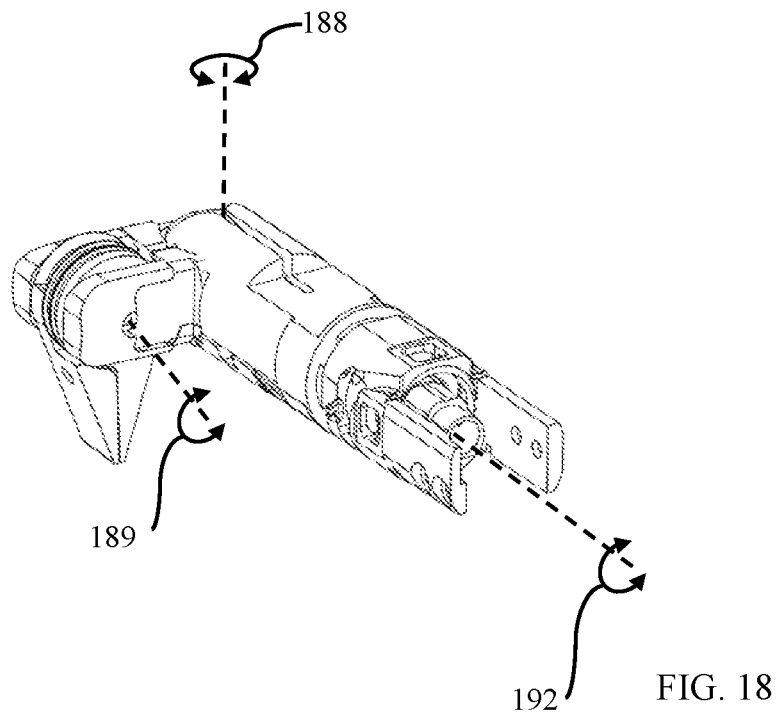
FIG. 18 shows a perspective view of the pivot axes of a wrist assembly according to one embodiment.

As mentioned above, the proximal ends of both the hinge flex body 107 and the hinge non-flex body 108, couple the jaw assembly 101 to the hinge-rotary assembly 102. FIG. 8A shows an isometric view of an illustrative embodiment of the hinge-rotary assembly 102. FIG. 8B shows an exploded top view of an illustrative embodiment of the hinge-rotary assembly 102. The hinge-rotary assembly 102, is configured to provide two (2) additional DOFs, to the wrist assembly 100. The hinge-rotary assembly 102 in conjunction with the hinge flex body 107 and the hinge non-flex body 108 is configured to provide one DOF, with said DOF being rotation of the jaw assembly 101 about the pitch axis 188 (FIG. 17A). In addition, the hinge-rotary assembly 102 is also configured to provide another DOF, with this DOF being the rotation of the wrist assembly 100 about a roll axis 192 (FIG. 18). Furthermore, in addition to providing two extra DOFs, the hinge-rotary assembly 102 also functions as an intermediary, connecting the electrical communication components of the jaw assembly 101, with electrical communication components of the rest of the robotic arm, so as to allow the data obtained from sensors on the jaw assembly 101 to be transmitted from said assembly, through the hinge-rotary assembly 102 to a central computer, as well as to allow data to be transmitted from the central computer back to the jaw assembly 101.

Figure 9A:
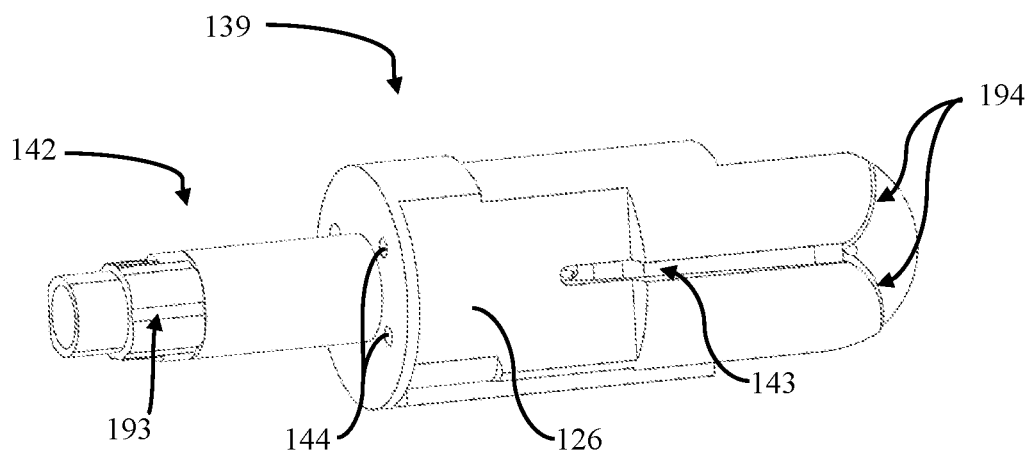
FIG. 9A is an isometric view of a male rotary-hinge body according to one embodiment.
Figure 9B:
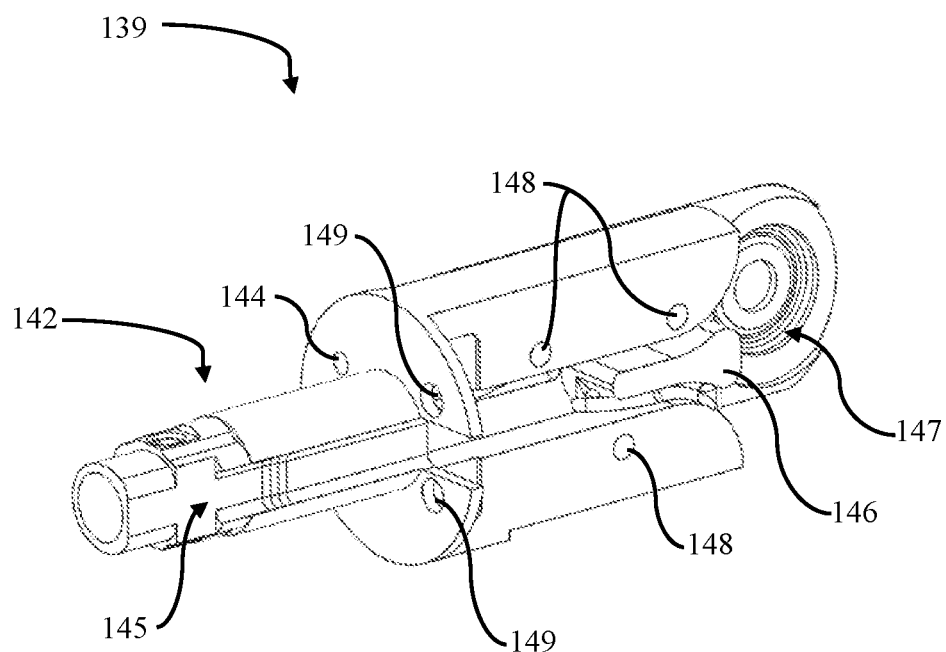
FIG. 9B is an additional isometric view of a male rotary-hinge body according to one embodiment.

As depicted in the illustrative embodiment shown in FIG. 8B, the hinge-rotary assembly 102 contains a female hinge body, also referred to as a hinge cover 134 and a male rotary-hinge body, also referred to as a hinge-rotary body 139. The female hinge body 134 along with the male rotary-hinge body 139 are fabricated to function as a housing for various components of the hinge-rotary assembly 102, as well as a connection and mating point for the proximal ends of the hinge flex body 107 and hinge non-flex body 108. FIG. 9A and FIG. 9B show multiple views of an illustrative embodiment of a male rotary-hinge body 139. As seen in FIGS. 9A-9B, the male rotary-hinge body 139 contains a distal and proximal end, as well as outer and inner surfaces.

As depicted in FIGS. 9A-9B, the proximal end of the male rotary-hinge body, also referred to as hinge-rotary body 139 contains a cable conduit 142. In some embodiments, the cable conduit 142 is fabricated as a cylindrical shaft, having an aperture for which cables 181, 182, 185, and 191 (not shown in FIG. 9A) are routed through. The cable conduit 142 is configured to allow the aforementioned cables to be routed through said conduit, such that when the wrist assembly 100 is rotated about the roll axis 192, the cables do not become tangled with one another. In some embodiments, located on the outer surface of the cable conduit 142 is a bearing interface 193, on which a bearing (not shown) sits, said bearing is configured to allow for rotation of the cable conduit 142 through a variety of loading conditions.

As shown in FIG. 9B, in some embodiments, located on the inner surface of the cable conduit 142 is a flex guide surface 145. In these embodiments, the flex guide surface 145 is configured to be a flat surface for which an electrical communication component(s) rests on. The flex guide surface 145 is also configured to route and guide electrical communication component(s) from a robotic arm through the proximal end of the hinge-rotary assembly 102, where said component(s) operatively connect to other electrical communication component(s) that are routed from the jaw assembly 101 through the distal end of the hinge-rotary assembly 102. The flex guide surface 145 is fabricated so electrical communication component(s) sits flat against said surface, such that during actuation of the wrist assembly 100 said component(s) are not bent and/or damaged. In alternative embodiments, electrical communication is transmitted through the cable conduit 142 via standard electrical communication wires and/or cables known in the art, including but not limited to copper cables and/or fiber optic cables.

In addition, the cable conduit 142 is configured to allow a rotary pulley body 140 to connect and mate with the male rotary-hinge body 139. In some embodiments, the rotary pulley body 140 is fabricated to have an opening in its center to allow the cable conduit 142 to pass through. In these embodiments, the rotary pulley body 140 connects and mates with the male rotary-hinge body 139 via a screw connection, with screws passing through through-holes 149, and entering tapped holes 168 (FIG. 13B), on the rotary pulley body 140. In addition, the rotary pulley body 140 is coupled to the male rotary-hinge body 139 via a pin connection, with pins entering and sitting with pin connection apertures 144 located on both the male rotary-hinge body 139 and the rotary pulley body 140. The pin connection is configured to constrain the rotary pulley body 140 to the male rotary-hinge body 139 such that the rotary pulley body 140 does not rotate during actuation of the wrist assembly 100 about the roll axis 192. In alternative embodiments, the rotary pulley body 140 is fabricated as part of the male rotary-hinge body 139, thus eliminating the connections described above.

As mentioned above, the male rotary-hinge body 139 is configured to have a distal end having an inner and outer surface. As depicted in FIG. 9A, in some embodiments, located on the outer surface of the distal end of the male rotary-hinge body 139 is a cable guide slot 143. Cable guide slot 143 is configured to route and guide cable 181 from the hinge-rotary assembly 102 through the proximal end of the jaw assembly 101 to the cable routing raceway 111 (FIG. 3A) located on the actuation hub 180 of the second jaw 104. In these embodiments, cable 181 is routed through the cable conduit 142 to the inner surface of the distal end of the male rotary-hinge body 139, where said cable passes through an aperture and enters the cable guide slot 143 on the outer surface of the distal end of the male rotary-hinge body 139. As the cables reach the end of the cable guide slot 143, the cables are routed along decoupling surfaces 194. Decoupling surfaces may be configured to decouple cable motion from joint motion, to decouple joint motion from cable motion, or to decouple cable motion from joint motion and decouple joint motion from cable motion. The decoupling surfaces are fabricated to be curved in shape, such that when the first and second jaws rotate, the cables that close the jaws pivot about the center of the pitch axis 188 without changing length. The curve of the decoupling surfaces 194 allow the cables to wrap along it such that the cables neither lose tension or become over tensioned, as there is no sliding motion between the cable and the surface. In addition, the decoupling surfaces effectuate decoupled motion of the jaws when rotated about the jaw axis 189 and the jaw assembly when rotated about the pitch axis.

In some embodiments, also located on the outer surface of the distal end of the male rotary-hinge body 139 is a flex pocket 126. As detailed above, the flex pocket 126 is configured to allow an electrical communication component(s) to sit within and mount to said pocket, so as to prevent any damage to said component(s) during actuation of the wrist assembly 100. In various embodiments, different electrical communication components are utilized, including but not limited to rigid flexible printed circuit boards (RFPCB), flexible printed circuit boards (FPCB), and/or any other type(s) of electrical communication components known in the art.

As shown in FIG. 9B, in some embodiments, the inner surface of the distal end of the male rotary-hinge body 139 contains a cable routing protrusion 146. The cable routing protrusion 146 is configured to direct cables routed through the distal end of the hinge-rotary assembly 102 to a desired location. In one embodiment, the cable routing protrusion 146 is fabricated to be a smooth surface so that cables are not damaged during actuation. In addition, the cable routing protrusion is configured to function as a divider, so that the cables that are routed through the distal end of the male rotary-hinge body 139 do not become tangled or intertwined with each other, as well as to prevent said cables from catching or hooking on to another component of the wrist assembly 100 as said cables are routed to a desired location.

In one embodiment, the cable routing protrusion 146 is configured to have two sides, with one side routing one cable to a desired location, and the other side routing a different cable to a desired location. In one embodiment, the cable routing protrusion 146 is utilized to route cable 191 (FIG. 19B) and cable 182 (FIG. 19B), with cable 191 being routed on one side of the cable routing protrusion 146 and cable 182 being routed on the other side of the cable routing protrusion 146. In this embodiment, cable 191 is routed through the distal end of the male rotary-hinge body 139 to cable raceway 130 located at the proximal end of the hinge non-flex body 108, and cable 182 is routed through the distal end of the male rotary-hinge body 139 to an idler cable raceway 178 located on the idler pulley 137 (FIGS. 16A-16B), as further detailed below. In alternative embodiments, the cable routing protrusion 146 is eliminated and replace by channels and/or conduits that direct cables to a desired location.

In some embodiments, the inner surface of the distal end of the male rotary-hinge body 139 contains a plurality of tapped holes 148. In these embodiments, the tapped holes 148 are configured to allow a screw to enter, thus mating and coupling the female hinge body 134 with the male rotary-hinge body 139, as detailed below. In addition, in these embodiments, one or more of the plurality of tapped holes 148 are utilized to mate and couple a bottom flex cover 136 (FIG. 8B and FIGS. 11A-11B) to the male rotary-hinge body 139.

In addition, in some embodiments, the inner surface of the distal end of the male rotary-hinge body 139 comprises a bearing race 147 (FIG. 9B). The bearing race 147 is configured to allow one of the pluralities of ball bearing sets 109 to sit within, and ride along during articulation of the wrist assembly 100. In these embodiments, the one of the pluralities of ball bearing sets 109 (FIG. 8B) that sits within the bearing race 147 of the male rotary-hinge body 139, also sits on a bearing raceway 175 (FIG. 15A) located on the male bearing race 138 (FIG. 15A). In these embodiments, the male bearing race 138 is configured to couple to the bearing race 147 of the distal end of the male rotary-hinge body 139, as well as with the proximal end of the hinge flex body 107.

Figure 11A:
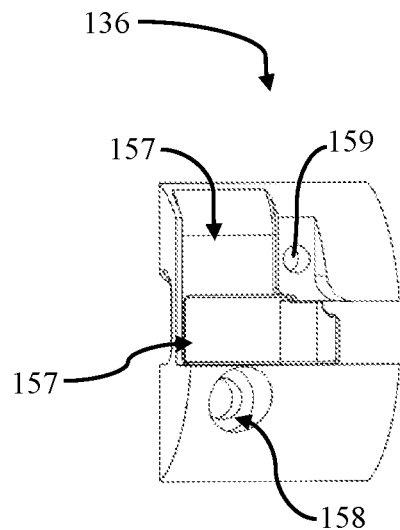
FIG. 11A is an isometric view of a bottom flex cover according to one embodiment.
Figure 11B:
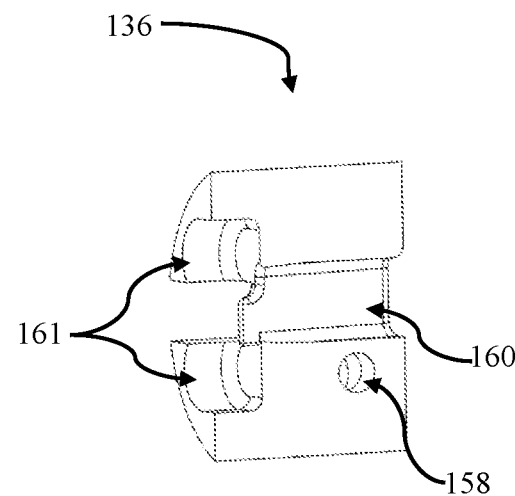
FIG. 11B is an additional isometric view of a bottom flex cover according to one embodiment.

As mentioned above, in some embodiments, the hinge-rotary assembly has a top flex cover 135 and a bottom flex cover 136 (FIGS. 11A-11B and FIGS. 12A-12B). In these embodiments, the bottom flex cover is fabricated to have an inner and outer surface. As depicted in the illustrative embodiment shown in FIG. 11B, the inner surface of the bottom flex cover 136 is a cable routing passage 160 which is utilized for cables from the proximal end of the hinge-rotary assembly to pass through. As shown in FIG. 11A, in some embodiments the outer surface of the bottom flex cover 136 has a flex pocket 157 for which electrical communication components from the jaw assembly, as well as from the hinge-rotary assembly sit. Flex pocket 157 is configured to allow the electrical communication components to sit flat in said pocket. In addition, in some embodiments the outer surface of bottom flex cover 136 has a through-hole 158 which is configured to let a screw to pass through and enter a tapped hole 148 (FIG. 9B) on the male rotary-hinge body 139. Additionally, located on the proximal end of the bottom flex cover 136 are screw cut-outs 161, which are configured to allow the head of a screw to sit in.

Figure 12A:
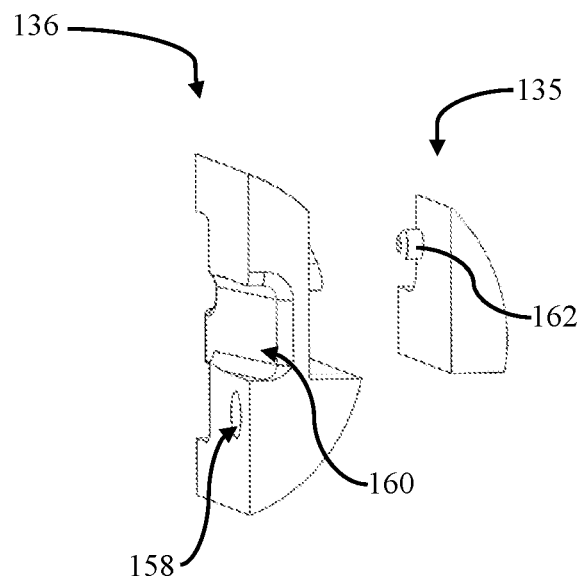
FIG. 12A is an isometric view of a top flex cover prior to mating with a bottom flex cover according to one embodiment.
Figure 12B:
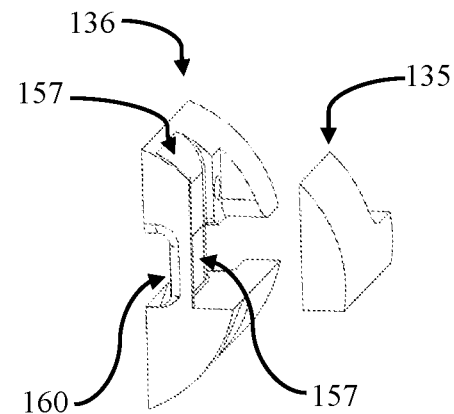
FIG. 12B is an additional isometric view of a top flex cover prior to mating with a bottom flex cover according to one embodiment.

In these embodiments, the screws that sit within the screw cut-outs 161 are used to mate male-rotary-hinge body 139 and the rotary pulley body 140 (FIGS. 13A-13D). Furthermore, in some embodiments, situated on the outer surface of the bottom flex cover, is a connection aperture 159 which is configured to allow a connection nub 162 on the top flex cover 135 to enter and thus mate the top and bottom flex covers. The connection between the top flex cover 135 and bottom flex cover 136 is depicted in FIGS. 12A-12B, according to some embodiments. In these embodiments, the top flex cover 135 is configured to mate with the bottom flex cover 136 and thus protect the electrical communication components which are situated in the flex pocket 157 of the bottom flex cover 136. In alternative embodiments, the top and bottom flex covers are fabricated as part of the female hinge body or hinge cover 134.

FIGS. 15A-15B show multiple views of an illustrative embodiment of a male bearing race 138. As shown in FIGS. 15A-15B, in one embodiment, the male bearing race 138 is fabricated to have two sides, with one side containing the bearing raceway 175, and the other side containing a plurality of male bearing connection nubs 176. As detailed above, the bearing raceway 175 is configured to allow one of the pluralities of ball bearing sets 109 to sit within and ride along said raceway, as well as sit within and ride along the bearing race 147 located on the male rotary-hinge body 139. In these embodiments, the plurality of male bearing connection nubs 176 are configured to enter and mate with the connection apertures 125 (FIG. 6A) of the hinge flex body 107. This connection, in conjunction with the connection of the hinge bearing race 129 of the hinge non-flex body 108 and a bearing race 147 (FIG. 10B) located on a female hinge body 134 (FIG. 10A), allow the jaw assembly 101 to rotate about the pitch axis 188. In alternative embodiments, the male bearing race 138 is fabricated as part of the hinge flex body 107.

Figure 10B:
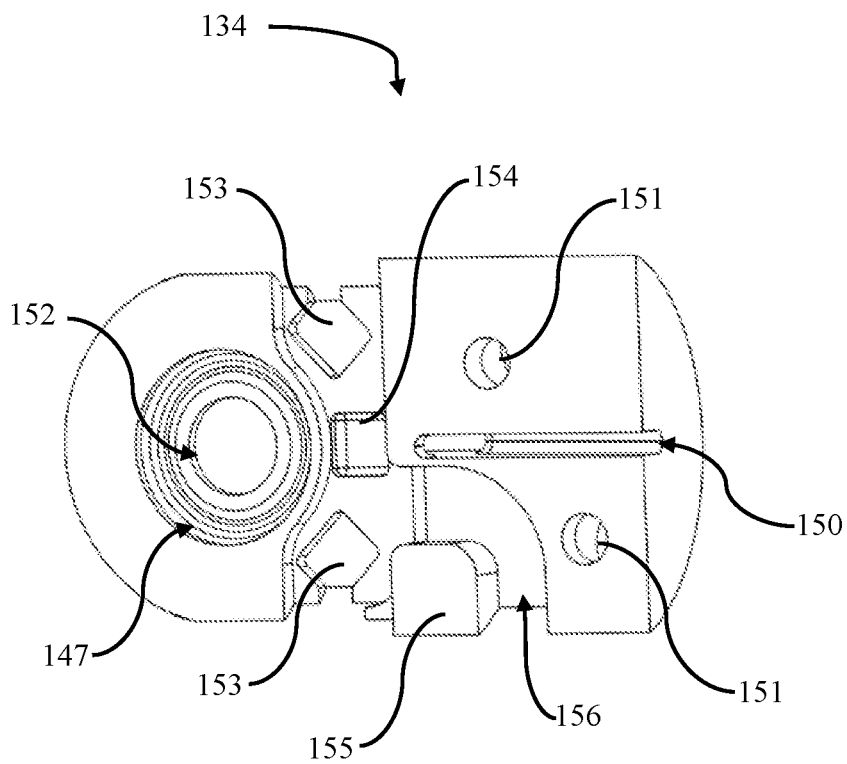
FIG. 10B is an isometric view of a female hinge body according to one embodiment.

As mentioned above the hinge-rotary assembly 102 also comprises the female hinge body or hinge cover 134. FIGS. 10A-10B show multiple views of an illustrative embodiment of the female hinge body or hinge cover 134. As depicted in FIGS. 10A-10B, in some embodiments, the female hinge body 134 contains an inner and outer surface. In one embodiment, the outer surface of the female hinge body 134 contains a plurality of connection apertures 151. The connection apertures 151 are configured to allow screws to enter and pass through said apertures, with said screws entering and mating with the tapped holes 148 located on the male rotary-hinge body 139, thus coupling the female hinge body 134 with the male rotary-hinge body 139.

In some embodiments, also located on the outer surface is a cable routing slot 150. As shown in FIG. 10B, the cable routing slot 150 extends from the inner surface of the female hinge body 134 to the outer surface of said body. Similar to the cable guide slot 143 of the male rotary-hinge body 139, the cable routing slot 150 of the female hinge body 134 is configured to route and guide cable 185 from the hinge-rotary assembly 102 through the proximal end of the jaw assembly 101 to the redirecting cable raceway 120 (FIG. 5A). In these embodiments, cable 185 is routed through the cable conduit 142 of the male rotary-hinge body 139 to the inner surface the female hinge body 134, where said enters the cable routing slot 150 and passes through an aperture, such that the cable is situated in the cable routing slot on the outer surface of the female hinge body 134. In addition, at the end of the cable routing slot 150 are decoupling surfaces 195. These decoupling surfaces 195 are harmonious to the decoupling surfaces 194 of the hinge-rotary body 139, in that they are fabricated to be curved in shape, such that the cable routed through said routing slot do not change in length when the jaw assembly is rotated about the pitch axis, thus helping to effectuate the decoupled motion.

In addition, in some embodiments located on the inner surface of the female hinge body 134 is a flex pocket 156 and a flex routing protrusion 155. In these embodiments, the flex pocket 156 and the flex routing protrusion 155 are configured to harmoniously route electrical communication components to a plurality of sensor pockets 153 and an electrical communication pocket 154 located on the inner surface of the female hinge body 134. In addition to routing electrical communication components, the flex pocket 156 is also configured to act as a housing for said communication components, such that said components are not damaged during actuation and articulation of the wrist assembly 100.

As mentioned above, in some embodiments located on the inner surface of the female hinge body 134 is a communication component pocket 154 and sensor pockets 153. The sensor pockets 153 are configured to allow position and/or orientation sensors to sit in said pockets, such that they do not become damaged during actuation of the wrist assembly 100. In these embodiments, the sensor pockets 153 are situated on the inner surface of the female hinge body 134 such that said pockets are orthogonal to one another about the center point of a magnet pocket 152 located on the hinge non-flex body 108 (FIG. 7B). In different embodiments, a variety of position sensors may be used, including but not limited to, hall-effect sensors, optical encoders, resistive position sensors, and/or any other standard means of measuring position or combination thereof. In these embodiments, the sensors which sit in the sensor pockets 153 are configured to obtain position and/or orientation data of the jaw assembly 100 as said assembly is rotated about the pitch axis 188.

Similar to the sensor pockets 153, in one embodiment the communication component pocket 154 is configured to house capacitors. In this embodiment, capacitors are utilized to reduce signal noise from the sensors and other electrical communication components, so as to provide more accurate sensor readings, resulting in more accurate position data. In some embodiments, the communication component pocket 154 is configured to house two or more capacitors, while in other embodiments only one capacitor is housed in said component pocket. In alternative embodiments, the communication component pocket 154 is configured to house components required for measurement and/or communication, such as inductors, resistors and/or processors known in the art.

In some embodiments, the inner surface of the female hinge body 134 contains a bearing race 147. In these embodiments, the bearing race 147 is configured to allow a ball bearing set 109 to sit within and ride along said race during actuation of the wrist assembly 100. As detailed above, the ball bearing set 109 which sits within the bearing race 147 of the female hinge body 134 also sits within the hinge bearing race 129 of the hinge non-flex body 108 (FIG. 7A), fashioning a coupling between the female hinge body 134 and the hinge non-flex body 108. The aforementioned coupling between the female hinge body 134 and the hinge non-flex body 108, allows the jaw assembly 101 to rotate about the pitch axis 188.

As detailed above, the proximal ends of both the hinge flex body 107 and hinge non-flex body 108 couple to the inner surfaces of the distal ends of both the male rotary-hinge body 139 and the female hinge body 134, thus coupling the jaw assembly 101 with the hinge-rotary assembly 102. In addition to coupling the jaw assembly 101 to the hinge-rotary assembly 102, the aforementioned coupling of the distal end of the male rotary-hinge body 139 to the proximal end of the hinge flex body 107 and the distal end of the female hinge body 134 to the proximal end of the hinge non-flex body 108, also constrains the jaw assembly 101 such that during actuation, the jaw assembly can only be rotated about the pitch axis 188.

As detailed above, in some embodiments, the proximal ends of the hinge flex body 107 contains a fulcrum 128 for which the idler pulley 137 rotates about. FIGS. 16A-16B show multiple views of an illustrative embodiment of the idler pulley 137. The idler pulley 137 in combination with the proximal ends of both the hinge flex body 107 and the hinge non-flex body 108 and the distal ends of both the male rotary-hinge body 139 and the female hinge body 134 is configured to provide rotational movement of the jaw assembly 101 about the pitch axis 188. Additionally, the idler pulley 137 is configured to route cable 182 to the actuation hub 184 of the first jaw 103.

As shown in FIG. 16A, in some embodiments the idler pulley 137 contains an idler cable raceway 178. The idler cable raceway 178 is configured to route cable 182 to the actuation hub 184 of the first jaw 103. The idler pulley 137 contains an opening for which the fulcrum 128 of the hinge flex body 107 passes through. As shown in FIG. 16A, the interior surface of the opening of the idler pulley 137, contains a bearing race 177. As shown in FIG. 16B, the bearing race 177 of the idler pulley 137 is configured to allow one of the pluralities of ball bearing sets 109 to sit within and ride along said race. In these embodiments, the ball bearing set 109 which sits within the bearing race 177 contacts the fulcrum 128 of the hinge flex body 107 so as to allow the idler pulley 137 to rotate about said fulcrum along the pitch axis 188. In alternative embodiments, the ball bearing set 109 is substituted for a sleeve bearing, a bushing, an axle and/or other rolling element bearings known in the art.

In some embodiments, the hinge rotary assembly 102 also comprises a rotary pulley body 140. As detailed above, the rotary pulley body 140 mates and couples to the male rotary-hinge body 139. FIGS. 13A-13D show multiple views of an illustrative embodiment of a rotary pulley body 140. As shown in FIGS. 13A-13D, the rotary pulley body 140 is configured to be cylindrical in shape having an opening so as to allow the proximal end of the male rotary-hinge body 139 to pass through said opening. In one embodiment, the rotary pulley body 140 contains a distal and proximal end, with the distal end containing a plurality of tapped holes 168 configured to allow screws from the proximal end of the male rotary-hinge body 139 to enter said holes, coupling the rotary pulley body 140 to the male rotary-hinge body 139 (FIG. 9B). Additionally, as detailed above, in some embodiments the distal end of rotary pulley body 140 contains a plurality of pin connection apertures 144 (FIG. 13B). In these embodiments, the plurality of pin connection apertures 144 are configured to allow pins to enter and sit within said apertures of the rotary pulley body 140 as well as sit within pin connection apertures 144 located on the proximal end of male rotary-hinge body 139 (FIG. 9B). In these embodiments, the pin connection fixes the rotary pulley body 140 to the male rotary-hinge body 139 such that the rotary pulley body 140 does not rotate relative to the male rotary-hinge body 140 but is able to rotate relative to a female rotary body 141 (FIG. 14A). In other embodiments, the rotary pulley body 140 and the male rotary-hinge body are fabricated as one piece.

In addition, in some embodiments, the distal end of the rotary pulley body 140 contains termination knot cavities 167 (FIG. 13B). The termination knot cavities 167 are configured to allow the knots of terminated cables to sit within, so that they do not interfere with the actuation of the wrist assembly 100. In some embodiments, rotary cables (not shown) are routed through cable entry holes 165 located on the outer surface of the rotary pulley body 140. In these embodiments, the rotary cables are utilized to provide rotary actuation to the wrist assembly 100. In some embodiments, two rotary cables are utilized to effectuate rotation of the wrist assembly 100 about the roll axis 192. In these embodiments, one rotary cable is used to effectuate rotation of the wrist assembly 100 about the roll axis 192 in one direction, and the second rotary cable is used to effectuate rotation of the wrist assembly 100 about the roll axis 192 in the opposite direction. In some embodiments, the rotary cable enters the cable entry hole 165 on the outer surface of the proximal end of the rotary body 140 on the left side of said body and terminating in the termination site 166 on the left side of the rotary pulley body 140, with the second rotary cable entering the cable entry hole 165 on the outer surface of the distal end of the rotary pulley body 140 on the right side of said body, and terminating in the termination knot cavity 167 located on the right side of the rotary pulley body 140. Rotary cables terminate using the termination techniques detailed above.

Figure 13A:
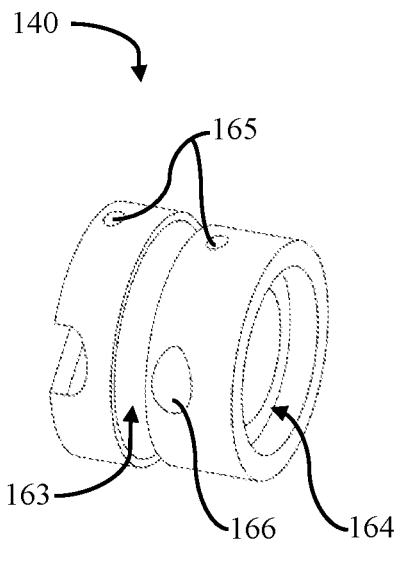
FIG. 13A is an isometric view of a rotary pulley body according to one embodiment.
Figure 13B:
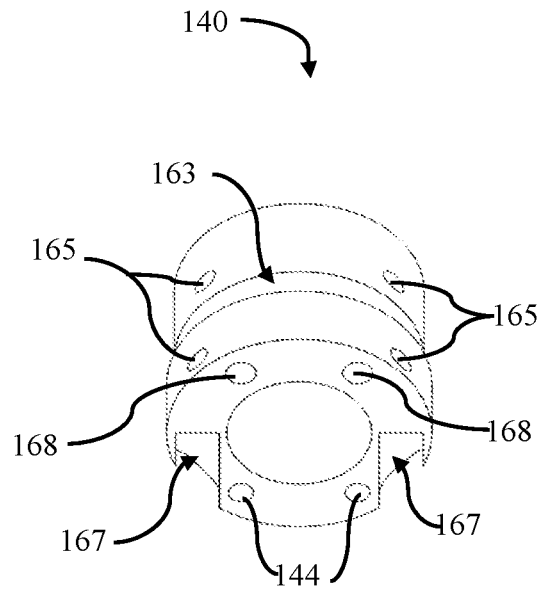
FIG. 13B is a front perspective view of a rotary pulley body according to one embodiment.
Figure 13C:
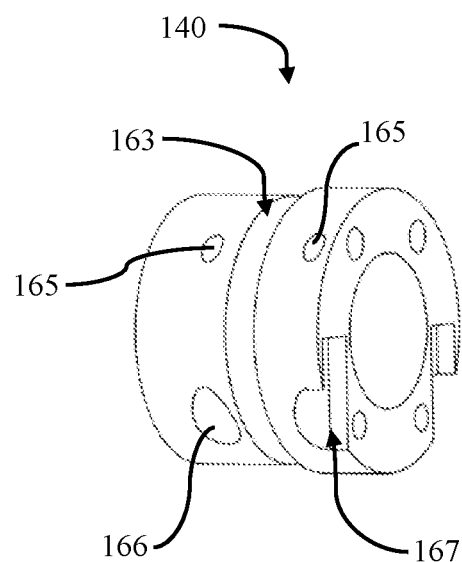
FIG. 13C is an additional isometric view of a rotary pulley body according to one embodiment.
Figure 13D:
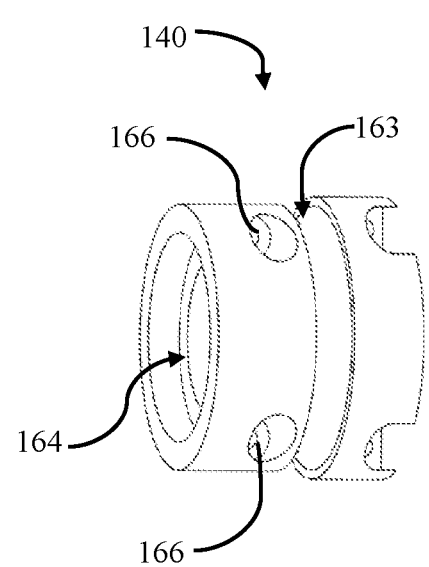
FIG. 13D is an additional isometric view of a rotary pulley body according to one embodiment.
Figure 14A:
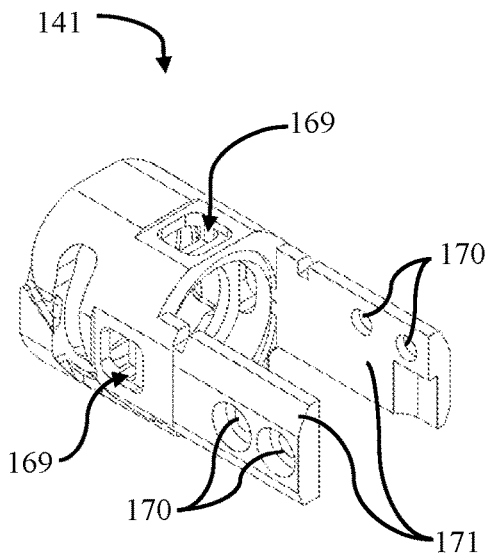
FIG. 14A is an isometric view of a female rotary body according to one embodiment.

In some embodiments, the inner surface of the proximal end of the rotary pulley body 140 contains a magnet seat 164, which is configured to allow a magnet to sit and rest along (FIG. 13A). As detailed above, in some embodiments, the outer surface of the rotary pulley body 140 contains the rotary bearing race 163, which is configured to allow one of the pluralities of ball bearing sets 109 to sit within and ride along said race. In these embodiments, the ball bearing set 109 that sits within the rotary bearing race 163 also sits within and rides along a female rotary bearing race 172 located on the inner surface of the distal end of the female rotary body 141 (FIG. 14C). In these embodiments, the rotary pulley body 140 is configured to partial sit within the distal end of the female rotary body 141, with the rotary bearing race 163 configured to serve as an inner race for the ball bearing set 109, with the female rotary bearing race 172 configured to serve as an outer race for the said ball bearing set, effectuating a coupling between the rotary pulley body 140 and the female rotary body 141. In these embodiments, both the rotary bearing race 163 (FIG. 13A) and the female bearing race 172 (FIG. 14C) are fabricated and configured to support axial and non-axial loads and/or forces when the wrist assembly 100 is rotated about the roll axis 192, so as to constrain the rotary pulley body 140 and male rotary-hinge body 139 such that both aforementioned bodies can rotate relative to the female rotary body 141.

Figure 14B:
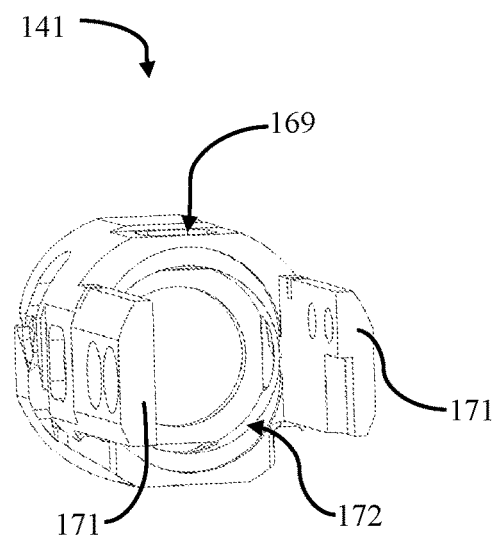
FIG. 14B is a rear isometric view of a female rotary body according to one embodiment.
Figure 14C:
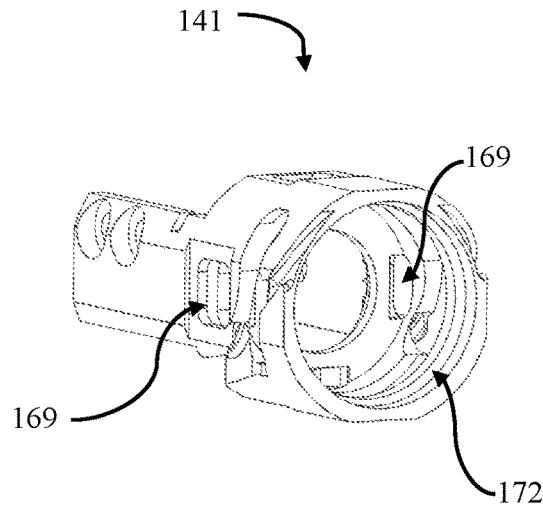
FIG. 14C is a front diagonal isometric view of a female rotary body according to one embodiment.

FIGS. 14A-14D show multiple views of an illustrative embodiment of a female rotary body 141. As mentioned above, in some embodiments, the female rotary body 141 is fabricated to contain a distal and proximal end, with both ends containing an outer and inner surface. As detailed above, in some embodiments the inner surface of the distal end of the female rotary body 141 contains the female rotary bearing race 172. Additionally, in some embodiments, the female rotary body 141 contains another female rotary bearing race located proximal to the bearing race detailed above (FIG. 14B). In this embodiment, a radial bearing (not shown) sits in the female rotary bearing race 172 and at the most proximal end of the male hinge-rotary body 139.

Furthermore, in some embodiments, the distal end of the female rotary body 141 contains a plurality of sensor pockets 169, with said pockets protruding to the inner surface of the female rotary body 141 (FIG. 14C). The plurality of sensor pockets 169 are configured to house sensors for determining position and/or orientation of the wrist assembly 100 about the roll axis 192, similar to the sensor pockets 153 of the female hinge body 134 detailed above. In these embodiments, the position and/or orientation of the wrist assembly 100 are measured using magnets in the same manner detailed above for determining the position and/or orientation of the jaw assembly 101 about the pitch axis 188.

Figure 14D:
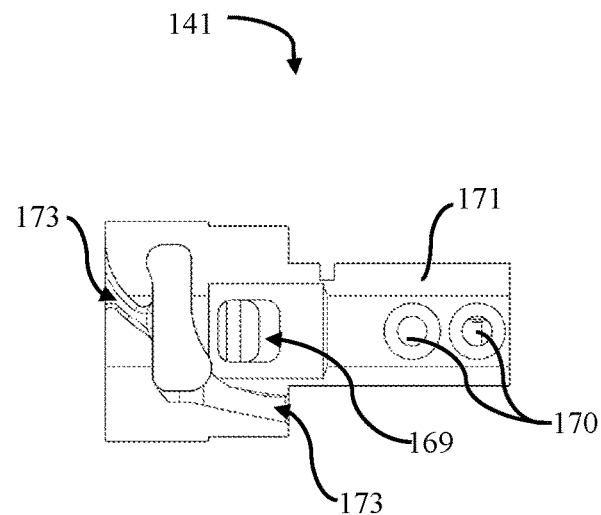
FIG. 14D is a side profile view of a female rotary body according to one embodiment.

As shown in FIG. 14D, in some embodiments, located on the outer surface of the distal end of the female rotary body 141 is a contoured cable pathway 173. In some embodiments, the female rotary body 141 contains two contoured cable pathways 173, one on either side of the distal end of said body. In these embodiments, the contoured cable pathways 173 are configured to route rotary cables from the female rotary body 141 to the rotary pulley body 141. In some embodiments, two rotary cables are utilized to effectuate rotation of the wrist assembly 100 about the roll axis 192, with one rotary cable utilized to effectuate rotation about the roll axis 192 in one direction and the other rotary cable effectuating rotation about the roll axis 192 in the opposite direction.

As mentioned above, the female rotary body 141 is configured to have a proximal end. In these embodiments, the proximal end contains a plurality of connection bosses 171 that protrude from the distal end of the female rotary body 141. The connection bosses 171 are configured to mate the wrist assembly 100 to the rest of a robotic arm. As seen in FIG. 14A, in some embodiments, the connection bosses 171 contain a plurality of connection apertures 170, configured to mate the wrist assembly to a proximal structure or actuator of a robotic arm. In some embodiments, a screw connection is used to effectuate the aforementioned mating, while in other embodiments, various alternative methods of fastening and/or connections are utilized, included but not limited to, tapped connections, adhesive connections, welded connections and/or any other methods or combinations of methods known in the art.

Figure 26A:
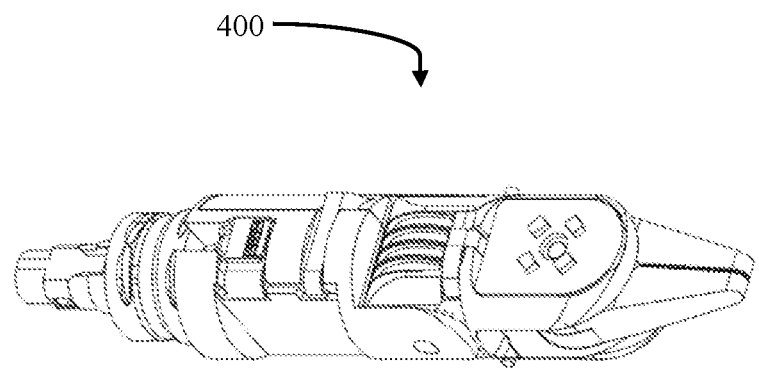
FIG. 26A shows an isometric view of a wrist assembly according to one embodiment.
Figure 26B:
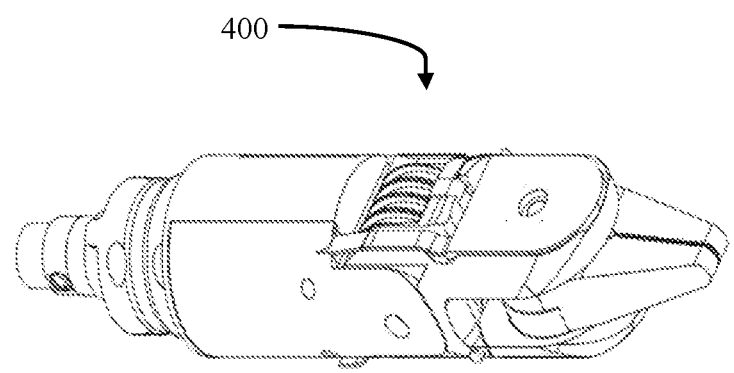
FIG. 26B shows an additional isometric view of a wrist assembly according to one embodiment.
Figure 26C:
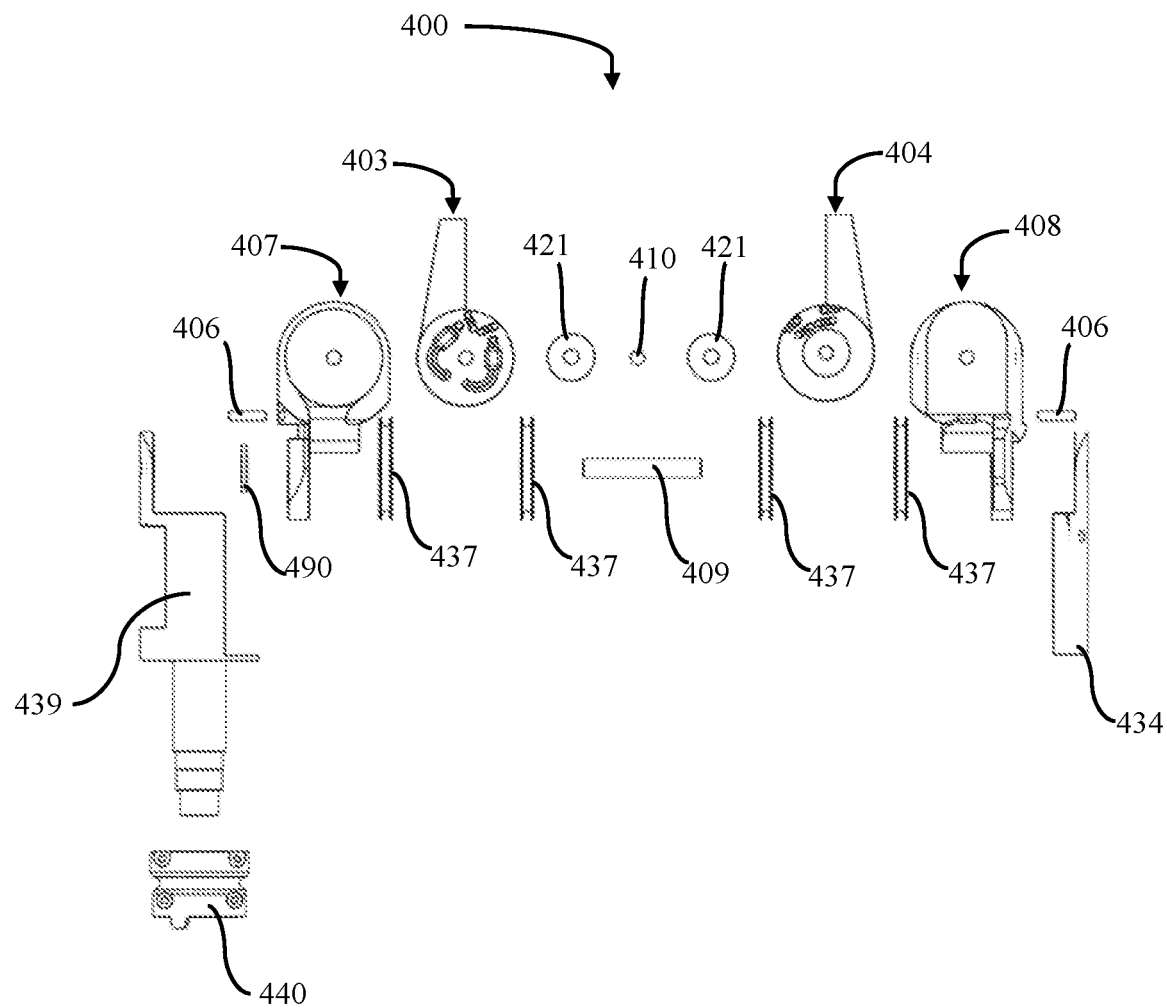
FIG. 26C shows an exploded top profile view of a wrist assembly according to one embodiment.
Figure 28A:
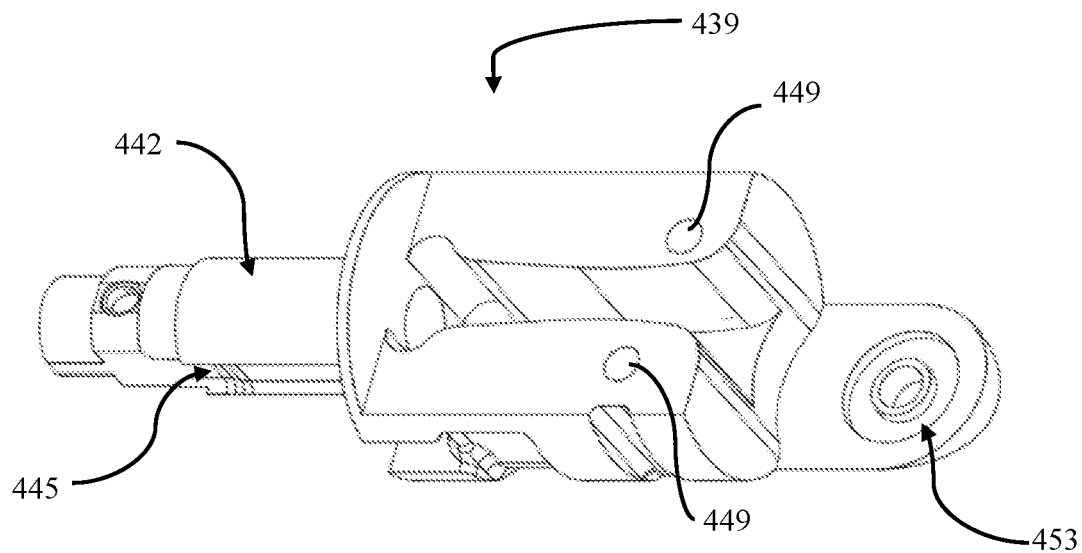
FIG. 28A shows a front isometric view of a hinge-rotary body according to one embodiment.
Figure 28B:
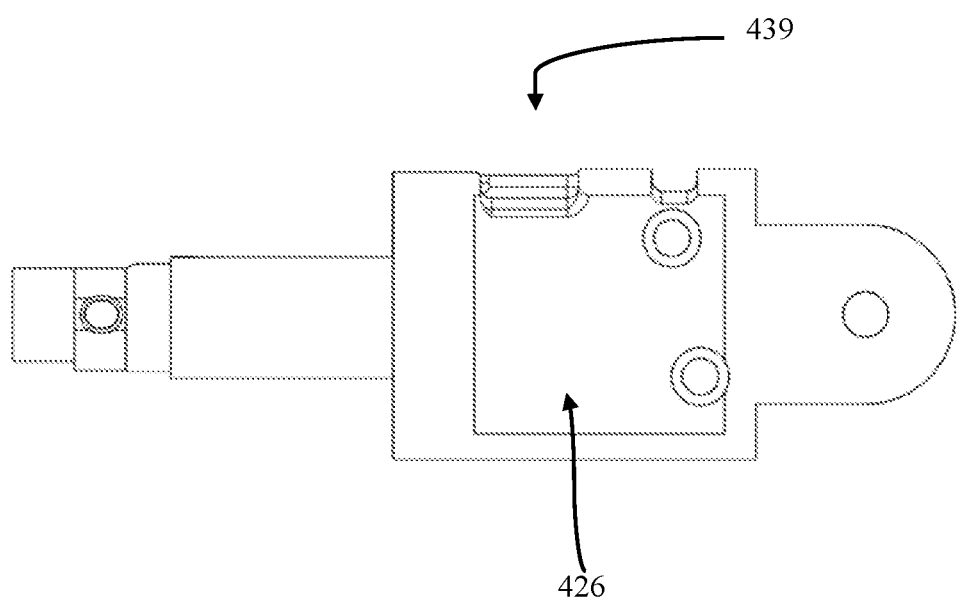
FIG. 28B shows a back profile view of a hinge-rotary body according to one embodiment.

FIGS. 26A-26C show an illustrative embodiment of another wrist assembly 400. In these embodiments, the bearing races and ball bearings sets of the assembly are eliminated, and a plain bearing setup is utilized to facilitate rotation of the first and second jaw about the jaw axis, as well as rotation of the jaw assembly about the pitch axis. FIG. 26C shows an exploded view of the illustrative embodiment of wrist assembly 400. Similar to the embodiments detailed above, wrist assembly 400 is fabricated to have a jaw assembly 401 (FIG. 31) and a hinge-rotary assembly (FIGS. 28A-28B).

Figure 30A:
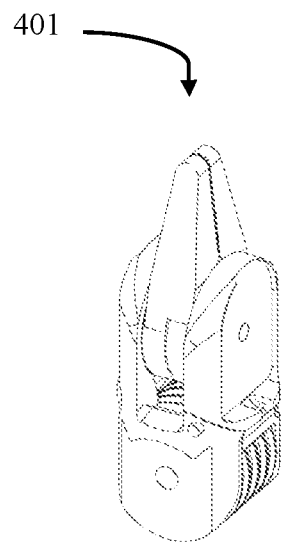
FIG. 30A shows an isometric view of a jaw assembly according to one embodiment.
Figure 30B:
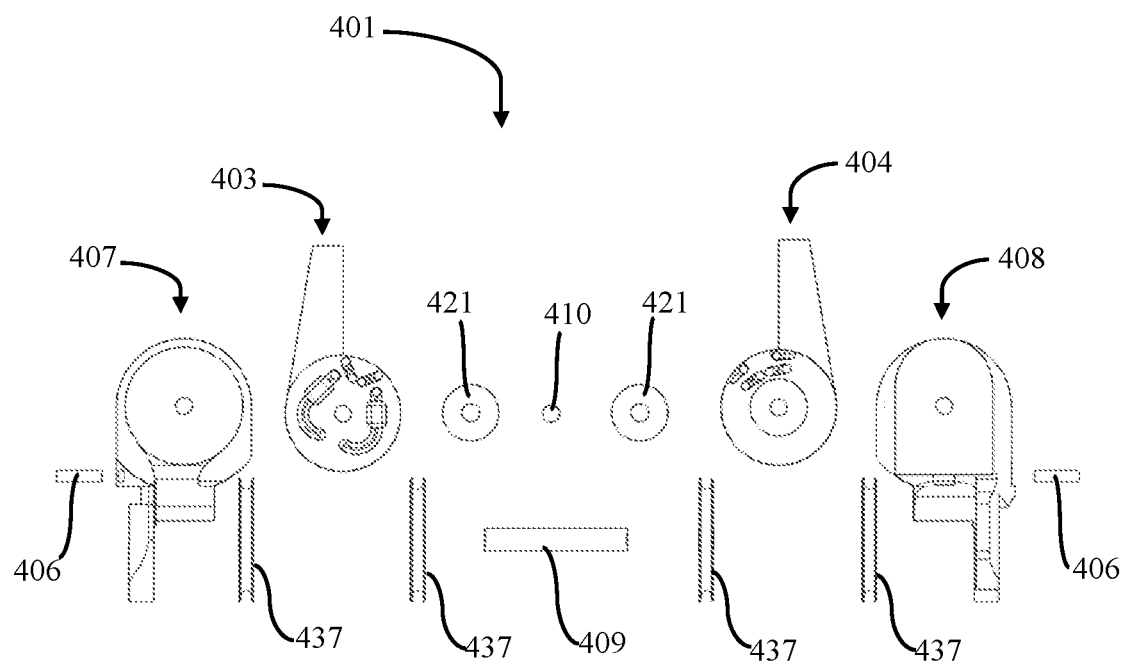
FIG. 30B shows an exploded top view of a jaw assembly according to one embodiment.

FIG. 30A shows an illustrative embodiment of the jaw assembly 401. As shown in FIG. 30B, in some embodiments, jaw assembly 401 comprises a first jaw 403, a second jaw 404, two bodies a hinge flex body 407 and a hinge non-flex body 408, four idler pulleys 437, a jaw bearing shaft 410 and a hinge pulley shaft 409, amongst other components.

FIGS. 31A-31D show an illustrative embodiment of the first jaw 403. In some embodiments, the first jaw 403 and the second jaw 404 are symmetrical. In these embodiments, the first jaw and the second jaw both comprise a working segment 483 at the distal end of the jaw, as well as an actuation segment (or hub) 484 at the proximal end of the jaw. The working segments of the first jaw and second jaw are analogous to the working segments of other embodiments of the first jaw, in that it can be configured to have various types of surfaces in different embodiments, including but not limited to the configurations detailed above. As stated above, in some embodiments the distal end of the first and second jaws are configured to have an actuation segment 484. In these embodiments, the actuation segment is cylindrical in shape, and contains an aperture for a jaw bearing shaft 410 to pass through. In these embodiments, the first and second jaws rotate about the jaw bearing shaft 410, which is configured as a plain bearing. The jaw shaft mates the first and second jaws, as well as defines the jaw axis. In addition, the jaw shaft also mates the hinge flex body 407 and the hinge non-flex body 408.

In some embodiments, on the perimeter of the actuation hubs of both the first and second jaws are cable race ways 411 which are configured to route two cables to their termination sites 405a and 405b on the actuation segment. In some embodiments, cables 482 and 491 are routed and terminated on the first jaw, with cables 485 and 481 being routed and terminated on the second jaw. In other embodiments, cable 482 and 491 are routed and terminated on the second jaw and cables 485 and 491 are routed and terminated on the first jaw. The respective cables are routed through the raceway of their respective actuation segment where they enter and pass through a first cable passage 420a, then back through a second cable passage 420b, where said cable is routed to its termination site. In these embodiments, the actuation segment of the first and second jaw are fabricated to have four cable passages 420a, 420b, 420c, 420d, two for each of the two cables that terminate on the actuation segment. In some embodiments, the cables terminate by means of clamping the respective cable in its termination site via a setscrew. Alternatively, in some embodiments, other appropriate means or techniques known in the art are used. For example, a polymer fiber cable may terminate via a knot tied in the cable, while a metal fiber cable may terminate by means of a crimp or swaged connection.

In addition, in some embodiments, the actuation segment of the first and second jaw both comprise a magnet slot 452 configured to allow a magnet 421 to sit in. As detailed throughout, the magnets are utilized to obtain position and orientation data of components of the wrist assembly as said assembly is actuated about an axis. In these embodiments the magnets 421 which sit within the magnet slots 452 of the first and second jaws are utilized to obtain the position and orientation of the first and second jaws, as said jaws are rotated about the jaw axis. In these embodiments, the magnet slots are configured to have a through hole, so as to allow the jaw shaft to pass through. Additionally, the magnets 421 which sit within the magnet slots are also fabricated to have a through hole to allow the jaw shaft to pass through, with one end of the jaw shaft mating with the hinge flex body and the other end mating with the hinge non-flex body.

Figure 31A:
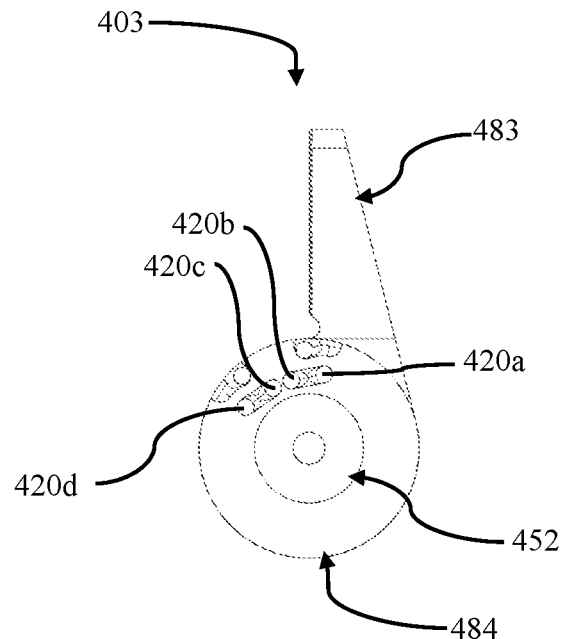
FIG. 31A shows a side profile view of a first jaw according to one embodiment.
Figure 31B:
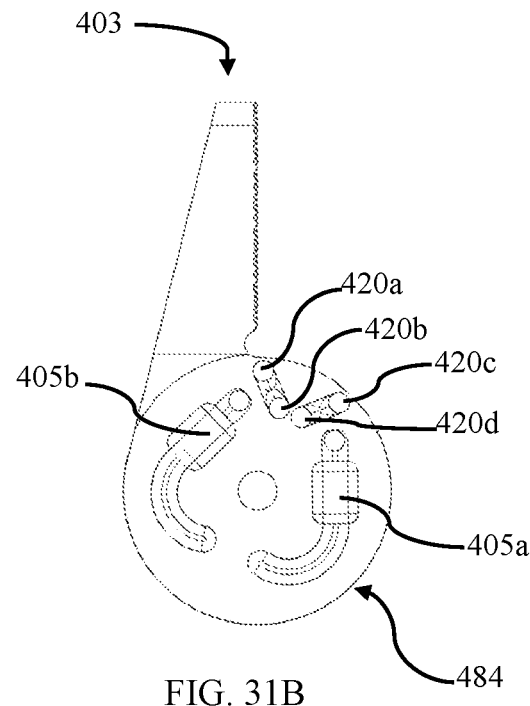
FIG. 31B shows an additional side profile view of a first jaw according to one embodiment.
Figure 31C:
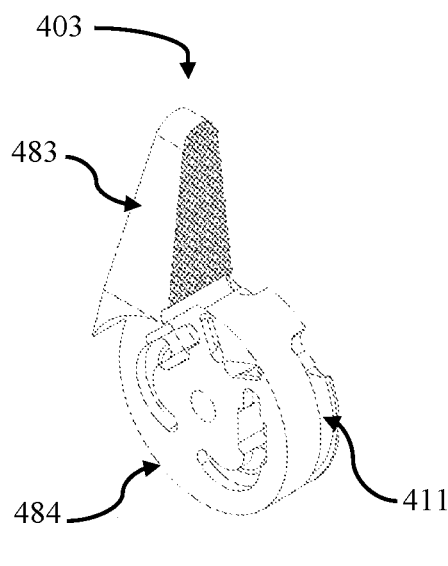
FIG. 31C shows an isometric view of a first jaw according to one embodiment.
Figure 31D:
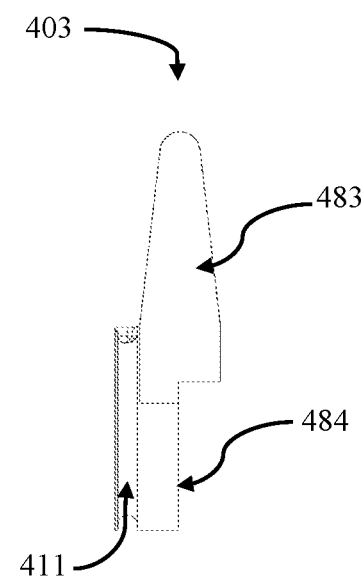
FIG. 31D shows a top profile view of a first jaw according to one embodiment.

As stated above, in some embodiments the jaw assembly 401 comprises four idler pulleys 437. In these embodiments, each of the idler pulley 437 is utilized to route and direct an individual cable to the cable raceway 411 of the jaw that each respective cable terminates on (FIGS. 31C-31D). The idler pulleys 437 contain an aperture for the hinge pulley shaft 409 configured as a plain bearing to pass through. In these embodiments, the idler pulleys rotate about the hinge pulley shaft, with said pulley shaft defining the pitch axis, thus allowing the jaw assembly to be rotated about said pitch axis. In addition, the hinge pulley shaft acts as a mating between the jaw assembly and the hinge rotary assembly.

Figure 32A:
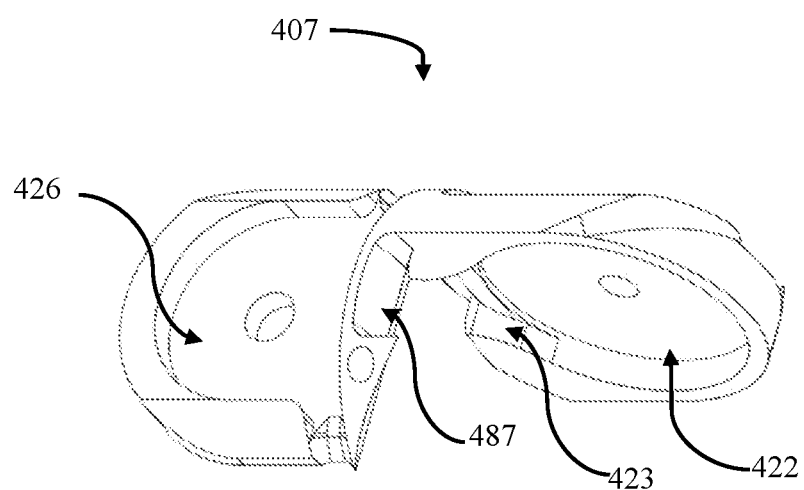
FIG. 32A shows an isometric view of a hinge flex body according to one embodiment.
Figure 32B:
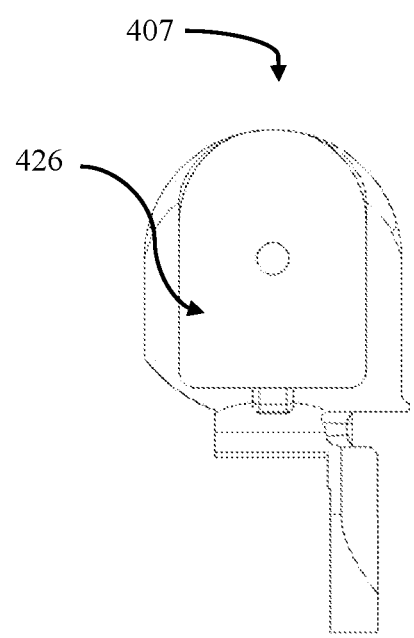
FIG. 32B shows a top profile view of a hinge flex body according to one embodiment.

In addition, jaw assembly 401 contains a hinge flex body 407 and a hinge non-flex body 408. Similar to embodiments detailed above, in these embodiments the hinge flex body 407 and the hinge non-flex body 408 function as a housing for the first and second jaw, along with other components of the jaw assembly. Likewise, in these embodiments, the hinge flex body and the hinge non-flex body are constructed to have a distal and proximal end, with the distal end and proximal end both having an interior and exterior surface. Furthermore, the hinge flex body and a hinge non-flex body are fabricated to have approximately the same architecture such that the connection between them is seamless, with the outer profiles of both bodies being flush with one another. FIGS. 32A-32B show an illustrative embodiment of the hinge flex body 407. The proximal end of the hinge flex body is utilized to couple and mate the jaw assembly with the hinge-rotary assembly, as well defines a pitch axis.

As seen in embodiment shown in FIGS. 32A-32B, located on the exterior side of the proximal end of the hinge flex body, is a flex pocket 426, for which an electrical communication component sits in. In addition, the flex pocket 426 is configured to have a through hole for which the pulley shaft passes through. The hinge flex body is also configured to have locking pin connections 406 for connecting the hinge flex body with the hinge non-flex body. In these embodiments, one end of a locking pin enters a connection slot on the hinge flex body, with the other end of the locking pin entering a connection slot on the hinge non-flex body and thus mating the hinge flex body and hinge non-flex body. Similarly, a second locking pin connection is found on the hinge non-flex body, the two locking pin connections 406 not only mate the hinge flex body with the hinge non-flex body, but also constrains the rotation of the jaw assembly about the pitch axis. In addition, the proximal end of the hinge flex body is configured to have a jaw hard stop surface 487, in order to constrain the rotation of the jaw assembly about the pitch axis, such that the jaw assembly is not rotated past its allowable range of motion.

As mentioned above, the hinge flex body is fabricated to have a distal end having an interior and exterior surface. In one embodiment, the interior surface of the distal end of the hinge flex body is fabricated to have an actuation segment pocket 422 that is cylindrical in shape, such that the actuation segment of the first jaw sits within said pocket. The actuation pocket 422 is fabricated to have a cable routing surface 423 to help guide cables to the cable raceway of the actuation segment, as well to have a through hole for the jaw bearing shaft to pass through thus effectuating a plain bearing. On the exterior surface of the distal end of the hinge flex body is a second flex pocket for additional electrical communication components to sit in, as well as sensors for obtaining the position and orientation of the first jaw. In some embodiments two sensors are found in the flex pocket, while in other embodiments four sensors are found in the flex pocket.

Figure 33A:
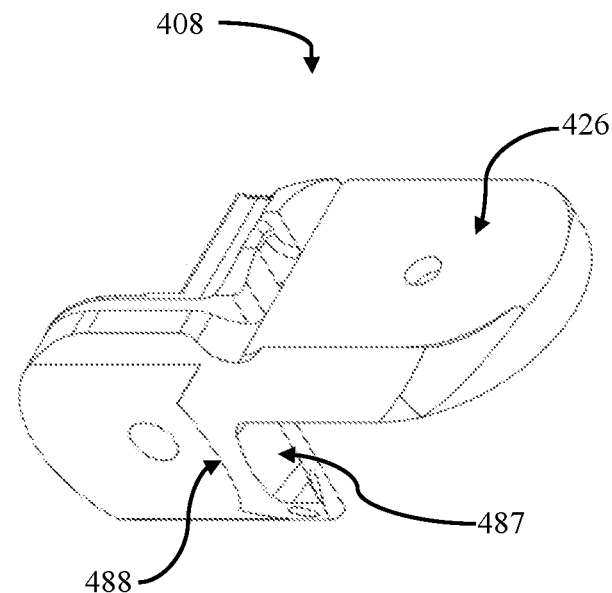
FIG. 33A shows an isometric view of a hinge non-flex body according to one embodiment.
Figure 33B:
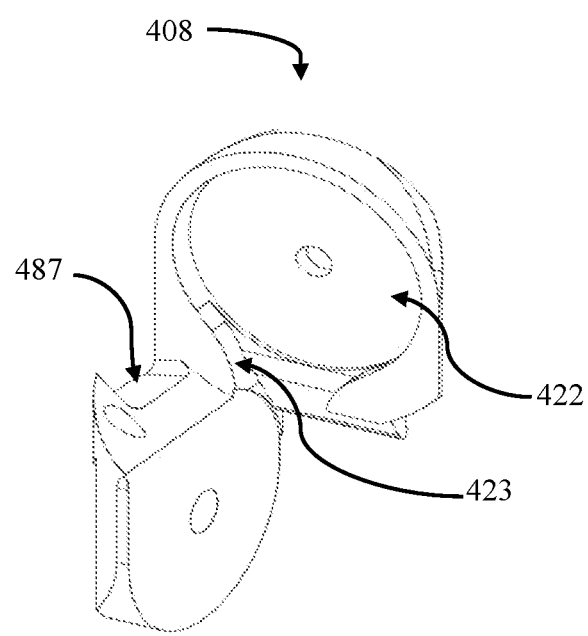
FIG. 33B shows an additional isometric view of a hinge non-flex body according to one embodiment.

FIGS. 33A-33B show an illustrative embodiment of the hinge non-flex body 408. In these embodiments, the hinge non-flex body is fabricated to have proximal and distal end, with both ends having an interior and exterior surface. As depicted in FIG. 33B, the interior surface of the distal end of the hinge non-flex body is fabricated to have an actuation segment pocket 422 that is cylindrical in shape, such that the actuation segment of the second jaw sits within said pocket. The actuation pocket is fabricated to have a cable routing surface 423 to guide cables to the cable raceway of the actuation segment. Additionally, the actuation pocket 422 is fabricated to have a through hole for the jaw bearing shaft to pass through thus effectuating a plain bearing. On the exterior surface of the distal end of the hinge non-flex pocket is a flex pocket 426 for electrical communication components to sit in, as well as sensors for obtaining the position and orientation of the second jaw. In some embodiments two sensors are found in the flex pocket, while in other embodiments four sensors are found in the flex pocket 426. In these embodiments, the proximal end of the hinge non-flex body contains a jaw axis hard stop 487 to prevent the jaws from being actuated about the jaw axis past their allowable range of motion. Additionally, the proximal end contains a locking pin connection 406 identical to the one detailed above for the hinge flex body. Furthermore, the exterior surface of the proximal end of the hinge non-flex body contains a pitch hard stop 488, which is configured to prevent the jaw assembly 401 from being actuated about the pitch axis past its allowable range of motion.

Figure 27A:
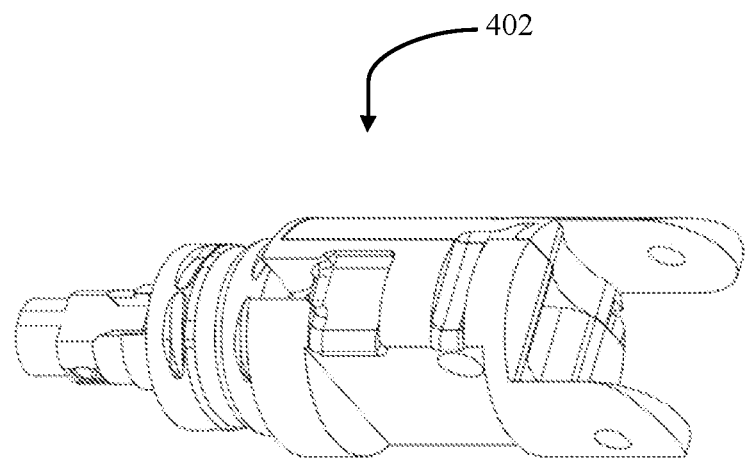
FIG. 27A shows an isometric view of a hinge-rotary assembly according to one embodiment.
Figure 27B:
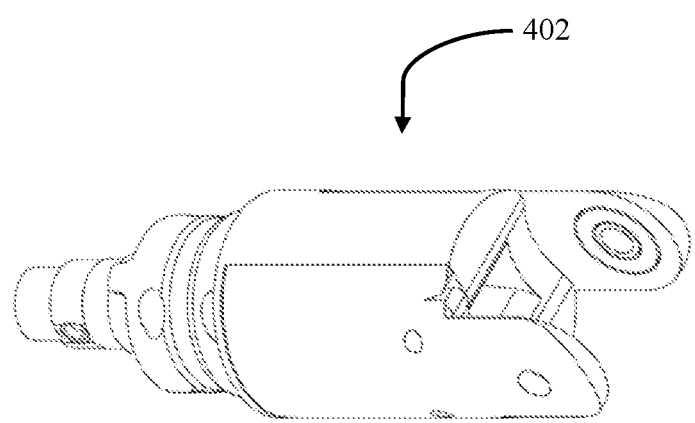
FIG. 27B shows an additional isometric view of a hinge-rotary assembly according to one embodiment.

As stated above, wrist assembly also contains a hinge-rotary assembly 402. FIGS. 27A-27B show an illustrative embodiment of the hinge-rotary assembly 402. In some embodiments, hinge-rotary assembly 402 is fabricated to have a hinge cover 434, a hinge-rotary body 439 and a rotary pulley body 440. In these embodiments, the hinge-rotary body 439 performs the same function as the male hinge-rotary body 139 detailed above. FIGS. 28A-28B shows an illustrative embodiment of the hinge-rotary body 439. Similar to the male hinge-rotary body detailed above, in these embodiments the hinge-rotary body 439 has a distal and proximal end, as well as interior and exterior surfaces. As seen in FIG. 28A, in some embodiments, on the interior of the distal end of the hinge-rotary body is a magnet pocket 453, for which a magnet 490 (FIG. 26C) sits in. In these embodiments, the magnet 490 that sits with the magnet pocket 453 of the hinge-rotary body is utilized to obtain position and orientation data of the jaw assembly as it is rotated about the pitch axis. In these embodiments, the magnet pocket is configured to have a through hole for the hinge pulley shaft to sit in, thus creating a plain bearing. In addition, in these embodiments located on the interior of the distal end of the hinge-rotary body are through holes 449 which are configured to all a screw to enter and thus mate and couple the hinge cover 434 to the hinge-rotary body 439. In some embodiments, the interior of the distal end is fabricated to have curved surfaces for guiding cables to the respective locations on the jaw assembly. In some embodiments, located on the exterior surface of the distal end of the hinge-rotary body is a flex pocket 426 for which an electrical communication component sits.

Figure 29A:
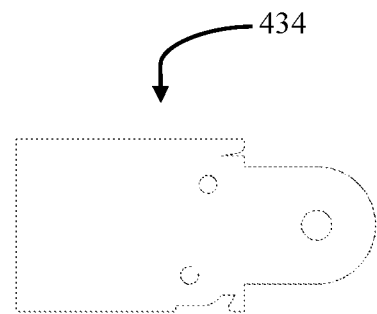
FIG. 29A shows a back profile view of a hinge cover according to one embodiment.
Figure 29B:
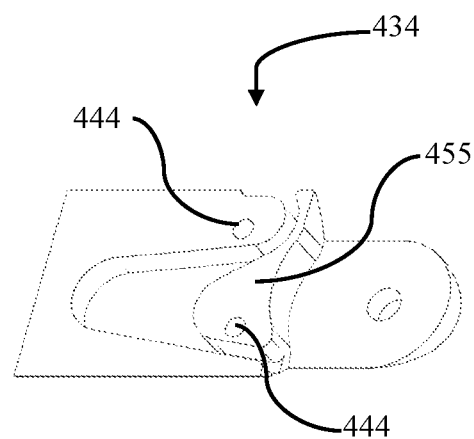
FIG. 29B shows a front isometric view of a hinge cover according to one embodiment.
Figure 29C:
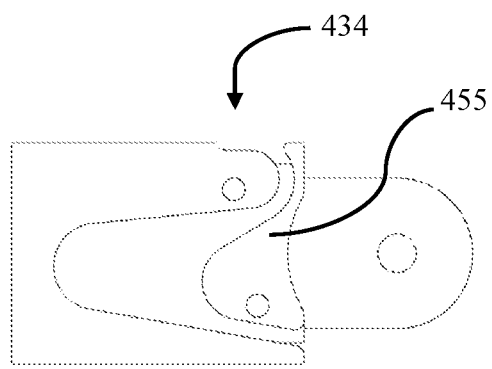
FIG. 29C shows a front profile view of a hinge cover according to one embodiment.

In these embodiments the proximal end of the hinge-rotary body is configured to have a cable conduit 442 similar to the one detailed above for the male hinge-rotary body. As detailed above, the cable conduit 442 is utilized to route cables to the jaw assembly, such that when the wrist assembly is rotated about the roll axis the cables do not become tangled with one another. As seen in FIG. 28A, in some embodiments located on the inner surface of the cable conduit 442 is a flex guide surface 445. In these embodiments, the flex guide surface 445 is configured to be flat such that electrical communication components sit flat against the surface so as to not become damaged during actuation of the wrist assembly. In these embodiments, an electrical communication component is routed on the flex guide surface to the flex pocket situated on the exterior of the distal end of hinge-rotary body. The electrical communication component is then routed to the interior surface of the hinge-rotary body, where it routed to the hinge cover 434. FIGS. 29A-29C show an illustrative embodiment of the hinge cover 434. The hinge cover is analogous to the female hinge body 134 detailed above, in that acts as a housing for components of the hinge-rotary assembly, as well as used to route electronic communication components from the hinge-rotary assembly to the jaw assembly. As shown in FIGS. 29B-29C, on the interior of the hinge cover, is a routing protrusion 455 which creates a pocket for an electrical communication component to be routed to the jaw assembly. In addition, in some embodiments, the interior surface of the hinge cover 434 contain connection apertures 444 for which screws from the hinge-rotary body enter, thus coupling the hinge cover with the hinge-rotary body. In addition, on the distal end of the hinge cover is a through hole for which the hinge pulley shaft sits in.

As mentioned above, the hinge-rotary assembly 402 also contains a rotary pulley body 440. In these embodiments, the rotary pulley body 440 is identical to rotary pulley body 140 detailed above. As with rotary pulley body 140, rotary pulley body 440 is utilized to provide rotation of the wrist assembly about the roll axis.

Actuation, Control and Sensing of the Wrist Assembly

As stated previously, in particular embodiments, the wrist assembly is fabricated and designed to be incorporated and utilized with the Virtual Reality Surgical Device disclosed in International Patent Application No. PCT/US2015/029247 (published as International Publication No. WO2015171614A1) herein incorporated by reference in its entirety. In these embodiments, the wrist assembly is actuated based on the movements of a user (typically a surgeon) who is controlling the robotic device disclosed in International Patent Application No. PCT/US2015/029247. In these embodiments, the surgeon's or user's arms movements are tracked via a sensor tracking system. In one embodiment, a plurality of sensors are attached to the surgeon's arms. In one embodiment the sensor utilized is an MPU-6050 sensor, which includes a MEMS gyroscope, accelerometer, and digital motion processor to compute the orientation of the sensor. In some embodiments, a sensor is affixed to the right and left index finger, or other fingers, hand dorsum and forearm of the user. In further embodiments, additional sensors are affixed to the user/surgeon's arms at different locations, including the upper arm, on the elbow of the user, while in other embodiments sensors are placed on the body of the user, including but not limited to the user's chest, torso or head. In some embodiments the sensor enclosures contain a microcontroller, battery, and Bluetooth module. Position and orientation data from the distal sensors on the user's arms are collected using 12C protocol along wires and transmitted to a computer. With data from the sensors affixed to the user's arms, the computer is able to compute the position and orientation of each portion of the user's arm. In other embodiments, the addition of a MEMES magnetometer with each accelerometer, gyroscope, and motion processor unit. MEMS chips such as MPU-9250 offer all of the above in a single package. The addition of a magnetometer is standard practice in the field, as the magnetic heading allows for the reduction in sensor drift about the vertical axis. In alternative embodiments, sensors are placed in surgical material such as gloves worn by the surgeon, surgical scrubs, or a surgical gown. These sensors may be reusable or disposable.

As alluded to above, in additional embodiments, additional sensors are used to track the position of the surgeon's arms and body. In these embodiments, sensors similar to the sensors in the Xbox Kinect® allow tracking of the absolute position of the user's arms and tracking of the arms positions relative to each other. In some embodiments, these additional sensors are worn on the surgeons' body, while in other embodiments, sensors are positioned at fixed locations in the room.

In yet further embodiments, sensors are found in hand controllers held by the user. In these embodiments, the sensors are used to control the robotic device with the movement of the user's hands. In these embodiments, a sensor tracking system is used to monitor, record and transmit data from the sensors to a computer containing a control loop, with said control loop driving the actuators controlling the robotic device, including the wrist assembly. In one embodiment, magnetic tracking us used in order to obtain position and orientation data of the user. In some embodiments, known magnetic tracking and sensor systems from companies such as Polhemus® and/or Northern Digital Inc.® are utilized, while in other embodiments, other known magnetic tracking and sensors on the market and known in the field are used. Additionally, in some embodiments, the aforementioned magnetic tracking and sensor systems are utilized to track the user's arms and body.

In one embodiment, a magnetic transmitter or source is located within the operating theater, acting as a ground reference, which sends out an electromagnetic dipole field. The magnetic transmitter is connected to electronic control unit that generates the magnetic field and computes position and orientation data from sensors. The user wears a sensor, which can be located on any part of the user's body such as the chest, or head. The sensor worn by the user receives the electronic magnetic field from the transmitter and sends an electric current to the electronic control unit, providing data regarding the position and orientation of the sensor in relation to the transmitter. The raw position and orientation data obtained from the electronic control unit is then transmitted to a central computer connected to the unit, where the data is processed through software that computes the position and orientation of user's body. In addition, the sensor(s) located on the hand controllers, are also operatively coupled to the electronic control unit, with said sensor(s) receiving the electromagnetic field from the transmitter and sending an electrical current from the sensor to the electronic control unit, providing data regarding the position and orientation of the controller in relation to the transmitter. The data from the sensors on the controller go through the same process described above for the sensor worn by the user. With the data from the sensor worn by the user and the data from the sensors on the controller, the central computer is able to infer the position and orientation of the controller in relation to the user's body, thus providing the position and orientation of the user's hand. The position and orientation data inferred by the computer is routed to a control loop which drives the actuators of the robotic arms, such that as the user moves his or her arm, the robotic arm follows and mimics the movement, allowing the user to control and manipulate the robotic arm(s).

In yet other embodiments, the user's arms and body and/or controller is tracked utilizing an optical tracking system. In some embodiments, multiple cameras are strategically placed in the operating room/theater at various locations, while in other embodiments a single camera is used. Each of the cameras contains an infrared (IR) pass filter in front of the lens, and a plurality of IR LEDs around the lens to regularly illuminate the measurement space with IR light. Located on the controller and/or the user's arms and body are retro-reflective markers which reflect the incoming IR light back to the cameras. The cameras detect the IR reflections from the markers and are internally processed by the optical tracking system. In these embodiments, outside-in tracking is used to determine position and orientation of the user and the controller. The optical tracking system determines the two-dimensional positions of the markers in image coordinates, and with the utilization of multiple cameras, the three-dimensional position of each marker can be derived. The three-dimensional position can be measured using a single marker in the measurement space. In addition, the orientation of the controller and/or the user's arm and body can be measure by utilizing multiple cameras, as well as allowing for multiple objects to be tracked simultaneously. In order to accomplish this, multiple cameras are placed around the operating theater, with multiple markers placed on each object to be tracked, such as the controller, the user's arm and body, amongst other items. In other embodiments, inside-out tracking is used, with retro-reflective markers or light houses are placed at stationary locations around the operating room/theater, and/or on other objects, including equipment found in the operating room. In these embodiments, cameras are affixed to the user body and arms and/or hand controller, with said cameras sending out IR light and the retro-reflective markers reflecting the light back on the camera(s) located on the user's arms and body and/or hand controller, thus providing position and orientation coordinates that can be used to derive the position and orientation of the user's arm.

In alternative embodiments, other means and methods of position and orientation tracking are contemplated, including but not limited to, acoustic tracking, and optical tracking without markers. Additionally, in some embodiments, a combination of the above-detailed tracking systems and methods are used in order to obtain position and orientation of a hand controller, as well as the body and arms of the user. In these embodiments, sensor fusion is utilized, with various data being obtained from a variety of sensors and tracking system, with said data being processed through software on a computer to correct any deficiencies of any of the individual sensors in order to calculate accurate position and orientation information.

As detailed above, the wrist assembly is fabricated to follow the movements and motions of the wrist of the user driving a robotic device to which the wrist assembly is coupled. In different embodiments of the wrist assembly, different control methods, and systems are used, to actuate the wrist assembly. This is due different embodiments of the wrist assembly having different components and cables being routed differently.

With the ability to track the user's arms, body, and/or controller, a control loop within the computer drives the actuators controlling the robotic device, which includes the wrist assembly. In these embodiments, the wrist translations of the user are scaled down such that the wrist assembly follows the position of the human wrist and/or the controller held by the user. The wrist translations are scaled down due to difference in size between the wrist of the user and the wrist assembly. Additionally, the wrist assembly is configured to follow the orientation of the user's wrist during actuation, such that, for example if the user rotates their wrist 90 degrees, the wrist assembly will rotate 90 degrees about the appropriate axis. The control scheme for the wrist assembly is further detailed below.

The wrist assembly is configured to provide a surgeon with an assembly that has four (4) degrees of freedom (DOF), which allows a surgeon to emulate the wrist motion of the human arm. Additionally, as detailed above, in some embodiments, the wrist assembly is cable driven. In some embodiments, four cables are utilized to obtain three (3) of the DOFs, with two additional cables being utilized to obtain the fourth DOF. In alternative embodiments, three cables are utilized to control two of the DOFs, with the remaining two DOFs controlled by two cables each.

In some embodiments, the three DOFs are obtained by adjusting the length of the four cables, by pulling in on a specific cable, decreasing the length of that cable or letting out on a specific cable, increasing the length of that cable. The pulling in or letting out on a specific cable either compensates, counteracts and/or counterbalances the amount pulled in or let out on one or more of the other cables, depending on the desired motion. As further detailed below, different control methods are used in different embodiments.

As mentioned above, in one embodiment the rotation and/or actuation of the wrist assembly 100 is achieved by the pulling in and letting out on each of the cables 181, 182, 185, and 191. The pulling in and/or letting out on the aforementioned cables, and thus the change or non-change in the length of the cables, controls the rotation of the first jaw 103 and the second jaw 104 about the jaw axis 189, as well as the rotation of the jaw assembly 101 about the pitch axis 188.

As mentioned above, the wrist assembly 100 is configured to provide two DOFs in the form of two independently moving jaws, one DOF in the form of a jaw assembly that pitches about an axis and an additional DOF in the form of an assembly that rolls about an axis. In addition, with the first and second jaws configured to move independently of each other, the wrist assembly 100 furnishes jaws that can apply a gripping force that can be increased and/or decreased to desired amount, thus allowing a surgeon to perform delicate tasks, as well as more robust tasks. Furthermore, with the first and second jaws configured to move independently, said jaws can be simultaneously actuated in the same direction, with said actuation effectuating a yaw rotation of the jaws.

Figure 19A:
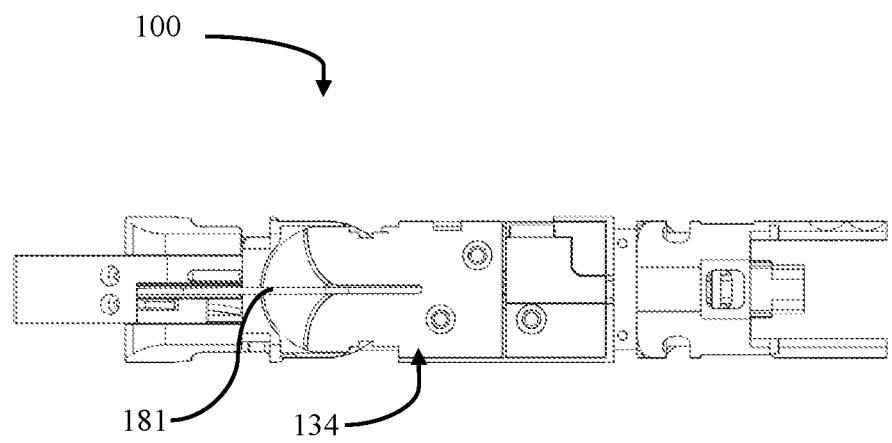
FIG. 19A is a top profile view of a wrist assembly illustrating cable routing of said assembly according to one embodiment.
Figure 19B:
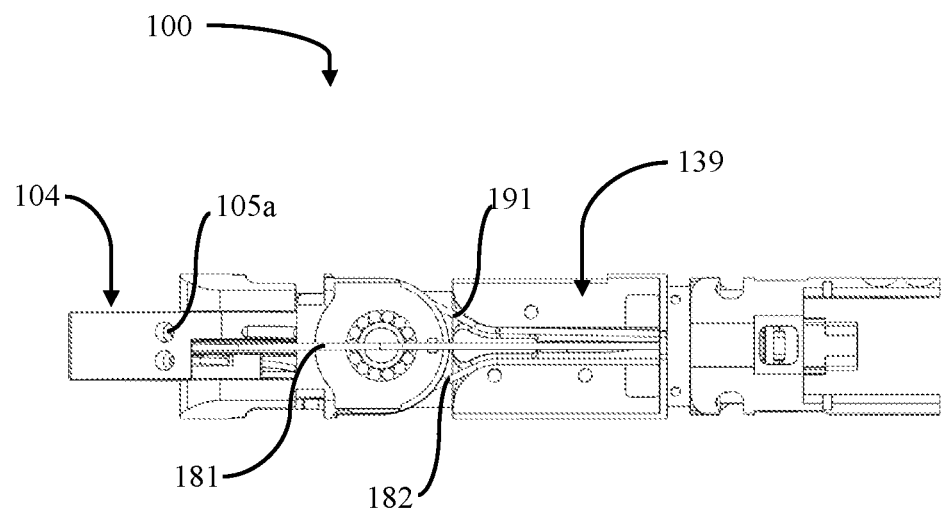
FIG. 19B is a cutaway view of a wrist assembly illustrating cable routing of said assembly according to one embodiment.
Figure 19C:
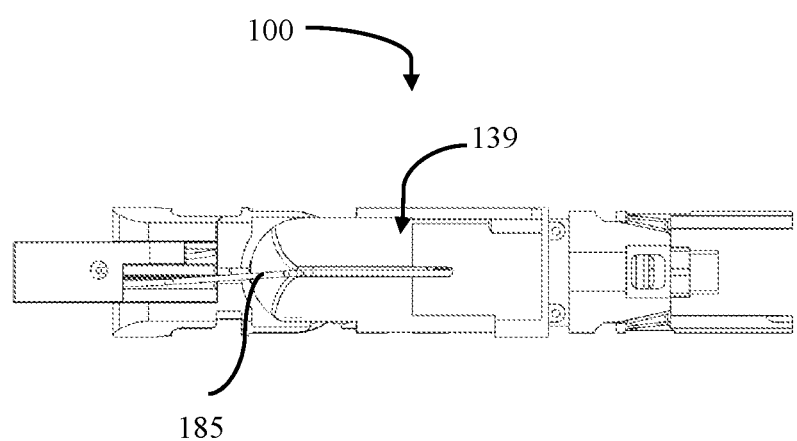
FIG. 19C is a top profile view of a wrist assembly illustrating cable routing of said assembly according to one embodiment.
Figure 19D:
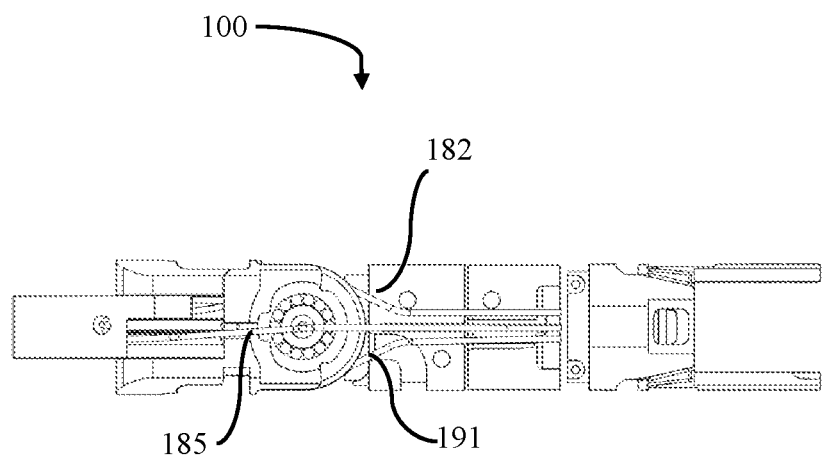
FIG. 19D is a cutaway view of a wrist assembly illustrating cable routing of said assembly according to one embodiment.
Figure 20A:
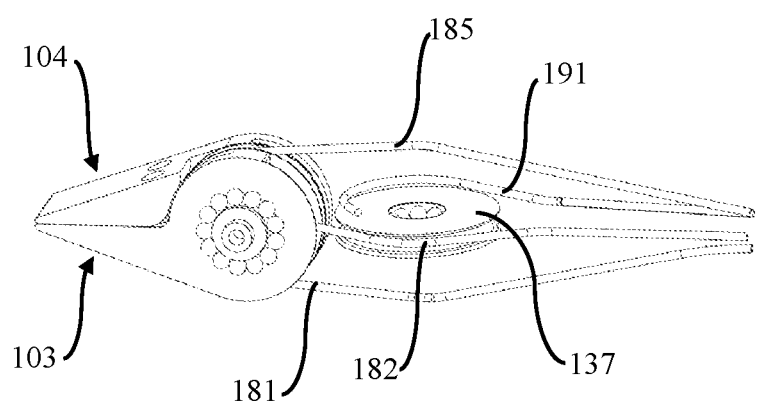
FIG. 20A shows a first jaw and a second jaw with cables attached illustrating the routing of cables according to one embodiment.
Figure 20B:
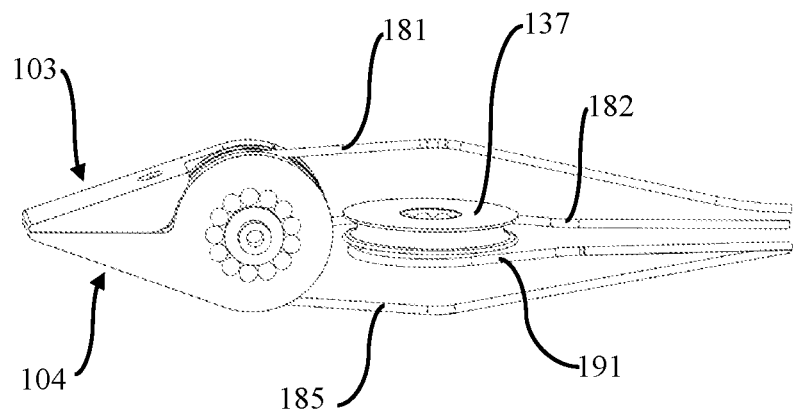
FIG. 20B is an additional view showing a first jaw and a second jaw with cables attached illustrating the routing of cables according to one embodiment.

FIGS. 19A-19D, shows multiple views of an illustrative embodiment of a wrist assembly 100, highlighting the routing of cables 181, 182, 185 and 191, through the wrist assembly 100. FIG. 19A shows a top profile view of an illustrative wrist assembly 100, highlighting the routing of cable 181 through the cable routing slot of the female hinge body or hinge cover 134. FIG. 19B shows a cut-away view of the wrist assembly 100 with the female hinge body removed, so as to highlight the routing of cable 182 and cable 191. As seen in FIG. 19B, cables 182 and 191 are routed through the inner surface of the male rotary-hinge body or hinge-rotary body 139. FIG. 19C shows an additional top profile view of the wrist assembly 100, highlighting the routing of cable 185 through the cable routing slot of the male rotary-hinge body or hinge-rotary body 139. FIG. 19D shows a cut-away view of the wrist assembly 100 with the male rotary-hinge body removed, so as to highlight the routing of cables 182 and 191.

Figure 21A:
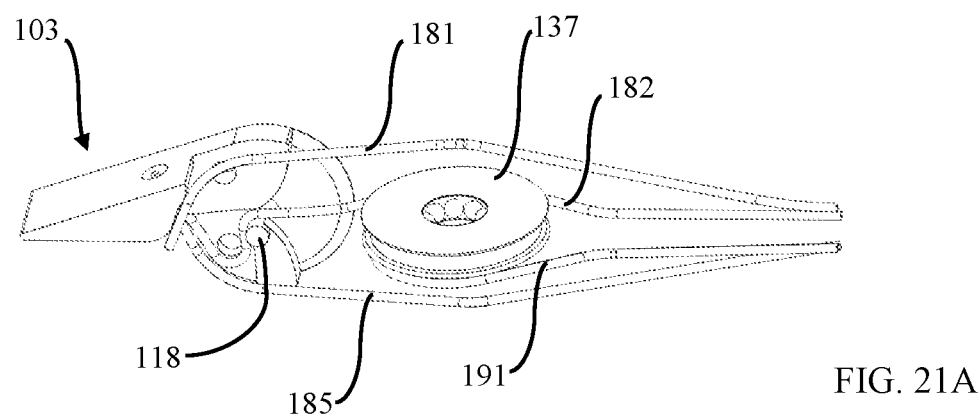
FIG. 21A shows a first jaw illustrating the routing of cables to said jaw according to one embodiment.
Figure 21B:
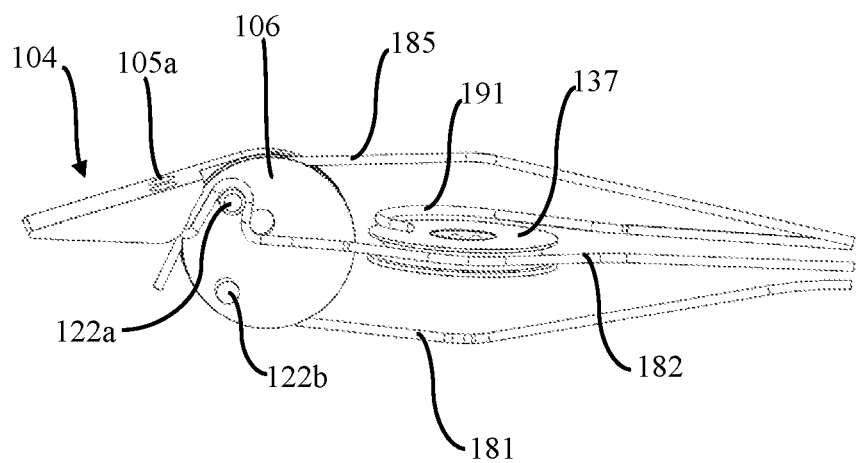
FIG. 21B shows a second jaw illustrating the routing of cables to said jaw according to one embodiment.

In some embodiments, the second jaw 104 is configured to rotate about the jaw axis 189 (FIG. 18), in a first and second direction, with said rotation being independent from the first jaw 103. In these embodiments, the second jaw 104 is configured to move between a first and second position, with said positions, including but not limited to an open and closed position. In one embodiment, the second jaw 104 is actuated in a first direction, said direction including but not limited to rotation of the second jaw 104 towards the first jaw 103. FIG. 21B, is an illustrative cabling diagram, highlighting how cables are routed to the second jaw 104 according to one embodiment. As detailed above, and depicted in FIG. 19B, in one embodiment, cable 181 is routed through the hinge-rotary assembly and through the jaw assembly to cable termination site 105a located on the second jaw 104, where cable 181 terminates. In order to actuate the second jaw 104 in a first direction, cable 181 is pulled in via an actuator causing the second jaw 104 to start to rotate about the jaw axis 189 in a first direction. As the second jaw 104 starts to rotate, slack of cable 182 is let out, thus increasing the operative length of cable 182. The operative length of the cable is the distance between the connection pin 122a and the second jaw 104 as defined by the path of cable 182. The increase and/or decrease in the operative length of cable 182 results in movement of a jaw in either a first or second direction relative to the other jaw. The ball bearing set 109 which sits on bearing race 116a of the actuation hub 180 of the second jaw 104, and also sits on bearing race 127 of the hinge flex body 107, allows the second jaw 104 to rotate about the jaw axis 189. Since cable 181 terminates at termination site 105a located on the second jaw 104, the pulling in on cable 181 by the actuator is transferred on to the second jaw 104 resulting in said jaw rotating about the jaw axis 189 in a first direction. In the above scenario, if it is desired to fix the position of the first jaw 103 the length of cable 185 and cable 191 is held constant so as to prevent the first jaw 103 from moving. However, in other scenarios, the length of cables 185 and 191 is either lengthened or shortened thus allowing the first jaw 103 to rotate in a first or second direction, while the second jaw 104 also rotates.

Figure 21C:
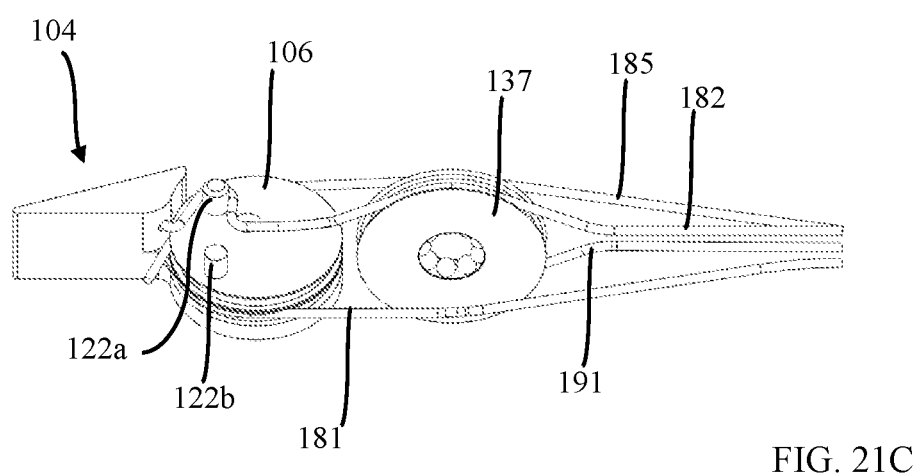
FIG. 21C shows a first jaw illustrating the routing of cables to said jaw according to one embodiment.

As mentioned above, the second jaw 104 is configured to be actuated in a second direction as well, with said second direction being opposite the first direction. In order to actuate the second jaw 104 in a second direction, cable 182 is pulled in, resulting in the operative length of cable 182 decreasing. As seen in FIG. 21C, cable 182 is routed around connection pin 122a and terminates on the second jaw 104. In this scenario, when cable 182 is pulled in, the operative length of said cable decreases, and thus the second jaw 104 rotates in the second direction relative to connection pin 122a and thus relative to the first jaw 103. As cable 182 pulled in, slack from cable 181 is released, thus allowing the second jaw 104 to rotate in a second direction relative to connection pin 122a and thus relative to the first jaw 103. Additionally, the length of cable 191 is held constant to prevent any unwanted movement about the pitch axis 188. In addition, the length of cable 185 is held constant, to constrain the first jaw 103 in a fixed position, allowing the second jaw 104 to move in the second direction independently of the first jaw 103.

Similarly, the first jaw 103 is also configured to move independently in a first and second direction about the jaw axis 189. In order to actuate the first jaw 103 so that said jaw rotates about the jaw axis 189 in a first direction, cable 185 is pulled in on via an actuator, causing the first jaw 103 to start to rotate. As the first jaw 103 starts to rotate in the first direction, slack from cable 182 is released, thus increasing the operative length of cable 182. As cable 182 passes through the wrist assembly 100 it is routed over the decoupling surfaces 195 and 194 detailed above, which are configured to enable adequate decoupling of the motion of cable 182 from other joints and/or cables. Furthermore, this decoupling of motion prevents cable 182 from imparting a force on the rest of the wrist assembly 100. The surfaces that cable 182 is routed about and/or through are configured to reduce the change in length of said cable, but cannot fully eliminate the length change. Any unwanted length change is corrected via sensors and control algorithms. The ball bearing set 109 which is sits on bearing race 116b of the actuation hub 184 of the first jaw 103, as well as on hinge bearing race 127 of the hinge non-flex body 108, allows the first jaw 103 to rotate about the jaw axis 189. Since cable 185 terminates at termination site 105b located on the first jaw 103, the pulling in on cable 185 by the actuator results in said jaw rotating about the jaw axis 189 in a first direction. To independently move the first jaw 103 cables 191 and 181 are held constant.

The first jaw 103 is also configured to rotate about the jaw axis 189 in a second direction independently of the second jaw 104, with said second direction being opposite the first direction. In order to rotate the first jaw 103 about the jaw axis 189 in the second direction, cable 182 is pulled in by the actuator it is coupled to. The operative length of cable 182 decreases resulting in the first jaw 103 rotating in a second direction relative to the second jaw 104. In addition, in order to rotate the first jaw 103 independently in a second direction, cable 181 is held constant in order prevent elongation of said cable. Inhibiting the elongation of cable 181 prevents the second jaw 104 from rotating about the jaw axis 189 in a second direction. Furthermore, as the first jaw 103 rotates about the jaw axis 189 in the second direction, slack is released from cable 185, allowing the first jaw 103 to rotate in the second direction, and cable 191 is held constant to prevent any unwanted movement of the jaw assembly 101 about the pitch axis 188.

Correspondingly, with the first and second jaws configured to move independently, said configuration allows the jaws to be simultaneously actuated so that the jaws rotate about the jaw axis 189 together in either a first and/or second direction. This actuation effectuates a yaw movement of the jaws. In order to rotate the first and second jaws about the jaw axis 189, while keeping both jaws in a constant position relative to each other, cable 182 is held constant so there is no change in length. With cable 182 at a constant length, cable 181 is pulled on and slack from cable 185 is let out the same amount, with the change in lengths of the cables counteracting each other and thus rotating the jaws in a first direction. To rotate the jaws in the second directions, cable 185 is pulled in and slack from cable 181 is let out, with the change in length of the cables counteracting each other. For example, with the jaws orientated in the same position shown in FIG. 18, if a surgeon wishes to rotate the jaws about the jaw axis 189 in a first direction, with said first direction being rotation of the jaws towards the top of the page, cable 181 would be pulled in and the same amount pulled in on cable 181 would be let out on cable 185. Similarly, taking the example above, if a surgeon wanted to rotate the jaws in a second direction, with said second direction being rotation of the jaws towards the bottom of the page, cable 185 would be pulled in and the same amount pulled in on cable 185 would be let out on cable 181.

Furthermore, with the first and second jaws configured to move independently of each other, said configuration also allows a surgeon to apply a force with the jaws, with said force being variable, thus allowing a surgeon to control the amount of force applied by the jaws. With the ability to control the amount of force being applied by the jaws, a surgeon is able to complete a myriad of tasks, such as tissue manipulation, as well as grasping a surgical instrument or tool. The amount of force being applied by the jaws is determined by the amount length pulled in or let out on cables 181 and 185. In order to apply a force with the jaws, slack of cable 182 is released, with cable 182 wrapping around pin connection 122a. A o cable 181 is pulled in causing the second jaw 104 to move towards the first jaw 103, while simultaneously pulling in on cable 185 causing the first jaw to move towards the second jaw 104. With the first and second jaws grasping an object, additional force can be applied via the jaws by pulling in more on cables 181 and/or 185. Similarly, to decrease the force being applied by the jaws, slack is let out on cables 181 and/or 185.

As mentioned above, the wrist assembly 100 is also configured to allow the jaw assembly 101 to rotate about the pitch axis 188 in a first and second direction. In order to rotate the jaw assembly 101 about the pitch axis 188 a combination of cables are pulled in and/or let it out, with the amounts being pulled in and/or let out on each cable varying, so as to counteract the amount being pulled in or let out on a different cable. In one embodiment, in order to rotate the jaw assembly 101 about the pitch axis 188 in a first direction, the length of cable 185 and cable 181 are held constant. Holding the length of the aforementioned cables constant, keep the jaws in a constant position, with sensors being used to counteract any undesired movement of said jaws. In addition, cable 191 is pulled in, thus shortening the length of cable 191. As detailed above, cable 191 is routed through the hinge-rotary assembly 102 and terminates at cable termination site 131 located on the proximal end of the hinge non-flex body 108. The decrease in the length of cable 191 imparts a force on the hinge non-flex body 108, at cable termination site 131, with said force causing the jaw assembly 101 to rotate about the pitch axis 188 in the first direction. As the length of cable 191 decreases, the length of cable 182 lengthens and wraps around the idler pulley 137. Thus cable 191 and 182 act together so as to allow the jaw assembly 101 to be rotated about the pitch axis 188 in a first direction, at the election of the surgeon. The rotation of the jaw assembly 101 about the pitch axis 188 in a second direction, with said second direction being opposite the first direction is accomplished by pulling in and/or letting out on a combination of cables, with said pulling in and/or letting out on cables counteracting the pulling in and/or letting out on other cables. In one embodiment, slack of cable 191 is released thus increasing the length of cable 191. As the length of cable 191 increases, cable 182 is pulled in thus decreasing the length of cable 182. As the length of cable 182 decreases, it unwraps from the idler pulley 137, resulting in the rotation of the jaw assembly in the second direction.

In other embodiments, cables 181, 182, and 185 pass through the hinge-rotary assembly, and an additional cable is terminated on the hinge flex body. In these embodiments, the additional cable works in conjunction with cable 191 to control rotation of the jaw assembly about the pitch axis in a first and second pitch direction. In alternative embodiments, a combination of cables 181, 182, and 185 are used in opposition to cable 191 to control the rotation of the jaw assembly about the pitch axis in a first and second pitch direction. In these embodiments, the remaining cables which are not used in opposition of cable 191 are non-opposing cables which pass through the hinge-rotary assembly without imparting additional torques about the joint. In these embodiments, the first pitch direction is rotation about the pitch axis in one direction, with the second pitch direction being rotation about the pitch axis in the opposite direction of the first direction.

As mentioned above, in different embodiments, the wrist assembly comprises magnets that are used to obtain position and orientation data of said assembly as it rotates about an axis. In these embodiments, the magnets are diametrically magnetized, such that as the magnet rotates about its cylindrical axis its magnetic field changes. In these embodiments, the change in the magnetic field is measured by the sensors, with said sensors transmitting the data to processors which convert the change in magnetic field to rotational position data. This conversion is done with knowledge of the physical configuration of the magnets(s), and sensor(s). In some embodiments, several sensors are placed around the diametrically magnetized magnet orthogonally to each other. As the diametrically magnetized magnet rotates the magnetic field it generates also changes relative to the sensors. The change in magnetic field is transmitted to a computer via electrical communication components, such as PCBs or FPCBS. The computer takes the data obtained from the magnet regarding the change in the magnetic field and converts it into a degree of rotation. Using simple trigonometry, a combination of two orthogonally placed sensors can determine the direction of the magnetic field by comparing the relative field strength between the sensors. This calculation yields the orientation of the diametrically magnetized magnet, and by extension, the orientation of the wrist assembly as it is actuated about an axis. Additional sensors are placed in this embodiment for redundancy, but the total number of sensors necessary for the absolute orientation calculation will depend on the chosen configuration of the magnet and sensors.

In some embodiments, the magnet configured as a cylindrical magnet, while in other embodiments, a horseshoe magnet, disc magnet, sphere magnet, and/or other magnets shapes known in the art. In different embodiments a variety of sensors known in the art that are capable of magnetic field sensing can be used, including but not limited to hall effect sensors, and/or magnetoresistors.

The sensors detailed above are continuously transmitting position and orientation data to a central computer, that processes the data and sends command prompts to the actuators of the wrist assembly in order to adjust the force being applied to or the position of the cables so as to correct for any undesired movement of the wrist assembly.

Actuation Control of Wrist Assembly

As mentioned above, sensors are used to determine the orientation of the wrist assembly during actuation about the pitch axis, jaw axis and roll axis. In these embodiments, the first jaw and second jaw each have an independent sensor that reads the angular rotation of the individual jaw about the jaw axis. In some embodiments, the sensor(s) for the first jaw are located on the hinge non-flex body, with the sensor(s) for the second jaw located on the hinge flex body. The sensors detailed above for the first and second jaw are used in conjunction with each other to determine the average angle of the first jaw and second jaw about the jaw axis referred to herein as the angle of the wrist joint, as well as the angle between the first jaw and second jaw about the jaw axis, referred herein as the angle of the jaw joint.

In order to determine the aforementioned angles of the joints, the sensors for each independent joint of the wrist assembly are calibrated to zero out the individual angles and ensure one-to-one mapping between physical motion and sensed motion. In some embodiments, each independent joint is moved through its range, and an external sensor that is already calibrated is used to record actual joint angles as the sensors collect their own sensed angles simultaneously. Standard calibration procedures known in the art may be used to calibrate the sensors to best match the sensed angles by the external sensors. Examples of calibrations include setting constant offsets, constant scaling factors, and variable offsets or scaling factors to a given sensor that are based on the positions of other sensors.

In some embodiments where a sensor cannot sense the full range of its joint with unique sensor readings, a multi-turn algorithm may be used to keep track of the absolute position of the joint, similar to how an incremental encoder can track an arbitrarily large range with only a few possible sensor readings. Any multi-turn or similar algorithm known in the art may be used for this purpose. An example of one possible algorithm is described here: at each time-step of the algorithm, the sensed joint angle is compared to the previously measured joint angle. (For the first iteration of the algorithm, the previously measured joint angle is set to the sensed joint angle.) If these two angles differ by more than half of the sensor range, then it is assumed this large jump in angle is actually a result of the sensed angle passing through a discontinuity in the sensor (for example there may be a discontinuity between sensing −180 degrees and 180 degrees). In this example, the sensed joint angle may change from −175 degrees to +178 degrees in a given time-step. When this large angle change is detected, the algorithm appropriately adds or subtracts the full range of the sensor from the sensed joint angle until the difference between the sensed angle and previous angle is less than half of the sensor range. (In the above example, the sensed joint angle would be modified to be 178−360=−182 degrees, making the difference between the previous joint angle and newly-computed sensed joint angle −175−(−182)=7 degrees.) The previously sensed joint angle is then updated with the newly-computed sensed joint angle for the next iteration of the algorithm. In some embodiments, a low-pass filter may be used to filter the previously sensed joint angle so that sensor noise or other fast changes in sensed angle are not mistaken for passing through a sensor discontinuity.

Once the joints of the wrist assembly are properly calibrated thus providing accurate readings of the orientation of the joints, the wrist assembly is ready to be actuated. As mentioned above, the cables which actuate the jaws and the wrist assembly are operably coupled to actuators which drive the cables and thus actuate the wrist assembly. In different embodiments a variety of actuators could be used, including but not limited to servomotors, rotary actuators, linear actuators and/or stepper motors.

As mentioned above, electrical communication components are utilized to transmit position and orientation data to a computer which processes said data and transmits control commands and/or prompts to the actuators which apply position changes to the cables in order to actuate the jaws and wrist assembly in a desired manner. In one embodiment, the actuators are controlled in position-control mode to pull the cables by various amounts in order to control the jaw joint, the wrist joint and the rotation of the wrist assembly about the pitch axis, which herein is referred to as the pitch joint. In alternative embodiments, the actuators are controlled using actuator torque, winding current, voltage and/or angular velocity. Other actuation methods known in the art may alternatively be used. In yet other embodiments, some combination of control modalities may also be used for the various actuators. For example, an agonist actuator may pull on a cable using force control, while the antagonist actuator for the same joint may drive its cable with position control.

In some embodiments that use actuator position control, total motion of the cables of the wrist assembly is a superposition of the respective cable motions for each of the three joints (wrist joint, jaw joint, and pitch joint). The cable positions for each joint is added to the cable positions from other joints to determine the net desired position of the cables.

For the embodiments of wrist assembly 100, assuming constant moment arms of all cables on all joints, the numbers in the Table 1 below, indicate units of cable position as enforced by the appropriate actuator in order to affect the given joint angle by a given amount.

In one embodiment, the values in Table 1 indicate the position, or change in position applied to each cable, as pulled in by the appropriate actuator, in order to achieve a given joint angle or change in joint angle (radians). Negative values indicate that the given cable should be let out, rather than pulled in by the given actuator. The units of the values in the table are therefore millimeter per radian (mm/rad). Different embodiments of robots may have different combinations of table values and be adjusted accordingly based on the control mode utilized and/or the size of the components of the assembly.

TABLE 1

Wrist Assembly 100

| Joint Index (Positive Direction) | Cable 182 | Cable 191 | Cable 185 | Cable 181 |
|---|---|---|---|---|
| Pitch Joint (rotation about Pitch Axis 188) | +5 | −5 | 0 | 0 |
| Wrist Joint (rotation about Jaw Axis 189) | 0 | 0 | +5 | −5 |
| Jaw Joint (Opening of Jaws about Jaw Axis 189) | +5 | 0 | −2.5 | −2.5 |

To control a given joint, a standard control system utilizing any combination of standard feedback and feedforward control techniques is used including but not limited to PID, lead-lag, LQR, H-infinity, Model-predictive, sliding mode, model-reference adaptive control, neural-network based control. This control system generates an error signal based on the set value of the joint angle (from human input, or other input) and the sensed joint angle. The controller takes this error signal and produces a control effort which represents how hard the joint will attempt to drive toward the desired position from the current position. In some embodiments, the control effort is represented as a change in joint angle. In some embodiments, other information about robot state may be used in the control system. This control effort is then multiplied by the values in the above table to compute the desired cable length or cable length change driven by the individual actuator, so the joint reaches the desired position. In some embodiments, these length changes are referenced to an initial cable position (or actuator angle) that is recorded during initialization.

As an example, in order to open the first jaw and the second jaw, such that each jaw rotates about the jaw axis 189, to make the jaw open by 1 radian, cable 182 is pulled in 5 mm, while 2.5 mm length of cable 185 and cable 181 is let out If the table has a "0" indicated for a cable, that means that the cable is held constant for the given joint. Cables 185 and 181 both act in opposition of cable 182 and therefore cables 185 and 181 only need to let out half as much cable as taken in by cable 182, for a given angle of motion for the jaw joint. If the moment arm of a cable on a joint is not equal to the other moment arms, the scaling in the above table is adjusted appropriately. By way of example, if the moment arm for cable 182 was double the moment arms of cables 185 and 181, cable 182 would be pulled in 10 mm/radian, while cables 181 and 185 would still let out 2.5 mm/radian each. In order to move a joint in the opposite direction of what is shown in the table above, the sign of the number as indicated in the table would be reversed. In different embodiments, different actuator control modes, such as torque, velocity or other control modes can be used.

In these different embodiments, the values indicated in the table above are adjusted based on the actuator control mode used.

Figure 34A:
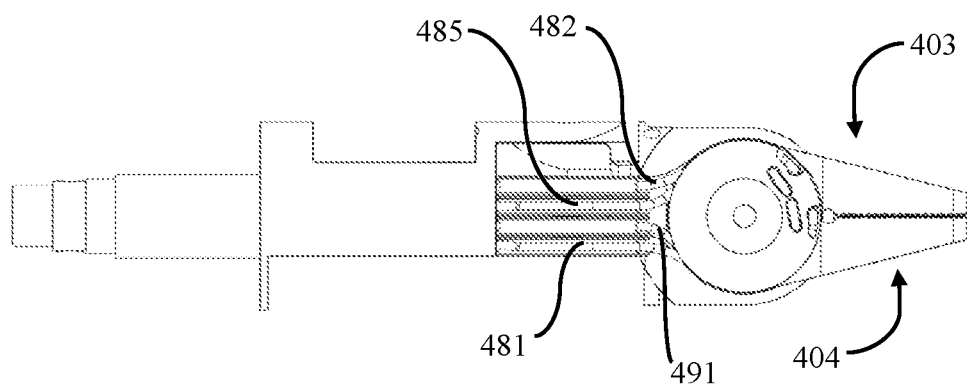
FIG. 34A shows a side cutaway view illustrating cable routing to a first and second jaw according to one embodiment.
Figure 34B:
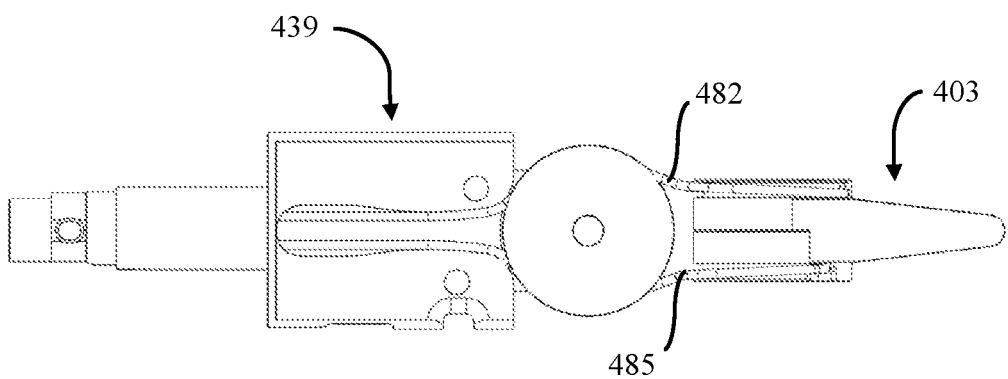
FIG. 34B shows a top cutaway view of cable routing according to one embodiment.
Figure 34C:
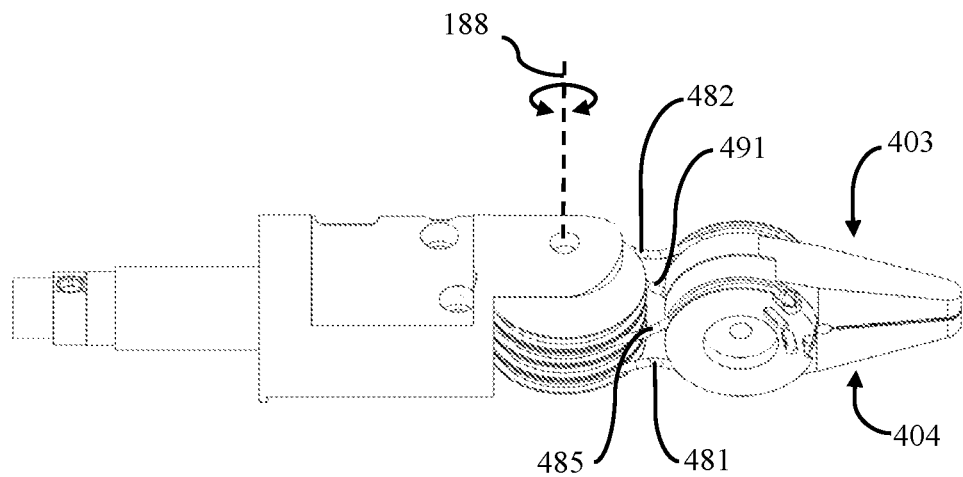
FIG. 34C shows an isometric view of cable routing to a first and second jaw according to one embodiment.
Figure 34D:
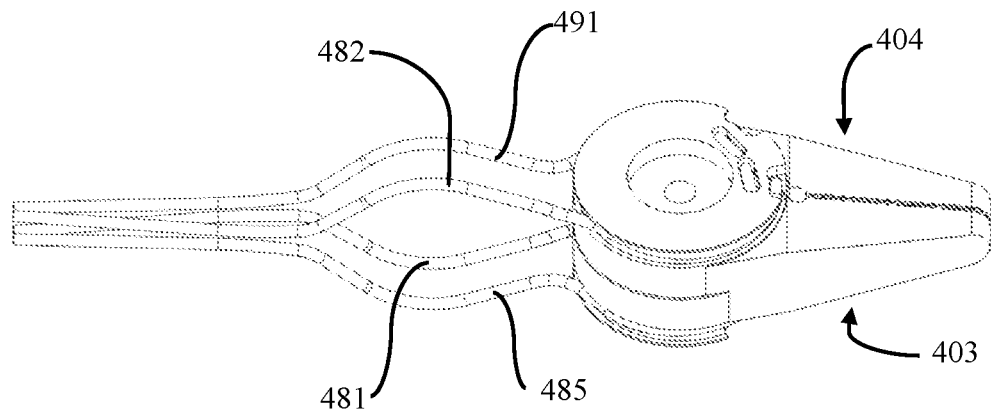
FIG. 34D shows an isometric view of cable routing to a first and second jaw according to one embodiment.

In some embodiments, the cables of wrist assembly 100 are controlled such that some component of their positions, forces or other controlled quantities are independent of the opposing cable or cables. This type of control strategy includes, but is not limited to, starting to pull on one cable before or after the opposing cable starts to let out when changing direction, and including an increased or decreased preload added to all of the cables that control a given joint during certain circumstances. In some embodiments of wrist assembly 100, the cables may be controlled so that some component of their positions, forces, or other controlled quantities are independent the opposing cable or cables. This type of control strategy includes but is not limited to: starting to pull on one cable or pair of cables before or after the opposing cable or pair of cables starts to let out when changing direction and including an increased or decreased preload added to all cables that control a given joint during certain circumstances. Constant or variable scalings may be combined with the above table so that some cables are pulled or let out faster than the opposing ones, in order to provide a tighter or looser control of the joints. Offsets may also be added to the cable or cable-pair positions to provide for controlled amounts of slack Similar to wrist assembly 100, position control is used in some embodiments of wrist assembly 400 to control the actuation about the different axes. In these embodiments, all of the cables that are routed to the first and second jaws are routed internally through the hinge-rotary assembly and the jaw assembly. FIG. 34B shows the routing of cables 482 and 485 through the hinge-rotary body, according to one embodiment. In addition, in these embodiments, the actuation of the control of the wrist assembly is different due to the different routing of the cables through the assemblies. As stated above, two cables terminate on each of the jaws. In these embodiments, the pair of cables that terminate on the first jaw are situated on the same side of the pitch axis 188, with the pair of cables that terminate on the second jaw situated on the opposite side of the pitch axis as seen in FIG. 34C. In these embodiments, one of the two cables that terminate in each jaw is utilized to open the jaw with the second cable utilized to close the jaw. In the illustrative embodiment shown in FIG. 34A, cables 482 and 491 are the pair of cables used to open and close the first jaw 403, with cable 482 utilized to open the first jaw (i.e., that is move away from the second jaw) and cable 491 is utilized to close the first jaw (i.e., that is move towards the second jaw). In the embodiments shown in FIGS. 34A-34D, in order to open the first jaw 403 independent of the second jaw 404, cable 482 is pulled in by the actuator, while the letting out the same amount of cable length on the cable 491. In addition, the cables for the second jaw are held constant. The same technique detailed above for opening one jaw independently of the other jaw, is used to close one jaw independently of the second jaw. For example in the embodiments shown in FIGS. 34A-34D, in order to close the first jaw, cable 491 is pulled in, while the same amount of length of cable 482 being let out, and cables 481 and 485 being held constant.

In these embodiments of wrist assembly 400, assuming constant moment arms of all cables on all joints, each joint is controlled by pulling on a pair of cables while letting out the remaining pair of cables by the same amount. Table 2 below indicates the amounts to pull on cables in order to provide a desired motion in a given joint, for some embodiments of wrist assembly 400. Signs indicate which way a cable should move to cause output joint motion in the positive direction; positive refers to pulling on the cable while negative refers to letting out the cable. In the below table the units are millimeter (mm) per radian (rad). In the table "a" is the radius of the pulleys concentric with the pitch axis, "b" is the radius of the pulleys that are concentric with the jaw axis, and "b/2" is half the radius of the pulleys that are concentric with the jaw axis.

TABLE 2

Wrist Assembly 400

| Joint Index (Positive Direction) | Cable 482 | Cable 491 | Cable 485 | Cable 481 |
|---|---|---|---|---|
| Pitch Joint (rotation about Pitch Axis 188) | +a | +a | −a | −a |
| Wrist Joint (rotation about Jaw Axis 189) | +b | −b | +b | −b |
| Jaw Joint (Opening of Jaws about Jaw Axis 189) | +b/2 | −b/2 | −b/2 | +b/2 |

In some embodiments, the cables may be controlled so that some component of their positions, forces, or other controlled quantities are independent the opposing cable or cables. This type of control strategy includes but is not limited to: starting to pull on one cable or pair of cables before or after the opposing cable or pair of cables starts to let out when changing direction and including an increased or decreased preload added to all cables that control a given joint during certain circumstances. Constant or variable scalings may be combined with the above table so that some cables are pulled or let out faster than the opposing ones, in order to provide a tighter or looser control of the joints. Offsets may also be added to the cable or cable-pair positions to provide for controlled amounts of slack.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

What is claimed is:

1. A wrist assembly comprising:
   a. a jaw assembly comprising:
      i. a first jaw configured to rotate about a jaw axis, the first jaw having a first working segment, a first actuation hub, and a cable redirecting hub operably coupled to the first actuation hub, wherein the first actuation hub comprises a cable passageway and has an outer perimeter, and wherein the cable redirecting hub comprises a redirecting hub cable raceway adjacent to the outer perimeter of the first actuation hub;
      ii. a second jaw configured to rotate about the jaw axis and movably opposed to the first jaw, the second jaw having a second working segment and a second actuation hub, the second actuation hub comprising a first cable raceway disposed along an outer perimeter of the second actuation hub; and
      iii. a housing for the first and second jaws;
   b. a first cable disposed in at least a portion of the first cable raceway and coupled to the second jaw;
   c. a second cable disposed in the cable passageway and coupled to the second jaw;
   d. a third cable disposed in at least a portion of the redirecting hub cable raceway and coupled to the first jaw;
   e. a fourth cable coupled to a first body of the housing of the jaw assembly or to a second body of the housing of the jaw assembly; and
   f. a hinge-rotary assembly coupled to the jaw assembly, configured to provide rotation of the jaw assembly about a pitch axis, configured to rotate about a roll axis, and comprising:
      i. a female rotary body defining a cavity;
      ii. a hinge-rotary body disposed at least partially within the cavity of the female rotary body, the hinge-rotary body comprising a cable conduit, the cable conduit housing at least a portion of one or more of the first cable, the second cable, or the third cable;
      iii. a hinge cover; and
      iv. a decoupling surface located on at least one of the hinge cover or the hinge-rotary body, the decoupling surface configured to allow one or more of the first cable, the second cable, or the third cable to ride along at least a portion of the decoupling surface;
   g. a control system configured to rotate the first jaw, the second jaw, or both about the jaw axis;
   wherein the wrist assembly is configured such that when a first tension is applied to the first cable, a second tension is applied to the second cable, a third tension is applied to the third cable, a fourth tension is applied to the fourth cable, and an opposing tension is applied to an opposing cable:
      where the fist tension is greater than the second tension, a first torque is generated along the jaw axis that causes the second jaw to rotate about the jaw axis in a first direction relative to the first jaw;
      where the second tension is greater than the first tension, a second torque is generated along the jaw axis that causes the second jaw to rotate about the jaw axis in a second direction relative to the first jaw;
      where the third tension is greater that the second tension, a third torque is generated along the jaw axis that causes the first jaw to rotate about the jaw axis in a first direction relative to the second jaw;
      where the second tension is greater than the third tension, a fourth torque is generated along the jaw axis that causes the first jaw to rotate about the jaw axis in a second direct relative to the second jaw;
      where the fourth tension is greater than the opposing tension, a fifth torque is generated along the pitch axis that causes the jaw assembly to rotate about the pitch axis in a first pitch direction; and
      where the opposing tension is greater than the fourth tension, an opposing torque is generated along the pitch axis that causes the jaw assembly to rotate about the pitch axis in a second pitch direction, the second pitch direction being rotation about the pitch axis in the opposite direction of the first pitch direction;
   wherein the control system is further configured to:
   accept data from at least one first rotational position sensor, at least one second rotational positional sensor, or both; and
   determine one or more of the first tension, the second tension, the third tension, the fourth tension, or the opposing tension to cause rotation of the jaw assembly about the pitch axis, the jaw axis, or both.

2. The wrist assembly of claim 1, the hinge-rotary assembly further comprising a rotary pulley body operably coupled to a proximal end of the hinge-rotary body, wherein the hinge-rotary body rotates with the rotary pulley body relative to the female rotary body to provide rotational movement about the roll axis.

3. The wrist assembly of claim 1, wherein the first body of the housing of the jaw assembly and the second body of the housing of the jaw assembly are configured to enable the first jaw and the second jaw to rotate about a jaw axis.

4. The wrist assembly of claim 3, wherein the first body of the housing comprises a first jaw stop and the second body of the housing comprises a second jaw stop, and wherein the first jaw stop and the second jaw stop are configured to prevent one or more of the first jaw or second jaw from rotating past a threshold of rotation about the jaw axis.

5. The wrist assembly of claim 3, wherein the hinge-rotary assembly further comprises at least one idler pulley disposed between the hinge rotary body and hinge cover, the at least one idler pulley idler pulley disposed about the pitch axis and having an idler raceway disposed along an outer perimeter of the at least one idler pulley, and wherein the second cable is disposed in at least a portion of the idler raceway.

6. The wrist assembly of claim 5, further comprising a plurality of bearings, wherein the plurality of bearings is located between one or more of:
   a. the hinge-rotary body and the first body of the housing;
   b. the hinge-rotary body and a male bearing race;
   c. the at least one idler pulley and the first body of the housing;
   d. the hinge cover and the second body of the housing; or
   e. the hinge cover and the male bearing race.

7. The wrist assembly of claim 1, wherein the decoupling surface is further configured such that one or more of the first cable, the second cable, or the third cable riding along at least the portion of the decoupling surface reduces a length change in the one or more of the first cable, the second cable, or the third cable while pivoting about a center of the pitch axis relative to a length change in the one or more of the first cable, the second cable, or the third cable in the absence of the decoupling surface.

8. The wrist assembly of claim 1, further comprising a plurality of first rotational position sensors disposed proximate to the jaw axis.

9. The wrist assembly of claim 1, further comprising at least one first rotational position sensor disposed proximate to the jaw axis and configured to detect rotation of one or more of the first or second jaws about the jaw axis.

10. The wrist assembly of claim 9, further comprising at least one second rotational position sensor disposed proximate to the pitch axis and configured to detect rotation of the jaw assembly about the pitch axis.

11. The wrist assembly of claim 10, further comprising at least one electrical communication component configured to transmit information captured by the at least one first rotational position sensor or at least one second rotational position sensor.

12. The wrist assembly of claim 11, wherein the at least one electrical communication component comprises at least one of a flexible printed circuit board (FPCB) or a printed circuit board (PCB).

13. The wrist assembly of claim 9, comprising a plurality of second rotational position sensors located at the pitch axis.

14. The wrist assembly of claim 1, wherein:
(a) the opposing cable comprises the first cable and the opposing cable tension includes the first cable tension; or
(b) the opposing cable comprises the second cable and the opposing cable tension includes the second cable tension, or
(c) the opposing cable comprise the third cable and the opposing cable tension includes the third cable tension, or
(d) any combination of (a)-(c).

15. The wrist assembly of claim 1, wherein the opposing cable is the first cable, the opposing cable is the second cable, or the opposing cable is the third cable.

16. The wrist assembly of claim 1, wherein the control system further comprises at least one actuator configured to apply a tension to one of the first cable, the second cable, the third cable, or the fourth cable, and
wherein the at least one actuator comprises one or more of a stepper motor, a servo-motor, a hydraulic actuator, a pneumatic actuator, a piezo-electric motor, or an ultrasonic transducer.

17. The wrist assembly of claim 1, wherein the cable redirecting hub and the first actuation hub are of monolithic construction.

18. The wrist assembly of claim 1, wherein the cable redirecting hub comprises a redirecting pin; and
wherein the second cable passes around at least a portion of the redirecting pin within the cable passageway.

19. The wrist assembly of claim 1, wherein the first actuation hub further comprises a first cable routing protrusion; and
wherein the first cable routing protrusion is configured to provide a surface for the second cable to ride along during the rotation of the first jaw about the jaw axis in a first direction.

20. The wrist assembly of claim 19, wherein the first cable routing protrusion is configured to reduce torque along the jaw axis during rotation of the first jaw about the jaw axis in the first direction relative to torque along the jaw axis during rotation of the first jaw about the jaw axis in the first direction in the absence of the first cable routing protrusion.

21. The wrist assembly of claim 19, wherein the first cable routing protrusion is configured to reduce a first length change in the second cable during rotation of the first jaw about the jaw axis in the first direction relative to a second length change in the second cable during rotation of the first jaw about the jaw axis in the first direction in the absence of the first cable routing protrusion.

22. The wrist assembly of claim 19, wherein the first actuation hub further comprises a second cable routing protrusion; and
wherein the second cable routing protrusion is configured to provide a surface for the second cable to ride along during the rotation of the first jaw about the jaw axis in a second direction, the second direction being an opposite direction of rotation relative to the first direction.

23. The wrist assembly of claim 22, wherein the second cable routing protrusion is configured to reduce torque along the jaw axis during rotation of the first jaw about the jaw axis in the second direction relative to torque along the jaw axis during rotation of the first jaw about the jaw axis in the second direction in the absence of the second cable routing protrusion.

24. The wrist assembly of claim 22, wherein the second cable routing protrusion is configured to reduce a first length change in the second cable during rotation of the first jaw about the jaw axis in the second direction relative to a second length change in the second cable during rotation of the first jaw about the jaw axis in the second direction in the absence of the second cable routing protrusion.

25. The wrist assembly of claim 1, wherein the first actuation hub further comprises a first fulcrum and a first cable pulley disposed about the first fulcrum.

26. The wrist assembly of claim 25, wherein the first actuation hub further comprises a second fulcrum and a second cable pulley disposed about the second fulcrum.

27. The wrist assembly of claim 26, wherein the second cable passes around the first cable pulley and the second cable pulley.

28. The wrist assembly of claim 27, wherein the second cable has a wrap angle around the first cable pulley of about 240 to 300 degrees, and the second cable has a wrap angle around the second cable pulley of less than about 110 degrees.

29. The wrist assembly of claim 1, wherein the first working segment and second working segment are configured to be electrically isolated from the rest of the jaw assembly.

30. The wrist assembly of claim 29, wherein the first working segment and second working segment are configured as a cautery tool.

31. The wrist assembly of claim 1, wherein the first jaw and second jaw are independently movable.

* * * * *